(12) United States Patent
Dransfield

(10) Patent No.: US 10,314,909 B2
(45) Date of Patent: Jun. 11, 2019

(54) COMBINATION THERAPY COMPRISING AN MMP-14 BINDING PROTEIN

(71) Applicant: DYAX CORP., Burlington, MA (US)

(72) Inventor: Daniel T. Dransfield, Hanson, MA (US)

(73) Assignee: Dyax Corp., Lexington, MA (US)

( * ) Notice: Subject to any disclaimer, the term of this patent is extended or adjusted under 35 U.S.C. 154(b) by 0 days.

(21) Appl. No.: 14/353,212

(22) PCT Filed: Oct. 18, 2012

(86) PCT No.: PCT/US2012/060791
§ 371 (c)(1),
(2) Date: Apr. 21, 2014

(87) PCT Pub. No.: WO2013/059439
PCT Pub. Date: Apr. 25, 2013

(65) Prior Publication Data
US 2014/0335082 A1   Nov. 13, 2014

Related U.S. Application Data

(60) Provisional application No. 61/549,873, filed on Oct. 21, 2011.

(51) Int. Cl.
| | | |
|---|---|---|
| *A61K 39/395* | (2006.01) | |
| *A61K 45/06* | (2006.01) | |
| *C07K 16/40* | (2006.01) | |
| *A61K 31/337* | (2006.01) | |
| *A61K 31/655* | (2006.01) | |
| *A61K 31/7068* | (2006.01) | |
| *A61K 39/00* | (2006.01) | |

(52) U.S. Cl.
CPC ........ *A61K 39/3955* (2013.01); *A61K 31/337* (2013.01); *A61K 31/655* (2013.01); *A61K 31/7068* (2013.01); *A61K 39/39558* (2013.01); *A61K 45/06* (2013.01); *C07K 16/40* (2013.01); *A61K 2039/505* (2013.01)

(58) Field of Classification Search
CPC .................................................... A61K 39/395
USPC ........................................... 424/158.1, 133.1
See application file for complete search history.

(56) References Cited

U.S. PATENT DOCUMENTS

| | | |
|---|---|---|
| 4,073,922 A | 2/1978 | Wyburn-Mason |
| 5,756,095 A | 5/1998 | Jutila |
| 6,114,159 A | 9/2000 | Will et al. |
| 6,184,022 B1 | 2/2001 | Seiki et al. |
| 6,232,098 B1 | 5/2001 | Conklin et al. |
| 6,339,348 B1 | 1/2002 | Fisher |
| 6,825,024 B1 | 11/2004 | Seiki et al. |
| 6,984,619 B1 | 1/2006 | Grdina et al. |
| 7,101,975 B1 | 9/2006 | Brooks et al. |
| 7,309,487 B2 | 12/2007 | Inana et al. |
| 7,745,587 B2 | 6/2010 | Devy et al. |
| 8,008,445 B2 | 8/2011 | Devy et al. |
| 8,013,125 B2 | 9/2011 | Devy |
| 8,106,168 B2 | 1/2012 | Devy et al. |
| 8,147,836 B2 | 4/2012 | Wood et al. |
| 8,183,008 B2 | 5/2012 | Wood et al. |
| 8,455,205 B2 | 6/2013 | Devy et al. |
| 8,501,181 B2 | 8/2013 | Wood et al. |
| 9,051,377 B2 | 6/2015 | Devy et al. |
| 2002/0159971 A1 | 10/2002 | Houde et al. |
| 2003/0180747 A1 | 9/2003 | Hruban et al. |
| 2004/0096899 A1 | 5/2004 | Aoki et al. |
| 2004/0115202 A1 | 6/2004 | Chen |
| 2004/0146499 A1 | 7/2004 | Wood et al. |
| 2004/0157278 A1 | 8/2004 | Astle et al. |
| 2005/0058725 A1 | 3/2005 | McKearn et al. |
| 2005/0118632 A1 | 6/2005 | Chen et al. |
| 2005/0129615 A1 | 6/2005 | Rozga et al. |
| 2005/0164928 A1 | 7/2005 | Ladner et al. |
| 2005/0260204 A1* | 11/2005 | Allan ............... A61K 39/39591 424/145.1 |
| 2006/0002969 A1 | 1/2006 | Kyriakides et al. |
| 2006/0036076 A1 | 2/2006 | Dransfield et al. |
| 2006/0062777 A1 | 3/2006 | Brooks et al. |
| 2006/0063204 A1 | 3/2006 | Valkirs et al. |
| 2006/0111272 A1 | 5/2006 | Roberts et al. |
| 2006/0142550 A1 | 6/2006 | Chang |
| 2006/0177448 A1* | 8/2006 | Carey .................... C07K 16/30 424/146.1 |
| 2006/0275294 A1 | 12/2006 | Omoigui |
| 2007/0112176 A1 | 5/2007 | Seiki et al. |
| 2007/0117848 A1 | 5/2007 | Puerta et al. |
| 2007/0172482 A1 | 7/2007 | Sagi et al. |
| 2007/0203209 A1 | 8/2007 | Bartolini et al. |

(Continued)

FOREIGN PATENT DOCUMENTS

| | | |
|---|---|---|
| CN | 1704409 A | 12/2005 |
| EP | 0736302 A2 | 10/1996 |

(Continued)

OTHER PUBLICATIONS

Ahonen et al. (Oncogene, 2003, 22: 2121-2134).*
Gura (Science. 1997; 278: 1041-1042).*
Dennis (Nature. Aug. 7, 2006; 442: 739-741).*
Seruga et al. (2015, Clin Cancer Res, 21: 4552-60).*
Reagan-Shaw et al. (FASEB J, 2007, 22: 659-61).*
Peterson et al., "Monoclonal antibody form and function: Manufacturing the right antibodies 13-14 for treating drug abuse," The AAPS Journal, 2006, vol. 8, No. 2, pp. E383-E390.

(Continued)

*Primary Examiner* — Yan Xiao
(74) *Attorney, Agent, or Firm* — Wolf, Greenfield & Sacks, P.C.

(57) ABSTRACT

Proteins that bind to matrix metalloproteinase 14, combination therapies with such proteins and methods of using such proteins are described.

35 Claims, 6 Drawing Sheets

Specification includes a Sequence Listing.

(56) References Cited

U.S. PATENT DOCUMENTS

| | | |
|---|---|---|
| 2007/0207184 A1 | 9/2007 | Ruane et al. |
| 2007/0207967 A1 | 9/2007 | Bjorklund et al. |
| 2007/0217997 A1 | 9/2007 | Devy et al. |
| 2007/0258987 A1 | 11/2007 | Francisco et al. |
| 2008/0076120 A1 | 3/2008 | Donaldson et al. |
| 2008/0090821 A1 | 4/2008 | Hofmeister et al. |
| 2008/0254490 A1 | 10/2008 | Menon |
| 2009/0090821 A1 | 4/2009 | Kim et al. |
| 2009/0136524 A1 | 5/2009 | Takafuji et al. |
| 2009/0150315 A1 | 6/2009 | Wirtz et al. |
| 2009/0186031 A1 | 7/2009 | Wood et al. |
| 2009/0203060 A1 | 8/2009 | Wood et al. |
| 2009/0209615 A1 | 8/2009 | Lipton et al. |
| 2009/0275124 A1 | 11/2009 | Muruganandam et al. |
| 2009/0297449 A1 | 12/2009 | Devy |
| 2009/0311245 A1 | 12/2009 | Devy et al. |
| 2010/0233188 A1 | 9/2010 | Sagi et al. |
| 2010/0266490 A1* | 10/2010 | Devy et al. .................. 424/1.17 |
| 2011/0135573 A1 | 6/2011 | Devy |
| 2011/0262396 A1 | 10/2011 | Wood |
| 2011/0300157 A1 | 12/2011 | Devy |
| 2012/0141473 A1 | 6/2012 | Wood et al. |
| 2013/0244890 A1 | 9/2013 | Wood et al. |
| 2014/0199324 A1 | 7/2014 | Dransfield |

FOREIGN PATENT DOCUMENTS

| | | |
|---|---|---|
| GB | 685557 A | 1/1953 |
| GB | 750672 A | 6/1956 |
| JP | 7203961 A | 8/1995 |
| JP | 10501962 T | 2/1998 |
| WO | 199804287 A1 | 2/1998 |
| WO | 199820159 A1 | 5/1998 |
| WO | 1999057315 A2 | 11/1999 |
| WO | 2001004157 A2 | 1/2001 |
| WO | 200126671 A1 | 4/2001 |
| WO | 2001090047 A1 | 11/2001 |
| WO | 200202773 A2 | 1/2002 |
| WO | 2002026829 A1 | 4/2002 |
| WO | 2002066057 A2 | 8/2002 |
| WO | 2003031434 A1 | 4/2003 |
| WO | 2003044058 A2 | 5/2003 |
| WO | 2003102148 A2 | 12/2003 |
| WO | 2004037286 A2 | 5/2004 |
| WO | 2004050683 A2 | 6/2004 |
| WO | 2004087042 A2 | 10/2004 |
| WO | 2006036860 A2 | 4/2006 |
| WO | 2006065533 A2 | 6/2006 |
| WO | 2007079096 A2 | 7/2007 |
| WO | 2007079218 A2 | 7/2007 |
| WO | 20071104541 A2 | 9/2007 |
| WO | 2008102359 A1 | 8/2008 |
| WO | 2009026539 A1 | 2/2009 |
| WO | 20091026334 A2 | 2/2009 |
| WO | 2009079581 A1 | 6/2009 |
| WO | 2009079585 A2 | 6/2009 |
| WO | 2009097397 A2 | 8/2009 |
| WO | 2009111450 A2 | 9/2009 |
| WO | 2009111508 A3 | 12/2009 |
| WO | 2010045388 A2 | 4/2010 |
| WO | 2010048432 A1 | 4/2010 |
| WO | 201102883 A1 | 1/2011 |
| WO | 2011028883 A2 | 3/2011 |
| WO | 2012129517 A2 | 9/2012 |
| WO | 2013059439 A2 | 4/2013 |

OTHER PUBLICATIONS

Philip et al., "Matrix metalloproteinase-2: Mechanism and regulation of NF-?B-mediated activation and its role in cell motility and ECM-invasion," Glycoconjugate Journal, 21, pp. 429-441, 2004.

Philip, S. et al., "Osteopontin Stimulates Tumor Growth and Activation of Promatrix Metalloproteinase-2 through Nuclear Factor-kB-mediated Induction of Membrane Type 1 Matrix Metalloproteinase in Murine Melanoma Cells", vol. 276, No. 48, pp. 44926-44935, Nov. 30, 2001.

Pilorget et al., "Inhibition of angiogenic properties of brain endothelial cells by platelet-derived sphingosine-1-phosphate," Journal of Cerebral Blood Flow & Metabolism, 25, pp. 1171-1182, 2005.

Plaisier et al., "Involvement of Membrane-Type Matrix Metalloproteinases (MT-MMPs) in Capillary Tube Formation by Human Endometrial Microvascular Endothelial Cells: Role of MT3-MMP," The Journal of Clinical Endocrinology & Metabolism, 89(11), pp. 5828-5836, 2004.

Price et al., "Identification of a matrix-degrading phenotype in human tuberculosis in vitro and in vivo", J. Immun., 2001, vol. 166, pp. 4223-4230.

Pruijt et al., "Prevention of interleukin-8-induced mobilization of hematopoietic progenitor cells in Rhesus monkeys by inhibitory antibodies against the metalloproteinase gelatinase B (MMP-9)", Proc. Nat. Acad. Sci., 1999, vol. 96, pp. 10863-10868.

Rajavashisth et al., "Membrane Type 1 Matrix Metalloproteinase Expression in Human Atherosclerotic Plaques: Evidence for Activation by Proinflammatory Mediators," Circulation, 99, pp. 3103-3109, 1999.

Ramos-Desimone et al., "Inhibition of matrix metalloproteinase 9 activation by a specific monoclonal antibody", Hybridoma, 1993, vol. 12, No. 4, pp. 349-363.

Ray et al., "Induction of the MMP-14 Gene in Macrophages of the Atherosclerotic Plaque: Role of SAF-1 in the Induction Process," Circulation Research, 95, pp. 1082-1090, 2004.

Raymond et al., "Recanalization of arterial thrombus, and inhibition with &radiation in a new murine carotid occlusion model: mRNA expression of angiopoietins, metalloproteinases, and their inhibitors," Journal of Vascular Surgery, 40 (6), pp. 1190-1198, Dec. 2004.

Riemer et al., "Matching of trastuzumab (Herceptin®) epitope mimics onto the surface of Her-2/neu—a new method of epitope definition" Mol. Immunol. vol. 42 pp. 1121-1124 (2005).

Roebuck et al., Matrix Metalloproteinase Expression Is Related to Angiogenesis and Histologic Grade in Spindle Cell Soft Tissue Neoplasms of the Extremities, American Journal of Clinical Pathology, 123(3), pp. 405-414, Mar. 2005.

Romanic et al., "Matrix metalloproteinase expression increases after cerebral focal ischemia in rats: inhibition of matrix metalloproteinase-9 reduces infarct size", Stroke, May 1998, vol. 29, No. 5, pp. 1020-1030.

Romanic et al., "Upregulated expression of human membrane type-5 matrix metalloproteinase in kidneys from diabetic patients," Am J Physiol Renal Physiol, 281, F309-317, 2001.

Rosen, "New Generation of Bisphosphonates: Broad Clinical Utility in Breast and Prostate Cancer", Oncology, vol. 18, No. 5 pp. 26-32 (2004).

Rowan et al., "Metalloproteases as potential therapeutic targets in arthritis treatment", Expert Opin. Ther. Targets 12, 1-18, 2008.

Rudikoff et al., "Single amino acid substitution altering antigen-binding specificity", PNAS, 1982, 79:1979.

Saijo et al., 37 What Are the Reasons for Negative Phase III Trials of Molecular-Target-Based Drugs?, Cancer Science, 95(10):772-776 (Oct. 2004).

Sakata et al., "Expression of Matrix Metalloproteinases (MMP-2, MMP-9, MT1-MMP) and Their Inhibitors (TIMP-1, TIMP-2) in Common Epithelial Tumors of the Ovary"; International Journal of Oncology, vol. 17 (2000) pp. 673-681.

Sanchez-Sweatman et al., "Human Metastatic Prostate PC3 Cell Lines Degrade Bone Using Matrix Metalloproteinases," Invasion Metastasis (199811999) vol. 18:297-305.

Sato et al., "Identification of the membrane-type matrix metalloproteinase MT1-MMP in osteoclasts," J. Cell Sci. (1997) vol. 110:589-596.

Sato et al., "Roles of membrane-type matrix metalloproteinase-1 in tumor invasion and metastasis," Cancer Sci, 96 (4), pp. 212-217, Apr. 2005.

Savinov et al., "Inhibition of Membrane Type-1 Matrix Metalloproteinase by Cancer Drugs Interferes with the Homing of

(56) References Cited

OTHER PUBLICATIONS

Diabetogenic T Cells into the Pancreas," The Journal of Biological Chemistry, 280(30), pp. 27755-27758, Jul. 29, 2005.
Seftor et al., "Cooperative interactions of laminin 5 g2 chain, matrix metalloproteinase-2, and membrane type-1 matrix/metalloproteinase are required for mimcry of embryonic vasculogenesis by aggressive melanoma", Cancer Res., Sep. 1, 2001, vol. 61, No. 17, pp. 6322-6327.
Sekine-Aizawa et al., "Matrix metalloproteinase (MMP) system in brain: identification and characterization of brain-specific MMP highly expressed in cerebellum," European Journal of Neuroscience, 13, pp. 935-948, 2001.
Shinoda et al., "A novel matrix metalloproteinase inhibitor, FYK-1388 suppresses tumor growth, metastasis and angiogenesis by human fibrosarcoma cell line", Int'l Journal of Oncology, 2003, vol. 22, pp. 281-288.
Shofuda et al., "Expression of Three Membrane-type Matrix Metalloproteinases (MT-MMPs) in Rat Vascular Smooth Muscle Cells and Characterization of MT3-MMPs with and without Transmembrane Domain," The Journal of Biological Chemistry, 272(15), pp. 9749-9754, Apr. 11, 1997.
Shrivastava, et al, "A distinct strategy to generate high-affinity peptide binders to receptor tyrosine kinases", PEDS 18(9), 417-424, 2005.
Sier et al., "Tissue Levels of Matrix Metalloproteinases MMP-2 and MMP-9 are Related to the Overall Survival of Patients with Gastric Carcinoma", British Journal of Cancer, vol. 74 (1996) pp. 413-417.
Simi et al., "Simultaneous measurement of MMP9 and TIMP1 mRNA in human non small cell lung cancers by multiplex real time RT-PCR", Lung Cancer, vol. 45, pp. 171-179 (2004).
Sood, A.K. et al., "Functional Role of Matrix Metalloproteinases in Ovarian Tumor Cell Plasticity", American Journal of Obstetrics & Gynecology, vol. 190, No. 4, pp. 899-909, Apr. 1, 2004.
Sounni et al., "Up-regulation of Vascular Endothelial Growth Factor-A by Active Membrane-type 1 Matrix Metalloproteinase through Activation of Src-Tyrosine Kinases,", the Journal of Biological Chemistry, 279(14), pp. 13564-13574, Apr. 2, 2004.
St. Jean et al., "Characterization of a dinucleotide repeat in the 92 kDa type IV collagenase gene (CLG4B), localization of CLG4B to chromosome 20 and the role of CLG4B in aortic aneurysmal disease", Ann. Hum. Genet., 1995, vol. 59, pp. 17-24.
Stadlmann et al., "Cytokine-regulated expression of collagenase-2 (MMP-8) is involved in the progression of ovarian cancer," European Journal of Cancer, 39, pp. 2499-2505, 2003.
Stancoviski et al. (Proceedings of the National Academy of Science USA. 1991; 88: 8691-8695).
Stawowy et al., "Furin-Like Proprotein Convertases Are Central Regulators of the Membrane Type Matrix Metalloproteinase-Pro-Matrix Metalloproteinase-2 Proteolytic Cascade in Atherosclerosis," Circulation, 111, pp. 2820-2827, 2005.
Strongin et al., "Mechanism of Cell Surface Activation of 72-kDA Type IV Collagenase," The Journal of Biological Chemistry, 270(10), pp. 5331-5338, Mar. 10, 1995.
Suenaga et al., "CD44 binding through the hemopexin-like domain is critical for its shedding by membrane-type 1 matrix metalloproteinase," Oncogene, 24, pp. 859-868, 2005.
Sun et al., "Expression of mRNA for Membrane-Type 1, 2, and 3 Matrix Metalloproteinases in Human Laryngeal Cancer," Chinese Medical Sciences Journal, 19(3), pp. 170-173, Sep. 2004.
Supplemental European Search Report dated Jul. 5, 2012 for EP 09 71 7527.
Szabova et al., "Expression Pattern of Four Membrane-Type Matrix Metalloproteinases in the Normal and Diseased Mouse Mammary Gland," Journal of Cellular Physiology, 205, pp. 123-132, 2005.
Takino et al., "Identification of the Second Membrane-type Matrix Metalloproteinase (MT-MMP-2) Gene from a Human Placenta cDNA Library," The Journal of Biological Chemistry, 270(39), pp. 23013-23020, Sep. 29, 1995.

Tamura et al., "Highly Selective and Orally Active Inhibitors of Type IV Collagenase", Journal of Medicinal Chemistry, vol. 41 (4), pp. 640-649, 1998.
Tanimura et al., "Specific blockade of the ERK pathway inhibits the invasiveness of tumor cells: down-regulation of matrix metalloproteinase-3/-9/-14 and CD 44," Biochemical and Biophysical Research Communications, 304, pp. 801-806, 2003.
Tchetina et al., "Increased Type II Collagen Degradation and Very Early Focal Cartilage Degeneration is Associated with Upregulation of Chondrocyte Differentiation Related Genes in Early Human Articular Cartilage Lesions," The Journal of Rheumatology, 32(5), pp. 876-886, 2005.
Tornetta et al., "Isolated of human anti-idiotypic antibodies by phage display for clinical immune response assays" Journal of Immunological Methods, vol. 328, pp. 34-44, 2007.
Toth et al., "Pro-MMP-9 activation by the MT1-MMP/MMP-2 axis and MMP-3: role of TIMP-2 and plasma membranes," Biochemical and Biophysical Research Communications, 308, pp. 386-395, 2003.
Trisciuoglio et al., "Bcl-2 Overexpression in Melanoma Cells Increases Tumor Progression-Associated Properties and In Vivo Tumor Growth," Journal of Cellular Physiology, 205, pp. 414-421, 2005.
Turner et al., "Role of matrix metalloproteinase 9 in pituitary tumor behavior", J. Clin. Endocr. Betab., 2000, vol. 85, pp. 2931-2935.
Andrews et al., "Gelatinase B (MMP-9) is not essential in the normal kidney and does not influence progression of renal disease in a mouse model of Alport syndrome", Am. J. Pathol., Jul. 2000, vol. 157, No. 1, pp. 303-311.
Anilkumar et al., "Palmitoylation at Cys574 is essential for MT1-MMP to promote cell migration, "The FASEB Journal, pp. 1-18, Jun. 8, 2005.
Aoki et al., "Cleavage of Apolipoprotein E by membrane-Type Matrix Metalloproteinase-1 Abrogates Suppression of Cell Proliferation," J. Biochem. 137, pp. 95-99 (2005).
Bauvois et al., "Transmembrane proteasese in cell growth and invasion: new contributors to angiogenesis?, "Oncogene, 23 pp. 317-329 (2004).
Bendig M.M., Methods: A Companion to Methods in Enzymology 1995:8:83-93.
Bergers et al., "Extrinsic Regulators of Epithelial Tumor Progression: Metalloproteinases", Current Opinion in Genetics and Development, 10:120-127, 2000.
Berno et al., "The 67 kDa laminin receptor increases tumor aggressiveness by remodeling laminin-1," Endocrine-Related Cancer, 12, pp. 393-406 (2005).
Bonfil et al. "Prostate Cancer-Associated Membrane Type 1-Matix Metalloproteinase" American Journal of Pathology 170(6): 2100-2111 2007.
Buisson-Legendre et al., "Relationship between cell-associated matrix metalloproteinase 9 and psoriatic keratinocyte growth", Journal of Investigative Dermatology, 2000, vol. 115, pp. 213-218.
Burrage et al., "Matrix Metalloproteinases: Role in Arthrits", Frontiers in Biosci. 529-543, 2006.
Butler et al., "The TIMP2 Membrane Type 1 Metalloproteinase "Receptor" Regulates the Concentration and Efficient Activation of Progelatinase A," The Journal of Biological Chemistry, 273(2), pp. 871-880, Jan. 9, 1998.
Cao et al., "Membrane type I-matrix metalloproteinase promotes human prostate cancer invasion and metastasis," Thromb Haemost, 93, p. 770-778, 2005.
Cao et al., "Membrane Type Matrix Metalloproteinase 1 Activates Pro-gelatinase A without Furin Cleavage of the N-terminal Domain," The Journal of Biochemistry, 271(47), pp. 30174-30180, Nov. 22, 1996.
Chang et al., "Activation Systems for Latent Matrix Metalloproteinase-2 Are Upregulated Immediately After Focal Cerebral Ischemia," Journal of Cerebral Blood Flow & Metabolism, 23, pp. 1408-1419, 2003.
Choi et al., "Expression of Matrix Metalloproteinases in the Muscle of Patients with Inflammatory Myopathies", Neurology, Jan. 2000, vol. 54, No. 1, pp. 1-5.

(56) References Cited

OTHER PUBLICATIONS

Collier et al., "On the structure and chromosome location of the 72- and 92- kDa human type IV collagenase genes", Genomics, 1991, vol. 9, pp. 429-434.
International Search Report dated May 14, 2008 from International Application No. PCT/US09/32384.
Coussens et al., "MMP-9 supplied by bone marrow-derived cells contributes to skin carcinogenesis", Cell, 2000, vol. 103, pp. 481-490.
Davis et al., "Matrix metalloproteinase-1 and -9 activation by plasmin regulates a novel endothelial cell-mediated mechanism of collagen gel contraction and capillary tube regression in three-dimensional collagen matrices", J. Cell Sci., Mar. 2001, vol. 114, Pt. 5, pp. 917-930.
Dennis, "Off by a Whisker", Nature. vol.,442, pp. 739-741 (2006).
Deryugina et al., "Unexpected Effect of Matrix Metalloproteinase Down-Regulation on Vascular Intravasation and Metastasis of Human Fibrosarcoma Cells Selected in vivo for High Rates of Dissemination," Cancer Res., 65(23), pp. 10959-10969, Dec. 1, 2005.
Devy et al., "Potent and selective antibody inhibitor of human matrix metalloproteinase-14 (MMP-14) inhibits tumor growth, invasion and angiogenesis," American Society of Clinical Oncology [Online], 2007 (retrieved online on 29 Sep. 2009), retrieved from the Internet at URL:http://www.asco.org/ASCOv2IMeetings/Abstracts&vmview=abst_detail_view&confID=52&abstractID=40128: abstract.
Devy et al., "Selective inhibition of MMP-14 inhibits tumor growth, invasion and angiogenesis", J. Clin. Oncol., May 20, 2008, 26(15S), Abstract 14022.
Di Carlo et al., "Urinary gelatinase activities (matrix metalloproteinases 2 and 9) in human bladder tumors", Oncol. Rep., 2006, vol. 15, pp. 1321-1326.
Distler et al., "The induction of matrix metalloproteinase and cytokine expression in synovial fibroblasts stimulated with immune cell microparticles," PNAS, 102(8), pp. 2892-2897, Feb. 22, 2005.
Dong et al., "Expression of Membrane-Type Matrix Metalloproteinases 4, 5, and 6 in Mouse Corneas Infected with P. aeruginosa," Investigative Ophthalmology & Visual Science, 42(13), pp. 3223-3227, Dec. 2001.
Dong et al., "Matrix Metalloproteinase Activity and Osteoclasts in Experimental Prostate Cancer Bone Metastasis Tissue," American Journal of Pathology, 166(4), pp. 1173-1186, Apr. 2005.
Dubios et al., "Resistance of young gelatinase B-deficient mice to experimental autoimmune encephalomyelitis and necrotizing tail lesions", J. Clin. Invest., 1999, vol. 104, pp. 1507-1515.
El Bedoui et al., "Catechins prevent vascular smooth muscle cell invasion by inhibiting MT1-MMP activity and MMP-2 expression," Cardiovascular Research, 67, pp. 317-315, 2005.
Extended European Search Report completed Jan. 25, 2013 for EP 09 82 2726.
Extended European Search Report dated Apr. 8, 2010 from European Application No. EP06848335.3.
Extended European Search Report from European Application No. 08862358.2 dated Jul. 11, 2012.
Folgueras et al., "Matrix metalloproteinases in cancer: from new functions to improved inhibition strategies," Int. J. Dev. Biol., 48, pp. 411-424 (2004).
Galvez et al., "Membrane Type 1-Matrix Metalloproteinase is Activated During Migration of Human Endothelial Cells and Modulates Endothelial Motility and Matrix Remodeling", The Journal of Biological Chemistry, vol. 276, 40:37491-37500, 2001.
Galvez et al., "Membrane Type 1-Matrix Metalloproteinase Is Regulated by Chemokines Monocyte-Chemoattractant Protein-1/CCL2 and Interleukin-8/CXCL8 in Endothelial Cells during Angiogenesis," The Journal of Biological Chemistry, 280(2), pp. 1292-1298, Jan. 14, 2005.
Giebel et al., "Matrix metalloproteinases in early diabetic retinopathy and their role in alteration of the blood-retinal barrier," Laboratory Investigation, 85, pp. 597-607, 2005.

Gijbels et al., "Gelatinase B is present in the cerebrospinal fluid during experimental autoimmune encephalomyelitis and cleaves myelin basic protein", J. Neurosci. Res., 1993, vol. 36, pp. 432-440.
Gijbels et al., "Gelatinase in the cerebrospinal fluid of patients with multiple sclerosis and other inflammatory neurological disorders", J. Neuroimmum., 1992, vol. 41, pp. 29-34.
Gilles et al., "Contribution of MT1-MMP and of human laminin-5 g2 chain degradation to mammary epithelial cell migration," Journal of Cell Science, 114, pp. 2967-2976, 2001.
Gilles et al., "Implication of Collagen Type I-Induced Membrane-Type 1-Matrix Metalloproteinase Expression and Matrix Metalloproteinase-2 Activation in the Metastatic Progression of Breast Carcinoma," Laboratory Investigation, 76 (5), pp. 651-660, 1997.
Goldbach-Mansky et al., "Active synovial matrix metalloproteinase-2 is associated with radiographic erosions in patients with early synovitis," Arthritis Res., 2, pp. 145-153, 2000.
Gonzalez et al., "Overexpression of Matrix Metalloproteinases in Their Inhibitors in Mononuclear Inflammatory Cells in Breast Cancer Correlates with Metastasis-Relapse", British Journal of Cancer, vol. 97 (2007) pp. 957-963.
Graubert et al., "Cloning and expression of the cDNA encoding mouse neutrophil gelatinase: demonstration of coordinate secondary granule protein gene expression during terminal neutrophil maturation", Blood, Nov. 15, 1993, vol. 82, No. 10, pp. 3192-1397.
Grossman, "Profiling the evolution of human metastatic bladder cancer," Urologic Oncology: Seminars and Original Investigations, 23, p. 222, 2005.
Grossman, "Small cell carcinoma of the urinary bladder: a clinicopathologic analysis of 64 patients," Urologic Oncology: Seminars and Original Investigations, 23, p. 222-223, 2005.
Gu et al., "S-nitrosylation of matrix metalloproteinases: signaling pathway to neuronal cell death", Science, 2002, vol. 297, pp. 1186-1190.
Guo et al., "Up-Regulation of Angiopoietin-2, Matrix Metalloprotease-2, Membrane Type 1 Metalloprotease, and Laminin 5 g 2 Correlates with the Invasiveness of Human Glioma," American Journal of Pathology, 166(3), pp. 877-890, Mar. 2005.
Gursoy-Ozdemir et al., "Cortical spreading depression activates and upregulates MMP-9", J. Clin. Invest., 2004, vol. 113, pp. 1447-1455.
Gussow et al., "Humanization of monoclonal antibodies" Methods in Enzymology, 1991; 203: 99-121.
Haas, "Endothelial cell regulation of matrix metalloproteinases," Can. J. Physiol. Pharmacol., 83, pp. 1-7, 2005.
Handsley et al., "Metalloproteinases and their inhibitors in tumor angiogenesis," Int. J. Cancer, 115, pp. 849-860, 2005.
Hanke et al., "Serum markers of matrix turnover as predictors for the evolution of colorectal cancer metastasis under chemotherapy" British Journal of Cancer, vol. 88, pp. 1248-1250 (2003).
Harrison et al., "The influence of CD44v3-v10 on adhesion, invasion and MMP-14 expression in prostate cancer cells," Oncology Reports, 15, pp. 199-206, 2006.
Hayashita-Kinoh et al., "Membrane-Type 5 Matrix Metalloproteinase Is Expressed in Differentiated Neurons and Regulates Axonal Growth," Cell Growth & Differentiation, 12, pp. 573-580, Nov. 2001.
Hayshidani et al., "Targeted deletion of MMP-2 attenuates early LV rupture and late remodeling after experimental myocardial infarction", Am. J. Physiol. Heart Circ. Physiol., 2003, vol. 285, pp. H1229-1235.
Heissig et al., "Recuitment of stem and progenitor cells from the bone marrow niche requires MMP-9 mediated release of Kit-ligand", Cell 2002, vol. 109, pp. 625-637.
Hernandez-Barrantes et al., "Regulation of membrane type-matrix metalloproteinases," Cancer Biology, 12, pp. 131-138, 2002.
Heymans et al., "Inhibition of plasminogen activators or matrix metalloproteinases prevents cardiac rupture but impairs therapeutic angiogenesis and causes cardiac failure", Nat. Med., 1999, vol. 5, pp. 1135-1142.
Heymans et al., "Inhibition of urokinase-type plasminogen activator or matrix metalloproteinases prevents cardiac injury and dysfunction during viral myocarditis", Circulation, 2006, vol. 114, pp. 565-573.

(56) References Cited

OTHER PUBLICATIONS

Heymans et al., "Loss or inhibition of uPA or MMP-9 attenuates LV remodeling and dysfunction after acute pressure overload in mice", Am. J. Pathol., vol. 166, pp. 15-25, 2005.
Hoet et al, "Generation of high-affinity human antibodies by combining donor-derived and synthetic complementarity-determining-region diversity" Nat. Biotechnol., vol. 23, pp. 344-348 (2005).
Holmbeck et al., "MT1-MMP-Deficient Mice Develop Dwarfism, Osteopenia, Arthritis, and Connective Tissue Disease due to Inadequate Collagen Turnover," Cell, 99, pp. 81-92, Oct. 1, 1999.
Notary et al., "Matrix Metalloproteinases (MMPs) Regulate Fibrin-invasive Activity via MT1-MMP-dependent and—independent Processes," J. Exp. Med., 195(3), pp. 295-308, Feb. 4, 2002.
Hudson et al., "Effects of selective matrix metalloproteinase inhibitor (PG-116800) to prevent ventricular remodeling after myocardial infarction: results of the Premier (Prevention of Myocardial Infarction Early Remodeling) trial", J. Am. Coll. Cardiol., 2006, vol. 48, pp. 15-20.
Huhtala et al., "Complete structure of the human gene for 92-kDa type IV collagenase: divergent regulation of expression for the 92- and 72-kilodalton enzyme genes in HT-1080 cells", J. Biol. Chem., 1991, vol. 266, pp. 16485-16490.
Hwang et al., "A proteomic approach to identify substrates of matrix metalloproteinase-14 in human plasma,". Biochimica et Biophysica Acta, 1702, pp. 79-87, 2004.
Iida et al., "Melanoma Chondroitin Sulfate Proteoglycan Regulates Matrix Metalloproteinase-dependent Human Melanoma Invasion into Type I Collagen," the Journal of Biological Chemistry, 276(22), pp. 18786-18794, Jun. 1, 2001.
International Preliminary Report on Patentability and Written Opinion dated Jul. 1, 2008 from corresponding International PCT Application PCT/US2006/049556.
International Preliminary Report on Patentability from PCT/US09/61717 dated Dec. 20, 2010.
International Search Report and Written Opinion from corresponding International Application No. PCT/US09/35926, dated May 28, 2009.
International Search Report and Written Opinion from International Application Serial No. PCT/US06/049566 dated May 14, 2008.
International Search Report and Written Opinion from International Application Serial No. PCT/US08/87236 dated Jun. 1, 2009.
International Search Report and Written Opinion from International Application Serial No. PCT/US2012/030398 dated Aug. 20, 2012.
International Search Report dated Feb. 24, 2009 from International Application No. PCT/US08187230.
International Search Report dated Mar. 10, 2011 from International Application No. PCT/US2010/47648.
International Search Report for Application No. PCT/US09/35840 dated Jun. 1, 2009.
International Search Report from PCT/US09/61717 dated Mar. 30, 2010.
International Search Report including Written Opinion dated Oct. 8, 2009 from International Application No. PCT/US09/41632.
International Search Report dated Mar. 30, 2010 for PCT/US09/61717.
Itoh, "MT1-MMP: a key regulator of cell migration in tissue", IUBMB Life, Oct. 2006, vol. 58, No. 10, pp. 589-596.
Jaworski et al., "Developmental regulation of membrane type-5 matrix metalloproteinase (MT5-MMP) expression in the rat nervous system," Brain Research, 860, pp. 174-177, 2000.
Jiang et al. (J. Biol. Chem. Feb. 11, 2005; 280 (6): 4656-4662).
Jiang et al., "Expression of Membrane Type-1 Matrix Metalloproteinase, MT1-MMP in Human Breast Cancer and its Impact on Invasiveness of Breast Cancer Cells", Int. J. Mol. Med., 17:583-590, 2006.
Johnson et al., "Matrix metalloproteinase-2 and -9 differentially regulate smooth muscle cell migration and cell-mediated collagen organization", Arterioscler Thromb. Vasc. Biol., 2004, vol. 24, pp. 54-60.

Kaliski et al., "Angiogenesis and tumor growth inhibition by a matrix metalloproteinase inhibitor targeting radiation-induced invasion", Mol. Cancer Ther., 2005, vol. 4, pp. 1717-1728.
Kang et al., "Functional characterization of MT3-MMP in transfected MDCK cells: progelatinase A activation and tubulogenesis in 3-D collagen lattice," The FASEB Journal, 14, pp. 2559-2568, Dec. 2000.
Katayama, A. et al., "Expressions of Matrix Metalloproteinases in Early-Stage Oral Squamous Cell Carcinoma as Predictive Indicators for Tumor Metastases and Prognosis", Clinical Cancer Research: An Official Journal of the American Association for Cancer Research, vol. 10, pp. 634-640, Jan. 15, 2004.
Kawamura et al., "In situ gelatinolytic activity correlates with tumor progression and prognosis in patients with bladder cancer", J. Urol., 2004, vol. 172, pp. 1480-1484.
Kelland, "Of mice and men"; values and liabilities of the athymic nude model in anticancer drug development (Eur. J. Cancer. Apr. 2004; 40 (6): 827-836).
Kelly et al., "Increased matrix metalloproteinase-9 in the airway after allergen challenge", Am. J. Resp. Crit. Care Med., 2000, vol. 162, pp. 1157-1161.
Kenagy et al., "Primate smooth muscle cell migration from aortic explants is mediated by endogenous platelet-derived growth factor and basic fibroblast growth factor acting through matrix metalloproteinases 2 and 9", Circulation, Nov. 18, 1997, vol. 96, No. 10, pp. 3555-3560.
Kevorkian et al., "Expression Profiling of Metalloproteinases and Their Inhibitors in Cartilage," Arthritis & Rheumatism, 50(1), pp. 131-141, Jan. 2004.
Kinoshita et al., "TIMP-2 Promotes Activation of Progelatinase a by Membrane-type 1 Matrix Metalloproteinase Immobilized on Agarose Beads," The Journal of Biological Chemistry, 273(26), pp. 16098-16103, Jun. 26, 1998.
Kitagawa et al., "Expression of Messenger RNAs for Membrane-Type 1, 2, and 3 Matrix Metalloproteinases in Human Renal Cell Carcinomas," The Journal of Urology, 162, pp. 905-909, Sep. 1999.
Kluft, "The Fibrinolytic System and Thrombotic Tendency," Pathophysiology of Haemostasis and Thrombosis, vol. 33, No. 5-6, pp. 425-429, Sep.-Oct. 2003/2004.
Knauper et al., "Cellular Mechanisms for Human Procollagenase-3 (MMP-13) Activation," The Journal of Biological Chemistry, 271(29), pp. 17124-17131, Jul. 19, 1996.
Koivunen et al., "Tumor targeting with a selective gelatinase inhibitor", Nature Biotechnology, Aug. 1999, vol. 17, pp. 768-774.
Komori et al., "Absence of mechanical allodynia and Aß-fiber sprouting after sciatic nerve injury in mice lacking membrane-type 5 matrix metalloproteinase," FEBS Letters, 557, pp. 125-128, 2004.
Konaka et al., "A Human Seminoma Xenograft Model With Regional Lymph Node Metastasis," The Journal of Urology, 161, pp. 342-248, Jan. 1999.
Koshida et al., "Correlation Between Expression of Metastasis-Related Genes and Lymph Node Metastasis in Testicular Cancer," Acta Urol. Jpn., 46(10), pp. 775-781, Oct. 2000.
Kousidou et al., "Genistein suppresses the invasive potential of human breast cancer cells through transcriptional regulation of metalloproteinases and their tissue inhibitors," International Journal of Oncology, 26(4), pp. 1101-1109, Apr. 2005.
La Rocca et al., "Zymographic detection and clinical correlations of MMP-2 and MMP-9 in breast cancer sera", Br. J. Cancer, 2004, vol. 90, pp. 1414-1421.
Lafleur et al., "Endothelial tubulogenesis within fibrin gels specifically requires the activity of membrane-type-matrix metalloproteinases (MT-MMPs)," Journal of Cell Science, 115(17), pp. 3427-3438, 2002.
Lafleur et al., "Upregulation of matrix metalloproteinases (MMPs) in breast cancer xenografts: A major induction of stromal MMP-13," Int. J. Cancer, 114, pp. 544-554 (2005).
Lambert et al., "MMP-2 and MMP-9 synergize in promoting choroidal neovascularization", FASEB J., 2003, vol. 17, pp. 2290-2292.

(56) References Cited

OTHER PUBLICATIONS

Larsen et al., "The expression of matrix metalloproteinase-12 by oligodendrocytes regulates their maturation and morphological differentiation", J. Neurosci., Sep. 1, 2004, vol. 24, No. 35, pp. 7597-7603.

Laterveer et al., "Rapid mobilization of hematopoietic progenitor cells in Rhesus monkeys by a single intraveneous injection of interleukin-8", Blood, 1996, vol. 87, pp. 781-788.

Lee et al., "A matrix metalloproteinase inhibitor, batimastat, retards the development of osteolytic bone metastase by MDA-MB-231 human breast cancer cells in Balb C nu/nu mice," Eur. J. Cancer, Jan. 2001, 37(1):106-13.

Lee et al., "Matrix metalloproteinase-9 and spontaneous hemorrhage in an animal model of cerebral amyloid angiopathy", Ann. Neurol., 2003, vol. 54, pp. 379-382.

Lee et al., "Unveiling the Surface Epitopes That Render Tissue Inhibitor of Metalloproteinase-1 Inactive against Membrane Type 1-Matrix Metalloproteinase," The Journal of Biological Chemistry, 278(41), pp. 40224-40230, Oct. 10, 2003.

Li et al., "Immunological Characterization of Cell-Surface and Soluble Forms of Membrane Type 1 Matrix Metalloproteinase in Human Breast Cancer Cells and in Fibroblasts", Molecular Carcinogenesis, vol. 22, No. 2, pp. 84-94, Jun. 1, 1998.

Lin et al., "Salvianolic acid B attenuates MMP-2 and MMP -9 expression in vivo in apolipoprotein-E-deficient mouse aorta and in vitro in LPS-treated human aortic smooth muscle cells", J. Cell Biochem., 2007, vol. 100, pp. 372-384.

Linn et al., "Reassingment of the 92-kDa type IV collagenase gene (CLG4B) to human chromosome 20", Cytogent. Cell Genet., 1996, vol. 72, pp. 159-161.

Lippincott-Schwartz, "Antibodies as Cell Biological Tools", Cellular and Molecular Immunology (Eds. Abass et al.; 1991; W.B. Saunders: Philadelphia; p. 54).

Liu et al., "Eradication of large colon tumor xenografts by targeted delivery of maytansinoids", Proc. Natl. Acad. Sci. USA, Aug. 1996, vol. 93, pp. 8618-8623.

Llano et al., "Identification and Characterization of Human MT5-MMP, a New Membrane-bound Activator of Progelatinase a Overexpressed in Brain Tumors," Cancer Research, 59, pp. 2570-2576, Jun. 1, 1999.

Lopez et al., "Human Carcinoma Cell Growth and Invasiveness Is Impaired by the Propeptide of the Ubiquitous Proprotein Convertase Furin," Cancer Research, 65(10), pp. 4162-4171, May 15, 2005.

Maccallum et al., "Antibody-antigen interactions: Contact analysis and binding site topography" J. Mol. Biol. 1996, 262:732-745.

Manes et al., "Identification of Insulin-like Growth Factor-binding Protein-1 as a Potential Physiological Substrate for Human Stromelysin-3," The Journal of Biological Chemistry, 272(41), pp. 25706-25712, Oct. 10, 1997.

Maquoi et al., "Membrane Type 1 Matrix Metalloproteinase-associated Degradation of Tissue Inhibitor of Metalloproteinase 2 in Human Tumor Cell Lines," The Journal of Biological Chemistry, 275(15), pp. 11368-11378, Apr. 14, 2000.

Mariuzza, et al., "The structural basis of antigen-antibody recognition." Ann. Rev. Biophys. Biophys. Chem. 1987, 16: 139-159.

Masson et al., "Contribution of host MMP-2 and MMP-9 to promote tumor vascularization and invasion of malignant keratinocytes", FASEB J. 2005, vol. 19, pp. 234-236.

Massova et al., "Matrix metalloproteinases: structures, evolution, and diversification" FASEB J. 12, 1075-1095 (1998).

Matsuyama et al., "Matrix metalloproteinase as novel disease markers in Takayasu arteritis", Circulation, 2003, vol. 108, pp. 1469-1473.

Matter et al., "Recent advances in the design of matrix metalloprotease inhibitors", Curr. Opin. Drug Disc. Dev., 7, 513-535, 2004.

May et al., "Plasminogen and matrix metalloproteinase activation by enzymatically modified low density lipoproteins in monocytes and smooth muscle cells," Thromb. Haemost., 93, pp. 710-715, 2005.

McLaughlin et al. Randomized study of adding inhaled iloprost to existing bosentan in pulmonary arterial hypertension. Am J Respir Crit Care Med 2006,174(11):1257-1263; abstract.

Minematsu et al., "Genetic polymorphism in matrix metalloproteinase-9 and pulmonary emphysema", Biochem. Biophys. Res. Commun., 2001, vol. 289, pp. 116-119.

Minond et al., "Matrix Metalloproteinase Triple-Helical Peptidase Activities Are Differentially Regulated by Substrate Stability," Biochemistry, 43, pp. 11474-11481, 2004.

Munshi et al., "Differential Regulation of Membrane Type 1-Matrix Metalloproteinase Activity by ERK ½- and p38 MAPK-modulated Tissue Inhibitor of Metalloproteinases 2 Expression Controls Transforming Growth Factor-ß1- induced Pericellular Collagenolysis," The Journal of Biological Chemistry, 279(37), pp. 39042-39050, Sep. 10, 2004.

Murphy et al., "Role of TIMPs (tissue inhibitors of metalloproteinases) in pericellular proteolysis: the specificity is in the detail," Biochem. Soc. Symp., 70, pp. 65-80, 2003.

Nagase et al., "Nomenclature and glossary of the matrix metalloproteinases", Matrix, 1992, vol. 1, pp. 421-424.

NCBI Locus CAC07541, retrieved from http://www.ncbi.nlm.nhi.gov/protein/9997653, retrieved May 14, 2009.

NCBI Locus NP_038627, retrieved from http://www.ncbi.nim.nih.gov/protein/7305277, retrieved May 14, 2009.

Nuttall et al., "Elevated Membrane-Type Matrix Metalloproteinases in Gliomas Revealed by Profiling Proteases and Inhibitors in Human Cancer Cells," Molecular Cancer Research, vol. 1, pp. 333-345, Mar. 2003.

Nyormoi et al., "An MMP-2/MMP-9 inhibitor, 5a, enhances apoptosis induced by ligands of the TNF receptor superfamily in cancer cells" Cell Death and Differentiation, vol. 10, No. 5. pp. 558-569 (2003).

O-Charoenrat et al., "Expression of Matrix Metalloproteinases and Their Inhibitors Correlates With Invasion and Metastasis in Squamous Cell Carcinoma of the Head and Neck", Arch Otolaryngol Head Neck Surg., vol. 127 (2001) pp. 813-820.

Ohnishi et al., "Coordinate expression of membrane type-matrix metalloproteinases-2 and 3 (MT2-MMP and MT3-MMP) and matrix metalloproteinase-2 (MMP-2) in primary and metastatic melanoma cells," European Journal of Dermatology, 11(5), pp. 420-423, Sep.-Oct. 2001.

OMIM Accession No. 600754; Matrix Metalloproteinase 14; Aug. 28, 1995.

Opdenakker et al., "Cytokine-mediated regulation of human leukocyte gelatinases and role in arthritis", Lymphokine Cytokine Res., 1991, vol. 10, pp. 317-324.

Opdenakker et al., "The molecular basis of leukocytosis", Immuno. Today, 1998, vol. 9, pp. 182-189.

Osenkowski et al., "Processing, Shedding, and Endocytosis of Membrane Type 1-Matrix Metalloproteinase (MT1- MMP)," Journal of Cellular Physiology, 200, pp. 2-10, 2004.

Osman et al., "Expression of matrix metalloproteinases and tissue inhibitors of metalloproteinases define the migratory characterisitics of human monocyte-derived dendritic cells", Immunology, 2002, vol. 105, pp. 73-82.

Udayakumar et al., "Fibroblast Growth Factor-I Transcriptionally Induces Membrane Type-I Matrix Metalloproteinase Expression in Prostate Carcinoma Cell Line," The Prostate, 58, pp. 66-75, 2004.

Ueda et al., "Surviving gene expression in endometriosis", J. Clin. Endocr. Metab., 2002, vol. 87, pp. 3452-3459.

Ueno et al., "Expression and Tissue Localization of Membrane-Types 1, 2, and 3 Matrix Metalloproteinases in Human Invasive Breast Carcinomas," Cancer Research, 57, pp. 2055-2060, May 15, 1997.

Uzui et al., "Increased Expression of Membrane Type 3-Matrix Metalloproteinase in Human Atherosclerotic Plaque: Role of Activated Macrophages and Inflammatory Cytokines," Circulation, 106, pp. 3024-3030, 2002.

Vadillo-Ortega et al., "92-kd type IV collagenase (matrix metalloproteinase-9) activity in human aminochorion increases with labor", Am. J. Pathol., Jan. 1995, vol. 146, No. 1, pp. 148-156.

(56) References Cited

OTHER PUBLICATIONS

Van Den Steen et al., "Neutrophil gelatinase B potentiates interleukin-8 tenfold by aminoterminal processing, whereas it degrades CTAP-III, PF-4, and GRO-a and leaves Rantes and MCP-2 intact", Blood, 2000, vol. 96, pp. 2673-2681.
Van Meter et al., "Induction of membrane-type-1 matrix metalloproteinase by epidermal growth factor-mediated signaling in gliomas," Neuro-Oncology, pp. 188-199, Jul. 2004.
Vizoso et al., "Study or Matrix Metalloproteinases and Their Inhibitors in Breast Cancer", British Journal of Cancer, vol. 96 (2007) pp. 903-911.
Vu et al., "MMP-9/gelatinase B is a key regulator of growth plate angiogenesis and apoptosis of hypertrophic chondrocytes", Cell, 1998, vol. 93, pp. 411-422.
Wan et al., "Effects of losartan on MT3-MMP and TIMP2 mRNA expressions in diabetic rat kidney," Journal of First Military Medical University, 24(12), pp. 1391-1394, Dec. 2004.
Wang et al., "Expression, purification and characterization of recombinant mouse MT5-MMP protein products," FEBS Letters, 462, pp. 261-266, 1999.
Oulu University Library, "Matrix metalloproteinases (MMPs) and their specific tissue inhibitors (TIMPs) in mature human odontoblasts and pulp tissue", 2003, http://herkules.oluMisbn9514270789/html/x561.html, retrieved on May 12, 2005, 9 pages.
Padlan et al., "Structure of an antibody-antigen complex: Crystal structure of the HyHel-10 Fab-lysozyme complex", PNAS 1989, 86:5938-5942.
Pap et al., "Differential Expression Pattern of Membrane-Type Matrix Metalloproteinases in Rheumatoid Arthritis," Arthritis & Rheumatism, 43(6), pp. 1226-1232, Jun. 2000.
Paquette et al., "In Vitro Irradiation of Basement Membrane Enhances the Invasiveness of Breast Cancer Cells", British Journal of Cancer, 97:1505-1512, 2007.
Pei, "Identification and Characterization of the Fifth Membrane-type Matrix Metalloproteinase MT5-MMP," The Journal of Biological Chemistry, 274(13), pp. 8925-8932, Mar. 26, 1999.
Peterson et al., "Matrix metalloproteinase inhibition attenuates left ventricular remodeling and dysfunction in a rat model of progressive heart failure", 2001, Circulation, vol. 103, pp. 2303-2309.
Wang et al., "Lipoprotein receptor-mediated induction of matrix metalloproteinase by tissue plasminogen activator", Nature Med., 2003, vol. 9, pp. 1313-1317.
Wang et al., "The Hemopexin Domain of Membrane-type Matrix Metalloproteinase-1 (MT1-MMP) Is Not Required for Its Activation of proMMP2 on Cell Surface but Is Essential for MT1-MMP-mediated Invasion in Three-dimensional Type I Collagen," The Journal of Biological Chemistry, 279(49), pp. 51148-51155, Dec. 3, 2004.
Whelan CJ, "Metalloprotease inhibitors as anti-inflammatory agents: An evolving target?" Curr. Opin. Investig. Drugs, 5, 511-516, 2004.
Winding et al., "Synthetic Matrix Metalloproteinase Inhibitors Inhibit Growth of Established Breast Cancer Osteolytic Lesions and Prolong Survival in Mice," Clinical Cancer Research, Jun. 2002, vol. 8:1932-1939.
Written Opinion from corresponding International Application No. PCT/US09/35840 dated Jun. 1, 2009.
Written Opinion from PCT/US09/61717 dated Mar. 23, 2010.
Yan et al., "Repression of 92-kDa type IV collagenase expression by MTA1 is mediated through direct interactions with the promoter via a mechanism, which is both dependent on and independent of histone deacetylation", J. Biol. Chem., 2003, vol. 278, pp. 2309-2316.
Yoshiyama et al., "Expression of the membrane-type 3 matrix metalloproteinase (MT3-MMP) in human brain tissue," Acta Neuropathol, 96, pp. 347-350, 1998.
Yu et al., "Cell surface-localized matrix metalloproteinase-9 proteolytically activates TGF-b and promotes tumor invasion and angiogenesis", Genes Dev., 2000, vol. 14, pp. 163-176.
Zhang, D. et al., "Type 1 insulin-like growth factor regulates MT1-MMP synthesis and tumor invasion via PI 3-kinase/Akt signaling", Oncogene, vol. 22, No. 7, pp. 974-982, Feb. 20, 2003.
Zhao et al., "Activation of pro-gelatinase B by endometase/matrilysin-2 promotes invasion of human prostate cancer cells", J. Biol. Chem., Apr. 25, 2003, vol. 278, No. 17, pp. 15056-15064.
Zhao et al., "Differential Inhibition of Membrane Type 3 (MT3)-Matrix Metalloproteinase (MMP) and MT1-MMP by Tissue Inhibitor of Metalloproteinase (TIMP)-2 and TIMP-3 Regulates Pro-MMP-2 Activation," The Journal of Biological Chemistry, 279(10), pp. 8592-8601, Mar. 5, 2004.
Zucker et al., "Imaging metalloproteinase activity in vivo," Nature Medicine, 7(6), pp. 655-656, Jun. 2001.
Zucker et al., "Membrane Type-Matrix Metalloproteinases (MT-MMP)," Current Topics in Developmental Biology, 54, pp. 1-74, 2003.
Zucker et al., "Role of matrix metalloproteinases (MMPs) in colorectal cancer," Cancer and Metastasis Reviews, vol. 23, pp. 101-117, 2004.
International Search Report and Written Opinion from corresponding International Application No. PCT/US12/60791 dated Jan. 24, 2013.

* cited by examiner

SEQUENCE LISTING

```
<160> NUMBER OF SEQ ID NOS: 53

<210> SEQ ID NO 1
<211> LENGTH: 339
<212> TYPE: DNA
<213> ORGANISM: Homo sapiens

<400> SEQUENCE: 1
caagacatcc agatgaccca gtctccactc tccctgcccg tcacccctgg agagccggcc      60
tccatctcct gcaggtctag tcagagcctc ctgcatagta atggatacta ctatttggat     120
tggtacctgc agaagccagg gcagtctcca caactcctga tctatttggg ttcttatcgg     180
gcctccgggg tccctgacag gttcagtggc agtggatcag gcacagattt tacactgaaa     240
atcagcagtg tggaggctga agatgttggg gtttattact gcatgcaagc tctacaaact     300
cctctcactt tcggcggagg gaccagggtg gacatcaaa                            339

<210> SEQ ID NO 2
<211> LENGTH: 582
<212> TYPE: PRT
<213> ORGANISM: Homo sapiens

<400> SEQUENCE: 2

Met Ser Pro Ala Pro Arg Pro Pro Arg Cys Leu Leu Leu Pro Leu Leu
1               5                   10                  15
```

```
Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
        210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
        370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430
```

```
Asn Lys Tyr Tyr Arg Phe Asn Glu Glu Leu Arg Ala Val Asp Ser Glu
            435                 440                 445
Tyr Pro Lys Asn Ile Lys Val Trp Gly Ile Pro Glu Ser Pro Arg
    450                 455                 460
Gly Ser Phe Met Gly Ser Asp Glu Val Phe Thr Tyr Phe Tyr Lys Gly
465                 470                 475                 480
Asn Lys Tyr Trp Lys Phe Asn Asn Gln Lys Leu Lys Val Glu Pro Gly
            485                 490                 495
Tyr Pro Lys Ser Ala Leu Arg Asp Trp Met Gly Cys Pro Ser Gly Gly
    500                 505                 510
Arg Pro Asp Glu Gly Thr Glu Glu Thr Glu Val Ile Ile Ile Glu
    515                 520                 525
Val Asp Glu Glu Gly Gly Gly Ala Val Ser Ala Ala Ala Val Val Leu
    530                 535                 540
Pro Val Leu Leu Leu Leu Leu Val Leu Ala Val Gly Leu Ala Val Phe
545                 550                 555                 560
Phe Phe Arg Arg His Gly Thr Pro Arg Arg Leu Leu Tyr Cys Gln Arg
            565                 570                 575
Ser Leu Leu Asp Lys Val
            580

<210> SEQ ID NO 3
<211> LENGTH: 378
<212> TYPE: DNA
<213> ORGANISM: Homo sapiens

<400> SEQUENCE: 3
gaagttcaat tgttagagtc tggtggcggt cttgttcagc ctggtggttc tttacgtctt    60
tcttgcgctg cttccggatt cacttttctct ccttacccta tgggttgggt tcgccaagct   120
cctggtaaag gtttggagtg gtttcttct atcgtttctt ctggtggcct tactctttat   180
gctgactccg ttaaaggtcg cttcactatc tctagagaca actctaagaa tactctctac   240
ttgcagatga acagcttaag ggctgaggac actgccgtgt attactgtgc gagaggggga   300
cggctttacg atattttgac tggtcaaggg gccccgtttg actactgggg ccagggaacc   360
ctggtcaccg tctcaagc                                                  378

<210> SEQ ID NO 4
<211> LENGTH: 582
<212> TYPE: PRT
<213> ORGANISM: Mus musculus

<400> SEQUENCE: 4

Met Ser Pro Ala Pro Arg Pro Ser Arg Ser Leu Leu Pro Leu Leu
1               5                   10                  15
Thr Leu Gly Thr Ala Leu Ala Ser Leu Gly Trp Ala Gln Gly Ser Asn
            20                  25                  30
Phe Ser Pro Glu Ala Trp Leu Gln Gln Tyr Gly Tyr Leu Pro Pro Gly
        35                  40                  45
Asp Leu Arg Thr His Thr Gln Arg Ser Pro Gln Ser Leu Ser Ala Ala
    50                  55                  60
Ile Ala Ala Met Gln Lys Phe Tyr Gly Leu Gln Val Thr Gly Lys Ala
65                  70                  75                  80
Asp Leu Ala Thr Met Met Ala Met Arg Arg Pro Arg Cys Gly Val Pro
            85                  90                  95
Asp Lys Phe Gly Thr Glu Ile Lys Ala Asn Val Arg Arg Lys Arg Tyr
```

```
            100                 105                 110
Ala Ile Gln Gly Leu Lys Trp Gln His Asn Glu Ile Thr Phe Cys Ile
        115                 120                 125
Gln Asn Tyr Thr Pro Lys Val Gly Glu Tyr Ala Thr Phe Glu Ala Ile
    130                 135                 140
Arg Lys Ala Phe Arg Val Trp Glu Ser Ala Thr Pro Leu Arg Phe Arg
145                 150                 155                 160
Glu Val Pro Tyr Ala Tyr Ile Arg Glu Gly His Glu Lys Gln Ala Asp
                165                 170                 175
Ile Met Ile Leu Phe Ala Glu Gly Phe His Gly Asp Ser Thr Pro Phe
            180                 185                 190
Asp Gly Glu Gly Gly Phe Leu Ala His Ala Tyr Phe Pro Gly Pro Asn
        195                 200                 205
Ile Gly Gly Asp Thr His Phe Asp Ser Ala Glu Pro Trp Thr Val Gln
    210                 215                 220
Asn Glu Asp Leu Asn Gly Asn Asp Ile Phe Leu Val Ala Val His Glu
225                 230                 235                 240
Leu Gly His Ala Leu Gly Leu Glu His Ser Asn Asp Pro Ser Ala Ile
                245                 250                 255
Met Ser Pro Phe Tyr Gln Trp Met Asp Thr Glu Asn Phe Val Leu Pro
            260                 265                 270
Asp Asp Asp Arg Arg Gly Ile Gln Gln Leu Tyr Gly Ser Lys Ser Gly
        275                 280                 285
Ser Pro Thr Lys Met Pro Pro Gln Pro Arg Thr Thr Ser Arg Pro Ser
    290                 295                 300
Val Pro Asp Lys Pro Lys Asn Pro Ala Tyr Gly Pro Asn Ile Cys Asp
305                 310                 315                 320
Gly Asn Phe Asp Thr Val Ala Met Leu Arg Gly Glu Met Phe Val Phe
                325                 330                 335
Lys Glu Arg Trp Phe Trp Arg Val Arg Asn Asn Gln Val Met Asp Gly
            340                 345                 350
Tyr Pro Met Pro Ile Gly Gln Phe Trp Arg Gly Leu Pro Ala Ser Ile
        355                 360                 365
Asn Thr Ala Tyr Glu Arg Lys Asp Gly Lys Phe Val Phe Phe Lys Gly
    370                 375                 380
Asp Lys His Trp Val Phe Asp Glu Ala Ser Leu Glu Pro Gly Tyr Pro
385                 390                 395                 400
Lys His Ile Lys Glu Leu Gly Arg Gly Leu Pro Thr Asp Lys Ile Asp
                405                 410                 415
Ala Ala Leu Phe Trp Met Pro Asn Gly Lys Thr Tyr Phe Phe Arg Gly
            420                 425                 430
Asn Lys Tyr Tyr Arg Phe Asn Glu Glu Phe Arg Ala Val Asp Ser Glu
        435                 440                 445
Tyr Pro Lys Asn Ile Lys Val Trp Glu Gly Ile Pro Glu Ser Pro Arg
    450                 455                 460
Gly Ser Phe Met Gly Ser Asp Glu Val Phe Thr Tyr Phe Tyr Lys Gly
465                 470                 475                 480
Asn Lys Tyr Trp Lys Phe Asn Asn Gln Lys Leu Lys Val Glu Pro Gly
                485                 490                 495
Tyr Pro Lys Ser Ala Leu Arg Asp Trp Met Gly Cys Pro Ser Gly Arg
            500                 505                 510
Arg Pro Asp Glu Gly Thr Glu Glu Glu Thr Glu Val Ile Ile Ile Glu
        515                 520                 525
```

Val Asp Glu Glu Gly Ser Gly Ala Val Ser Ala Ala Val Val Leu
         530                 535                 540

Pro Val Leu Leu Leu Leu Val Leu Ala Val Gly Leu Ala Val Phe
545                 550                 555                 560

Phe Phe Arg Arg His Gly Thr Pro Lys Arg Leu Leu Tyr Cys Gln Arg
             565                 570                 575

Ser Leu Leu Asp Lys Val
             580

<210> SEQ ID NO 5
<211> LENGTH: 333
<212> TYPE: DNA
<213> ORGANISM: Homo sapiens

<400> SEQUENCE: 5
cagagcgaat tgactcagcc accctcagtg tctgggaccc ccgggcagag ggtcaccatc      60
tcttgttctg gaaccagcgc caacatcgga cgtaatgctg tacactggta ccagcagctc    120
ccaggaacgg cccccaaact cctcattcat agtaataacc ggcggccctc aggggtccct    180
gaccgattct ctggctccaa gtctggcacc tcagcctccc tggccatcag tgggctccag    240
tctgaggatg aggctgatta ttactgtgca gcatgggaga cagcctgaa tgccttttat     300 gtcttcggaa ctgggaccaa ggtcaccgtc cta                                  333

<210> SEQ ID NO 6
<211> LENGTH: 375
<212> TYPE: DNA
<213> ORGANISM: Homo sapiens

<400> SEQUENCE: 6
gaagttcaat tgttagagtc tggtggcggt cttgttcagc ctggtggttc tttacgtctt     60
tcttgcgctg cttccggatt cactttctct acttacgaga tgcattgggt tcgccaagct   120
cctggtaaag gtttggagtg gtttcttcct atctattctt ctggtggctg gactggttat   180
gctgactccg ttaaaggtcg cttcactatc tctagagaca actctaagaa tactctctac   240
ttgcagatga acagcttaag ggctgaggac acggccgtgt attactgtgc gagatctcaa   300
cagtattacg attttttcctc tcgctactac ggcatggacg tctggggcca agggaccacg   360
gtcaccgtct caagc                                                       375

<210> SEQ ID NO 7
<211> LENGTH: 324
<212> TYPE: DNA
<213> ORGANISM: Homo sapiens

<400> SEQUENCE: 7
caagacatcc agatgaccca gtctccatcc tccctgtctg catctgtagg agacagagtc      60
accatcactt gccgggcgag tcagggcatt aggaattttt tagcctggta tcagcagaaa   120
ccagggaaag ttcctaagct cctggtcttt ggtgcatccg ctttgcaatc gggggtccca   180
tctcggttca gtggcagtgg atctgggaca gatttcactc tcaccatcag cggcctgcag   240
cctgaggatg ttgcaactta ttactgtcaa aagtataacg tgtcccgct cactttcggc    300 ggagggacca aggtggagat caaa                                             324

<210> SEQ ID NO 8
<211> LENGTH: 360
<212> TYPE: DNA

<213> ORGANISM: Homo sapiens

<400> SEQUENCE: 8

```
gaagttcaat tgttagagtc tggtggcggt cttgttcagc ctggtggttc tttacgtctt    60
tcttgcgctg cttccggatt cactttctct gtttacggta tggtttgggt tcgccaagct   120
cctggtaaag gtttggagtg ggtttctgtt atctcttctt ctggtggctc tacttggtat   180
gctgactccg ttaaaggtcg cttcactatc tctagagaca actctaagaa tactctctac   240
ttgcagatga acagcttaag ggctgaggac accgccttgt attactgtgc gagaccgttc   300
agtagaagat acggcgtctt tgactactgg ggccagggca ccctggtcac cgtctcaagc   360
```

<210> SEQ ID NO 9
<211> LENGTH: 339
<212> TYPE: DNA
<213> ORGANISM: Homo sapiens

<400> SEQUENCE: 9

```
caagacatcc agatgaccca gtctccactc tccctgcccg tcaccctggg agagtcggcc    60
tccgtctcct gcaggtctag tcagagcctc ttcatgaaaa atggacacaa ctatttggat   120
tggtacctgc agaagccagg gcagtctcca cagctcctga tctatttggg ttctaatcgg   180
gcctccgggg tccctgacag gttcagtggc agtggatcag gcacagattt tacactgaaa   240
atcagcagag tggaggctga ggatgttggg gtttattact gcatgcaatc tctaaagact   300
cctccgacgt tcggcccagg gaccaaggtg gaaatcaaa                          339
```

<210> SEQ ID NO 10
<211> LENGTH: 375
<212> TYPE: DNA
<213> ORGANISM: Homo sapiens

<400> SEQUENCE: 10

```
gaagttcaat tgttagagtc tggtggcggt cttgttcagc ctggtggttc tttacgtctt    60
tcttgcgctg cttccggatt cactttctct cattacgaga tgttttgggt tcgccaagct   120
cctggtaaag gtttggagtg ggtttcttct atctctcctt ctggtggcca gactcattat   180
gctgactccg ttaaaggtcg cttcactatc tctagagaca actctaagaa tactctctac   240
ttgcagatga acagcttaag ggctgaggac actgccgtgt attactgtgc cacagatcgg   300
acgtattacg attttttggag tggttatggg cccctgtggt actggggcca gggaaccctg   360
gtcaccgtct caagc                                                    375
```

<210> SEQ ID NO 11
<211> LENGTH: 324
<212> TYPE: DNA
<213> ORGANISM: Homo sapiens

<400> SEQUENCE: 11

```
caagacatcc agatgaccca gtctccatcc tccctgtctg catctgtcgg agacagagtc    60
accatcactt gccgggcaag tcagggcatt agaaatgatt taggctggta tcagcagaaa   120
ccagggaaag cccctaagcg cctgatctat gttgcatcca gtttgcaaag tggggtccca   180
tcaaggttca gcggcagtgg atctgggaca gaattcactc tcacaatcag cagcctgcag   240
cctgaagatt ttgcaactta ttactgtcta cagcataata gttacccgtg gacgttcggc   300
caagggacca aggtggaaat caaa                                          324
```

<210> SEQ ID NO 12
<211> LENGTH: 375
<212> TYPE: DNA
<213> ORGANISM: Homo sapiens

<400> SEQUENCE: 12

| gaagttcaat tgttagagtc tggtggcggt cttgttcagc ctggtggttc tttacgtctt | 60 |
| tcttgcgctg cttccggatt cactttctct atgtacatga tgatttgggt tcgccaagct | 120 |
| cctggtaaag gtttggagtg ggtttcttct atctatcctt ctggtggcaa tactatgtat | 180 |
| gctgactccg ttaaaggtcg cttcactatc tctagagaca actctaagaa tactctctac | 240 |
| ttgcagatga acagcttaag ggctgaggac acggccgtgt attactgtgc cacaggtgta | 300 |
| ttacgatatt ttgactggga tgctgggagc ggtatggacg tctggggcca agggaccacg | 360 |
| gtcaccgtct caagc | 375 |

<210> SEQ ID NO 13
<211> LENGTH: 327
<212> TYPE: DNA
<213> ORGANISM: Homo sapiens

<400> SEQUENCE: 13

| caagacatcc agatgaccca gtctccaggc accctgtcct tgtctccagg ggacagagcc | 60 |
| accctctcct gcggggccag ccagcttgtt gtcagcaact acatagcctg gtaccagcaa | 120 |
| aaacctggcc aggctcccag actcctcatg tatgctggat ccatcagggc cactggcatc | 180 |
| ccagacaggt tcagtggcag tgggtctggg acagacttca ctctcaccat cagcagacta | 240 |
| gaacctgaag attttgcaat atattactgt cagcagcgta gcaactggcc ttggacgttc | 300 |
| ggccaaggga ccaaggtgga aatcaaa | 327 |

<210> SEQ ID NO 14
<211> LENGTH: 354
<212> TYPE: DNA
<213> ORGANISM: Homo sapiens

<400> SEQUENCE: 14

| gaagttcaat tgttagagtc tggtggcggt cttgttcagc ctggtggttc tttacgtctt | 60 |
| tcttgcgctg cttccggatt cactttctct ccttacgtta tgcattgggt tcgccaagct | 120 |
| cctggtaaag gtttggagtg ggtttcttct atctctcctt ctggtggctg gacttattat | 180 |
| gctgactccg ttaaaggtcg cttcactatc tctagagaca actctaagaa tactctctac | 240 |
| ttgcagatga acagcttaag ggctgaggac atggctgtgt attactgtgc gagagggact | 300 |
| ggagcctacg gtatggacgt ctggggccaa gggaccacgg tcaccgtctc aagc | 354 |

<210> SEQ ID NO 15
<211> LENGTH: 327
<212> TYPE: DNA
<213> ORGANISM: Homo sapiens

<400> SEQUENCE: 15

| caagacatcc agatgaccca gtctccatcc tccctgtctg catttgtagg agacaaagtc | 60 |
| accatcactt gccgggcaag tcagagtgtt ggcacctatt taaattggta tcagcagaaa | 120 |
| gcagggaaag cccctgagct cctgatctat gctacatcca atttgcgaag tggggtccca | 180 |
| tcaaggttca gtggcagtgg atctgggaca gatttcactc tcaccatcaa cactctgcaa | 240 |
| cctgaagatt ttgcaactta ctactgtcaa cagagttaca gtatccctcg gtttactttc | 300 |

```
ggccctggga ccaaagtgga tatcaaa                                     327
```

<210> SEQ ID NO 16
<211> LENGTH: 345
<212> TYPE: DNA
<213> ORGANISM: Homo sapiens

<400> SEQUENCE: 16

```
gaagttcaat tgttagagtc tggtggcggt cttgttcagc ctggtggttc tttacgtctt    60
tcttgcgctg cttccggatt cactttctct ctttactcta tgaattgggt tcgccaagct   120
cctggtaaag gtttggagtg gtttcttct  atctattctt ctggtggctc tactctttat   180
gctgactccg ttaaaggtcg cttcactatc tctagagaca actctaagaa tactctctac   240
ttgcagatga acagcttaag ggctgaggac acggccgtgt attactgtgc gagaggtcgg   300
gcttttgata tctggggcca agggacaatg gtcaccgtct caagc                   345
```

<210> SEQ ID NO 17
<211> LENGTH: 324
<212> TYPE: DNA
<213> ORGANISM: Homo sapiens

<400> SEQUENCE: 17

```
caagacatcc agatgaccca gtctccaggc accctgtctt tgtctccagg ggaaagagcc    60
accctctcct gcagggccag tcagagtgtt agcagcagct acttagcctg gtaccagcag   120
aaacctggcc aggctcccag gctcctcatc tatggtgcat ccagcagggc cactggcatc   180
ccagacaggt tcagtggcag tgggtctggg acagacttca ctctcaccat cagcagactg   240
gagcctgaag attttgcagt gtattactgt cagcactatg gtggctcaca ggctttcggc   300
ggagggacca aggtggagat caaa                                          324
```

<210> SEQ ID NO 18
<211> LENGTH: 357
<212> TYPE: DNA
<213> ORGANISM: Homo sapiens

<400> SEQUENCE: 18

```
gaagttcaat tgttagagtc tggtggcggt cttgttcagc ctggtggttc tttacgtctt    60
tcttgcgctg cttccggatt cactttctct cgttacaaga tgtggtgggt tcgccaagct   120
cctggtaaag gtttggagtg gtttctggt  atccgtcctt ctggtggcct tactcgttat   180
gctgactccg ttaaaggtcg cttcactatc tctagagaca actctaagaa tactctctac   240
ttgcagatga acagcttaag ggctgaggac acggccgtgt attactgtgc gagacgcggt   300
gactacgtcg ggggtttga  ctactggggc caggaaccc  tggtcaccgt ctcaagc      357
```

<210> SEQ ID NO 19
<211> LENGTH: 327
<212> TYPE: DNA
<213> ORGANISM: Homo sapiens

<400> SEQUENCE: 19

```
caagacatcc agatgaccca gtctccagcc accctgtctg tgtctccagg ggaaagagcc    60
accctctcct gcagggccag tgagagtgtt aaaaacaact  tagcctggta tcagcagaaa   120
cctggccagg ctcccaggct cctcatctat ggtgtttcca ccagggcccc tggtatccca   180
gccaggttca gtggcagtgg gtctgggaca gacttcactc tcaccatcag cagcctagag   240
cctgaagatt ttgcagtttta ttactgtcag cagcgtagca actggcctcc ggtcaccttc   300
```

```
ggccaaggga cacgactgga gattaaa                                        327
```

<210> SEQ ID NO 20
<211> LENGTH: 351
<212> TYPE: DNA
<213> ORGANISM: Homo sapiens

<400> SEQUENCE: 20

```
gaagttcaat tgttagagtc tggtggcggt cttgttcagc ctggtggttc tttacgtctt     60
tcttgcgctg cttccggatt cactttctct gcttacaata tgggttgggt tcgccaagct    120
cctggtaaag gtttggagtg gtttcttct atctcttctt ctggtggcta tactggttat    180
gctgactccg ttaaaggtcg cttcactatc tctagagaca actctaagaa tactctctac    240
ttgcagatga acagcttaag ggctgaggac acggccgtgt attactgtgc gagagatctt    300
tacaggggct ttgactactg ggccaggga accctggtca ccgtctcaag c              351
```

<210> SEQ ID NO 21
<211> LENGTH: 339
<212> TYPE: DNA
<213> ORGANISM: Homo sapiens

<400> SEQUENCE: 21

```
caggacatcg tcatgactca aacccctcct agtttaccgg ttaacccggg tgaacctgcc     60
tccatctcct gcaggtctag tcagagcctc ctgcatagaa atggatacaa ctatttggat    120
tggtacctgc agaagccagg gcagtctcca cagctcctga tccatttggg ttcttatcgg    180
gcctccgggg tccctgacag gttcagtggc agtggatcag gcacagattt tacactgaaa    240
atcagcagag tggaggctga ggatgttggg gtttattact gcatgcaacc tctacaaact    300
ccattcactt tcggccctgg gaccaaagtg gatatcaaa                           339
```

<210> SEQ ID NO 22
<211> LENGTH: 372
<212> TYPE: DNA
<213> ORGANISM: Homo sapiens

<400> SEQUENCE: 22

```
gaagttcaat tgttagagtc tggtggcggt cttgttcagc ctggtggttc tttacgtctt     60
tcttgcgctg cttccggatt cactttctct tattacggta tgtattgggt tcgccaagct    120
cctggtaaag gtttggagtg gtttcttct atctcttctt ctggtggcta tactgattat    180
gctgactccg ttaaaggtcg cttcactatc tctagagaca actctaagaa tactctctac    240
ttgcagatga acagcttaag ggctgaggac acggccgtgt attactgtgc aaggaggatt    300
aagtattacg atattgaagg ggaaggtgct tttgatatct ggggccaagg acaatggtc     360 accgtctcaa gc                                                        372
```

<210> SEQ ID NO 23
<211> LENGTH: 333
<212> TYPE: DNA
<213> ORGANISM: Homo sapiens

<400> SEQUENCE: 23

```
cagagcgctt tgactcagcc tccctccgcg tccgggtctc ctggacagtc agtcaccatc     60
tcctgcactg gaaccagcag tgacgttggt gcttataact atgtctcctg gtaccaacag    120
cacccagaca agcccccaa actcattatt tataatgtca atgagcggcc ctcaggggtc    180
```

```
cctgatcgct tctctggctc caagtctggc aacacggcct ccctgaccgt ctctgggctc    240
caggctgagg atgaggctga ttattactgt acctcatatg caggcagcaa caaaatcggg    300
gtctccggaa ctgggaccaa ggtcaccgtc cta                                 333
```

```
<210> SEQ ID NO 24
<211> LENGTH: 366
<212> TYPE: DNA
<213> ORGANISM: Homo sapiens

<400> SEQUENCE: 24
gaagttcaat tgttagagtc tggtggcggt cttgttcagc ctggtggttc tttacgtctt     60
tcttgcgctg cttccggatt cactttctct cattacgtta tgttttgggt tcgccaagct    120
cctggtaaag gtttggagtg gtttctcgt atcgttcctt ctggtggcgc tactatgtat    180
gctgactccg ttaaaggtcg cttcactatc tctagagaca actctaagaa tactctctac    240
ttgcagatga acagcttaag ggctgaggac acggccgtgt attactgtgc gagagatcga    300
ccgctctatg atagtagtgg ttacgttgac tactggggcc agggaaccct ggtcaccgtc    360
tcaagc                                                               366
```

```
<210> SEQ ID NO 25
<211> LENGTH: 315
<212> TYPE: DNA
<213> ORGANISM: Homo sapiens

<400> SEQUENCE: 25
caagacatcc agatgaccca gtctccaggc accctgtctt tgtctccagg ggaaagagcc     60
accctctcct gcagggccag tcagagtgtt agcagcagct acttagcctg gtaccagcag    120
aaacctggcc aggctcccag gctcctcatc tatggtgcat ccagcagggc cactggcatc    180
ccagacaggt tcagtggcag tgggtctggg acagacttca ctctcaccat cagcagactg    240
gagcctgaag attttgcagt gtattactgt cagtcggggg tcactttcgg cggagggacc    300
aaggtggaga tcaaa                                                     315
```

```
<210> SEQ ID NO 26
<211> LENGTH: 384
<212> TYPE: DNA
<213> ORGANISM: Homo sapiens

<400> SEQUENCE: 26
gaagttcaat tgttagagtc tggtggcggt cttgttcagc ctggtggttc tttacgtctt     60
tcttgcgctg cttccggatt cactttctct tggtacccta tgttttgggt tcgccaagct    120
cctggtaaag gtttggagtg gtttctggt atctattctt ctggtggccc tactgattat    180
gctgactccg ttaaaggtcg cttcactatc tctagagaca actctaagaa tactctctac    240
ttgcagatga acagcttaag ggctgaggac acggccgtgt attactgtgc aaaagatacc    300
ctagggaggt attacgattt ttggagtggt tattcctacg gtatggacgt ctggggccaa    360
gggaccacgg tcaccgtctc aagc                                           384
```

```
<210> SEQ ID NO 27
<211> LENGTH: 126
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
```

```
                1               5                        10                       15
           Ser Leu Arg Leu Ser Cys Ala Ala Ser Gly Phe Thr Phe Ser Pro Tyr
                           20                      25                  30

Pro Met Gly Trp Val Arg Gln Ala Pro Gly Lys Gly Leu Glu Trp Val
                       35                      40                  45

Ser Ser Ile Val Ser Ser Gly Gly Leu Thr Leu Tyr Ala Asp Ser Val
                   50                      55                  60

Lys Gly Arg Phe Thr Ile Ser Arg Asp Asn Ser Lys Asn Thr Leu Tyr
           65                      70                  75                  80

Leu Gln Met Asn Ser Leu Arg Ala Glu Asp Thr Ala Val Tyr Tyr Cys
                               85                  90                  95

Ala Arg Gly Gly Arg Leu Tyr Asp Ile Leu Thr Gly Gln Gly Ala Pro
                           100                     105                 110

Phe Asp Tyr Trp Gly Gln Gly Thr Leu Val Thr Val Ser Ser
                       115                     120                 125

<210> SEQ ID NO 28
<211> LENGTH: 113
<212> TYPE: PRT
<213> ORGANISM: Homo sapiens

<400> SEQUENCE: 28

Gln Asp Ile Gln Met Thr Gln Ser Pro Leu Ser Leu Pro Val Thr Pro
           1               5                       10                      15

Gly Glu Pro Ala Ser Ile Ser Cys Arg Ser Ser Gln Ser Leu Leu His
                           20                      25                  30

Ser Asn Gly Tyr Tyr Tyr Leu Asp Trp Tyr Leu Gln Lys Pro Gly Gln
                       35                      40                  45

Ser Pro Gln Leu Leu Ile Tyr Leu Gly Ser Tyr Arg Ala Ser Gly Val
                   50                      55                  60

Pro Asp Arg Phe Ser Gly Ser Gly Ser Gly Thr Asp Phe Thr Leu Lys
           65                      70                  75                  80

Ile Ser Ser Val Glu Ala Glu Asp Val Gly Val Tyr Tyr Cys Met Gln
                               85                  90                  95

Ala Leu Gln Thr Pro Leu Thr Phe Gly Gly Gly Thr Arg Val Asp Ile
                           100                     105                 110

Lys

<210> SEQ ID NO 29
<211> LENGTH: 125
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
           1               5                       10                      15

Ser Leu Arg Leu Ser Cys Ala Ala Ser Gly Phe Thr Phe Ser Thr Tyr
                           20                      25                  30

Glu Met His Trp Val Arg Gln Ala Pro Gly Lys Gly Leu Glu Trp Val
                       35                      40                  45

Ser Ser Ile Tyr Ser Ser Gly Trp Thr Gly Tyr Ala Asp Ser Val
                   50                      55                  60

Lys Gly Arg Phe Thr Ile Ser Arg Asp Asn Ser Lys Asn Thr Leu Tyr
           65                      70                  75                  80

Leu Gln Met Asn Ser Leu Arg Ala Glu Asp Thr Ala Val Tyr Tyr Cys
                               85                  90                  95
```

Ala Arg Ser Gln Gln Tyr Tyr Asp Phe Ser Ser Arg Tyr Tyr Gly Met
            100                 105                 110

Asp Val Trp Gly Gln Gly Thr Thr Val Thr Val Ser Ser
            115                 120                 125

<210> SEQ ID NO 30
<211> LENGTH: 111
<212> TYPE: PRT
<213> ORGANISM: Homo sapiens

<400> SEQUENCE: 30

Gln Ser Glu Leu Thr Gln Pro Pro Ser Val Ser Gly Thr Pro Gly Gln
1               5                   10                  15

Arg Val Thr Ile Ser Cys Ser Gly Thr Ser Ala Asn Ile Gly Arg Asn
            20                  25                  30

Ala Val His Trp Tyr Gln Gln Leu Pro Gly Thr Ala Pro Lys Leu Leu
        35                  40                  45

Ile His Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Glu Asn Ser Leu
                85                  90                  95

Asn Ala Phe Tyr Val Phe Gly Thr Gly Thr Lys Val Thr Val Leu
            100                 105                 110

<210> SEQ ID NO 31
<211> LENGTH: 120
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Gly Met Val Trp Val Arg Gln Ala Pro Gly Lys Gly Leu Glu Trp Val
        35                  40                  45

Ser Val Ile Ser Ser Ser Gly Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Pro Phe Ser Arg Arg Tyr Gly Val Phe Asp Tyr Trp Gly Gln
            100                 105                 110

Gly Thr Leu Val Thr Val Ser Ser
            115                 120

<210> SEQ ID NO 32
<211> LENGTH: 108
<212> TYPE: PRT
<213> ORGANISM: Homo sapiens

<400> SEQUENCE: 32

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Phe Leu Ala Trp Tyr Gln Gln Lys Pro Gly Lys Val Pro Lys Leu Leu
        35                  40                  45

Val Phe Gly Ala Ser Ala Leu Gln Ser Gly Val Pro Ser Arg Phe Ser
50                  55                  60

Gly Ser Gly Ser Gly Thr Asp Phe Thr Leu Thr Ile Ser Gly Leu Gln
65                  70                  75                  80

Pro Glu Asp Val Ala Thr Tyr Tyr Cys Gln Lys Tyr Asn Gly Val Pro
                85                  90                  95

Leu Thr Phe Gly Gly Gly Thr Lys Val Glu Ile Lys
            100                 105

<210> SEQ ID NO 33
<211> LENGTH: 125
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Glu Met Phe Trp Val Arg Gln Ala Pro Gly Lys Gly Leu Glu Trp Val
        35                  40                  45

Ser Ser Ile Ser Pro Ser Gly Gly Gln Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Arg Thr Tyr Tyr Asp Phe Trp Ser Gly Tyr Gly Pro Leu
            100                 105                 110

Trp Tyr Trp Gly Gln Gly Thr Leu Val Thr Val Ser Ser
        115                 120                 125

<210> SEQ ID NO 34
<211> LENGTH: 113
<212> TYPE: PRT
<213> ORGANISM: Homo sapiens

<400> SEQUENCE: 34

Gln Asp Ile Gln Met Thr Gln Ser Pro Leu Ser Leu Pro Val Thr Leu
1               5                   10                  15

Gly Glu Ser Ala Ser Val Ser Cys Arg Ser Ser Gln Ser Leu Leu His
            20                  25                  30

Glu Asn Gly His Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ser Leu Lys Thr Pro Pro Thr Phe Gly Pro Gly Thr Lys Val Glu Ile
            100                 105                 110

Lys

<210> SEQ ID NO 35
<211> LENGTH: 125
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Ile Trp Val Arg Gln Ala Pro Gly Lys Gly Leu Glu Trp Val
        35                  40                  45

Ser Ser Ile Tyr Pro Ser Gly Gly Asn Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Val Leu Arg Tyr Phe Asp Trp Asp Ala Ser Gly Met
            100                 105                 110

Asp Val Trp Gly Gln Gly Thr Thr Val Thr Val Ser Ser
        115                 120                 125

<210> SEQ ID NO 36
<211> LENGTH: 108
<212> TYPE: PRT
<213> ORGANISM: Homo sapiens

<400> SEQUENCE: 36

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Asp Leu Gly Trp Tyr Gln Gln Lys Pro Gly Lys Ala Pro Lys Arg Leu
        35                  40                  45

Ile Tyr Val Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Trp Thr Phe Gly Gln Gly Thr Lys Val Glu Ile Lys
            100                 105

<210> SEQ ID NO 37
<211> LENGTH: 118
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Val Met His Trp Val Arg Gln Ala Pro Gly Lys Gly Leu Glu Trp Val
        35                  40                  45

```
Ser Ser Ile Ser Pro Ser Gly Gly Trp Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Met Ala Val Tyr Tyr Cys
                 85                  90                  95

Ala Arg Gly Thr Gly Ala Tyr Gly Met Asp Val Trp Gly Gln Gly Thr
                100                 105                 110

Thr Val Thr Val Ser Ser
            115

<210> SEQ ID NO 38
<211> LENGTH: 109
<212> TYPE: PRT
<213> ORGANISM: Homo sapiens

<400> SEQUENCE: 38

Gln Asp Ile Gln Met Thr Gln Ser Pro Gly Thr Leu Ser Leu Ser Pro
 1               5                  10                  15

Gly Asp Arg Ala Thr Leu Ser Cys Gly Ala Ser Gln Leu Val Val Ser
                20                  25                  30

Asn Tyr Ile Ala Trp Tyr Gln Gln Lys Pro Gly Gln Ala Pro Arg Leu
             35                  40                  45

Leu Met Tyr Ala Gly Ser Ile Arg Ala Thr Gly Ile Pro Asp Arg Phe
         50                  55                  60

Ser Gly Ser Gly Ser Gly Thr Asp Phe Thr Leu Thr Ile Ser Arg Leu
 65                  70                  75                  80

Glu Pro Glu Asp Phe Ala Ile Tyr Tyr Cys Gln Gln Arg Ser Asn Trp
                 85                  90                  95

Pro Trp Thr Phe Gly Gln Gly Thr Lys Val Glu Ile Lys
                100                 105

<210> SEQ ID NO 39
<211> LENGTH: 115
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
                20                  25                  30

Ser Met Asn Trp Val Arg Gln Ala Pro Gly Lys Gly Leu Glu Trp Val
             35                  40                  45

Ser Ser Ile Tyr Ser Ser Gly Ser Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Ala Phe Asp Ile Trp Gly Gln Gly Thr Met Val Thr
                100                 105                 110

Val Ser Ser
        115

<210> SEQ ID NO 40
```

<211> LENGTH: 109
<212> TYPE: PRT
<213> ORGANISM: Homo sapiens

<400> SEQUENCE: 40

Gln Asp Ile Gln Met Thr Gln Ser Pro Ser Ser Leu Ser Ala Phe Val
1               5                   10                  15

Gly Asp Lys Val Thr Ile Thr Cys Arg Ala Ser Gln Ser Val Gly Thr
            20                  25                  30

Tyr Leu Asn Trp Tyr Gln Gln Lys Ala Gly Lys Ala Pro Glu Leu Leu
        35                  40                  45

Ile Tyr Ala Thr Ser Asn Leu Arg Ser Gly Val Pro Ser Arg Phe Ser
50                  55                  60

Gly Ser Gly Ser Gly Thr Asp Phe Thr Leu Thr Ile Asn Thr Leu Gln
65                  70                  75                  80

Pro Glu Asp Phe Ala Thr Tyr Tyr Cys Gln Gln Ser Tyr Ser Ile Pro
                85                  90                  95

Arg Phe Thr Phe Gly Pro Gly Thr Lys Val Asp Ile Lys
            100                 105

<210> SEQ ID NO 41
<211> LENGTH: 119
<212> TYPE: PRT
<213> ORGANISM: Homo sapiens

<400> SEQUENCE: 41

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Lys Met Trp Trp Val Arg Gln Ala Pro Gly Lys Gly Leu Glu Trp Val
        35                  40                  45

Ser Gly Ile Arg Pro Ser Gly Gly Leu Thr Arg Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asp Tyr Val Gly Gly Phe Asp Tyr Trp Gly Gln Gly
            100                 105                 110

Thr Leu Val Thr Val Ser Ser
        115

<210> SEQ ID NO 42
<211> LENGTH: 108
<212> TYPE: PRT
<213> ORGANISM: Homo sapiens

<400> SEQUENCE: 42

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
50                  55                  60

```
Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln His Tyr Gly Gly Ser
             85                  90                  95

Gln Ala Phe Gly Gly Gly Thr Lys Val Glu Ile Lys
            100                 105
```

<210> SEQ ID NO 43
<211> LENGTH: 117
<212> TYPE: PRT
<213> ORGANISM: Homo sapiens

<400> SEQUENCE: 43

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Asn Met Gly Trp Val Arg Gln Ala Pro Gly Lys Gly Leu Glu Trp Val
         35                  40                  45

Ser Ser Ile Ser Ser Ser Gly Gly Tyr Thr Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Leu Tyr Arg Gly Phe Asp Tyr Trp Gly Gln Gly Thr Leu
            100                 105                 110

Val Thr Val Ser Ser
            115
```

<210> SEQ ID NO 44
<211> LENGTH: 109
<212> TYPE: PRT
<213> ORGANISM: Homo sapiens

<400> SEQUENCE: 44

```
Gln Asp Ile Gln Met Thr Gln Ser Pro Ala Thr Leu Ser Val Ser Pro
  1               5                  10                  15

Gly Glu Arg Ala Thr Leu Ser Cys Arg Ala Ser Glu Ser Val Lys Asn
             20                  25                  30

Asn Leu Ala Trp Tyr Gln Gln Lys Pro Gly Gln Ala Pro Arg Leu Leu
         35                  40                  45

Ile Tyr Gly Val Ser Thr Arg Ala Pro Gly Ile Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Arg Ser Asn Trp Pro
             85                  90                  95

Pro Val Thr Phe Gly Gln Gly Thr Arg Leu Glu Ile Lys
            100                 105
```

<210> SEQ ID NO 45
<211> LENGTH: 124
<212> TYPE: PRT
<213> ORGANISM: Homo sapiens

<400> SEQUENCE: 45

```
Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Tyr Tyr
                            20                  25                  30

Gly Met Tyr Trp Val Arg Gln Ala Pro Gly Lys Gly Leu Glu Trp Val
                        35                  40                  45

Ser Ser Ile Ser Ser Gly Gly Tyr Thr Asp Tyr Ala Asp Ser Val
                50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                            85                  90                  95

Ala Arg Arg Ile Lys Tyr Tyr Asp Ile Glu Gly Glu Gly Ala Phe Asp
                        100                 105                 110

Ile Trp Gly Gln Gly Thr Met Val Thr Val Ser Ser
                        115                 120

<210> SEQ ID NO 46
<211> LENGTH: 113
<212> TYPE: PRT
<213> ORGANISM: Homo sapiens

<400> SEQUENCE: 46

Gln Asp Ile Val Met Thr Gln Thr Pro Pro Ser Leu Pro Val Asn Pro
             1               5                   10                  15

Gly Glu Pro Ala Ser Ile Ser Cys Arg Ser Ser Gln Ser Leu Leu His
                            20                  25                  30

Arg Asn Gly Tyr Asn Tyr Leu Asp Trp Tyr Leu Gln Lys Pro Gly Gln
                        35                  40                  45

Ser Pro Gln Leu Leu Ile His Leu Gly Ser Tyr Arg Ala Ser Gly Val
                50                  55                  60

Pro Asp Arg Phe Ser Gly Ser Gly Ser Gly Thr Asp Phe Thr Leu Lys
             65                  70                  75                  80

Ile Ser Arg Val Glu Ala Glu Asp Val Gly Val Tyr Tyr Cys Met Gln
                            85                  90                  95

Pro Leu Gln Thr Pro Phe Thr Phe Gly Pro Gly Thr Lys Val Asp Ile
                        100                 105                 110

Lys

<210> SEQ ID NO 47
<211> LENGTH: 122
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser His Tyr
                            20                  25                  30

Val Met Phe Trp Val Arg Gln Ala Pro Gly Lys Gly Leu Glu Trp Val
                        35                  40                  45

Ser Arg Ile Val Pro Ser Gly Ala Thr Met Tyr Ala Asp Ser Val
                50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                            85                  90                  95
```

-continued

```
Ala Arg Asp Arg Pro Leu Tyr Asp Ser Ser Gly Tyr Val Asp Tyr Trp
            100                 105                 110

Gly Gln Gly Thr Leu Val Thr Val Ser Ser
            115                 120

<210> SEQ ID NO 48
<211> LENGTH: 111
<212> TYPE: PRT
<213> ORGANISM: Homo sapiens

<400> SEQUENCE: 48

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Asp Lys Ala Pro Lys Leu
            35                  40                  45

Ile Ile Tyr Asn Val Asn Glu Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Thr Ser Tyr Ala Gly Ser
                85                  90                  95

Asn Lys Ile Gly Val Ser Gly Thr Gly Thr Lys Val Thr Val Leu
            100                 105                 110

<210> SEQ ID NO 49
<211> LENGTH: 128
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
                20                  25                  30

Pro Met Phe Trp Val Arg Gln Ala Pro Gly Lys Gly Leu Glu Trp Val
            35                  40                  45

Ser Gly Ile Tyr Ser Ser Gly Pro Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Leu Gly Arg Tyr Tyr Asp Phe Trp Ser Gly Tyr Ser
            100                 105                 110

Tyr Gly Met Asp Val Trp Gly Gln Gly Thr Thr Val Thr Val Ser Ser
            115                 120                 125

<210> SEQ ID NO 50
<211> LENGTH: 105
<212> TYPE: PRT
<213> ORGANISM: Homo sapiens

<400> SEQUENCE: 50

Gln Asp Ile Gln Met Thr Gln Ser Pro Gly Thr Leu Ser Leu Ser Pro
1               5                   10                  15
```

Gly Glu Arg Ala Thr Leu Ser Cys Arg Ala Ser Gln Ser Val Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Ser Gly Val Thr Phe
                85                  90                  95

Gly Gly Gly Thr Lys Val Glu Ile Lys
            100                 105

<210> SEQ ID NO 51
<211> LENGTH: 115
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ser Met Asn Trp Val Arg Gln Ala Pro Gly Lys Gly Leu Glu Trp Val
        35                  40                  45

Ser Ser Ile Tyr Ser Ser Gly Gly Ser Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Phe Asp Ile Trp Gly Gln Gly Thr Met Val Thr
            100                 105                 110

Val Ser Ser
        115

<210> SEQ ID NO 52
<211> LENGTH: 108
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Tyr
            20                  25                  30

Leu Asn Trp Tyr Gln Gln Lys Pro Gly Lys Ala Pro Lys Leu Leu Ile
        35                  40                  45

Tyr Ala Thr Ser Asn Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Arg
                85                  90                  95

Phe Thr Phe Gly Pro Gly Thr Lys Val Asp Ile Lys
            100                 105

```
<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mca
<220> FEATURE:
<221> NAME/KEY: MOD_RES
<222> LOCATION: (4)..(4)
<223> OTHER INFORMATION: Cys(Mob)
<220> FEATURE:
<221> NAME/KEY: MOD_RES
<222> LOCATION: (8)..(8)
<223> OTHER INFORMATION: Dap(Dnp)
<220> FEATURE:
<223> OTHER INFORMATION: C-term NH2

<400> SEQUENCE: 53

Pro Leu Ala Cys Trp Ala Arg Xaa
1               5
```

COMBINATION THERAPY COMPRISING AN MMP-14 BINDING PROTEIN

CROSS REFERENCE TO RELATED APPLICATIONS

This application is a national phase application under 35 U.S.C. § 371 of International Application No. PCT/US2012/060791, filed Oct. 18, 2012, claims priority to U.S. Application Ser. No. 61/549,873, filed on Oct. 21, 2011. The disclosures of the prior applications are considered part of (and are incorporated by reference in) the disclosure of this application.

BACKGROUND

The membrane type (MT)—matrix metalloproteinases (MMPs) constitute a sub-group of membrane-anchored MMPs that are major mediators of pericellular proteolysis and physiological activators of pro-MMP-2. MT-MMPs activate the zymogenic form of MMP-2 (pro-MMP-2 or pro-gelatinase A) (Hernandez-Barrantes et al., 2002, *Semin. Cancer Biol*, 12:131-8; Zucker et al., 2003, *Curr Top Dev Biol*, 54: 1-74). MMP-2, in turn, can activate pro-MMP-9 (Toth et al., 2003, *Biochem Biophys Res Commun*, 308:386-95). The MT-MMPs comprise six members of plasma-tethered MMPs, which include four type I transmembrane enzymes (MMP-14, -15, -16, and -24) and two glycosyl-phosphatidylinositol-anchored enzymes (MMP-17, and -25) (Zhao et al., 2004, *J Biol Chem*, 279: 8592-8601). In addition to being potent extracellular matrix (ECM)-degrading enzymes, the type I transmembrane MT-MMPs can also initiate a cascade of zymogen activation on the cell surface.

SUMMARY

This disclosure relates, inter alia, to the use of proteins that bind MMP-14, herein referred to as "MMP-14 binding proteins," in combination with one or more agents for the treatment of cancer. Such MMP-14 binding proteins include antibodies and antibody fragments (e.g., primate antibodies and Fabs, especially human antibodies and Fabs) that bind to and/or inhibit MMP-14 (e.g., human MMP-14). The MMP-14 binding proteins can be used in the treatment of diseases, particularly human disease, such as cancer, in which excess or inappropriate activity of MMP-14 features. In many cases, the proteins have tolerable low or no toxicity.

In one aspect, the MMP-14 binding proteins used in the combination therapies described herein includes at least one immunoglobulin variable region. For example, the protein includes a heavy chain (HC) immunoglobulin variable domain sequence and a light chain (LC) immunoglobulin variable domain sequence. In one embodiment, the protein binds to and inhibits MMP-14, e.g., human MMP-14.

In one aspect, methods are provided for treating cancer, comprising administering an MMP-14 binding protein, optionally in combination with at least one additional agent. In some embodiments, the subject to be treated suffers from, or is suspected of having, melanoma, metastatic melanoma, pancreatic cancer, among others.

In one embodiment, the cancer is pancreatic cancer (e.g., advanced or metastatic pancreatic cancer).

In one embodiment, the pancreatic cancer is a chemotherapeutic sensitive, a chemotherapeutic refractory, a chemotherapeutic resistant, and/or a relapsed cancer. The pancreatic cancer can be, e.g., sensitive, refractory or resistant to treatment with an anti-metabolite, e.g., an antifolate (e.g., pemetrexed, floxuridine, raltitrexed) or pyrimidine analog (e.g., capecitabine, cytrarabine, gemcitabine, 5-fluorouracil). In one embodiment, the pancreatic cancer is sensitive, refractory or resistant to treatment with a pyrimidine analog such as, e.g., gemcitabine and/or 5-fluorouracil, and, e.g., the MMP-14 binding protein, e.g., an MMP-14 binding protein described herein, e.g., DX-2400, is administered as a single agent.

In one embodiment, the cancer is pancreatic cancer (e.g., advanced or metastatic pancreatic cancer) and the MMP-14 binding protein, e.g., an MMP-14 binding protein described herein, e.g., DX-2400, is administered in combination with at least one additional agent. In one embodiment, the MMP-14 binding protein is administered in combination with an anti-metabolite, e.g., an antifolate (e.g., pemetrexed, floxuridine, raltitrexed) or pyrimidine analog (e.g., capecitabine, cytrarabine, gemcitabine, 5-fluorouracil). In a preferred embodiment, the MMP-14 binding protein is administered in combination with gemcitabine and/or 5-fluorouracil. In one embodiment, the MMP-14 binding protein is administered in combination with gemcitabine, e.g., at a dose described herein. In some embodiments, the MMP-14 binding protein is also administered in combination with an additional therapy, e.g., such as radiation.

In one embodiment, the cancer is melanoma (e.g., advanced or metastatic melanoma).

In one embodiment, the melanoma is a chemotherapeutic sensitive, a chemotherapeutic refractory, a chemotherapeutic resistant, and/or a relapsed melanoma. The melanoma can be, e.g., sensitive, refractory or resistant to treatment with an alkylating agent (e.g., cyclophosphamide, dacarbazine, melphalan, ifosfamide, temozolomide), a taxane (e.g., docetaxel, paclitaxel, larotaxel, cabazitaxel) and/or an interleukin (e.g., interleukin-2). In one embodiment, the melanoma is sensitive, refractory or resistant to treatment with an alkylating agent such as, e.g., dacarbazine and, e.g., the MMP-14 binding protein, e.g., an MMP-14 binding protein described herein, e.g., DX-2400, is administered as a single agent. In one embodiment, the melanoma is sensitive, refractory or resistant to treatment with a taxane such as, e.g., paclitaxel and, e.g., the MMP-14 binding protein, e.g., an MMP-14 binding protein described herein, e.g., DX-2400, is administered as a single agent.

In one embodiment, the cancer is melanoma (e.g., advanced or metastatic melanoma) and the MMP-14 binding protein, e.g., an MMP-14 binding protein described herein, e.g., DX-2400, is administered in combination with at least one additional agent. In one embodiment, the MMP-14 binding protein is administered in combination with an alkylating agent (e.g., cyclophosphamide, dacarbazine, melphalan, ifosfamide, temozolomide). In a preferred embodiment, the MMP-14 binding protein is administered in combination with dacarbazine. In one embodiment, the MMP-14 binding protein is administered in combination with dacarbazine, e.g., at a dose described herein. In one embodiment, the MMP-14 binding protein is administered in combination with a taxane (e.g., docetaxel, paclitaxel, larotaxel, cabazitaxel). In a preferred embodiment, the MMP-14 binding protein is administered in combination with paclitaxel. In one embodiment, the MMP-14 binding protein is administered in combination with paclitaxel, e.g., at a dose described herein. In some embodiments, the MMP-14 binding protein is also administered in combination with an additional therapy, e.g., such as radiation.

In some embodiments the MMP-14 binding protein can include one or more of the following characteristics: (a) a human CDR or human framework region; (b) the HC immunoglobulin variable domain sequence comprises one or more CDRs that are at least 85, 88, 90, 92, 94, 95, 96, 97, 98, 99, or 100% identical to a CDR of a LC variable domain described herein; (c) the LC immunoglobulin variable domain sequence comprises one or more CDRs that are at least 85, 88, 90, 92, 94, 95, 96, 97, 98, 99, or 100% identical to a CDR of a HC variable domain described herein; (d) the LC immunoglobulin variable domain sequence is at least 85, 88, 90, 92, 94, 95, 96, 97, 98, 99, or 100% identical to a LC variable domain described herein; (e) the HC immunoglobulin variable domain sequence is at least 85, 88, 90, 92, 94, 95, 96, 97, 98, 99, or 100% identical to a HC variable domain described herein; (f) the protein binds an epitope bound by a protein described herein, or an epitope that overlaps with such epitope; and (g) a primate CDR or primate framework region.

The MMP-14 binding protein can bind to MMP-14, e.g., human MMP-14, with a binding affinity of at least $10^5$, $10^6$, $10^7$, $10^8$, $10^9$, $10^{10}$ and $10^{11}$ M$^{-1}$. In one embodiment, the protein binds to MMP-14 with a $K_{off}$ slower than $1\times10^{-3}$, $5\times10^{-4}$ s$^{-1}$, or $1\times10^{-4}$ s$^{-1}$. In one embodiment, the protein binds to MMP-14 with a $K_{on}$ faster than $1\times10^2$, $1\times10^3$, or $5\times10^3$ M$^{-1}$ s$^{-1}$. In one embodiment, the protein inhibits human MMP-14 activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. For example, the protein modulates MMP-14 binding to proMMP-2, e.g., by inhibiting activation of proMMP-2. The protein may inhibit MMP-14 activation of pro-MMP2 in vitro in PMA-activated HT-1080 cells. The affinity of the protein for MMP-14 can be characterized by a $K_D$ of less than 100 nm, less than 10 nM, or less than 2.4 nM.

In one embodiment, the protein binds the catalytic domain of human MMP-14, e.g., the protein contacts residues in or near the active site of MMP-14.

In a preferred embodiment, the MMP-14 binding protein is a human antibody having the light and heavy chains of antibodies picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In one embodiment the protein is a human antibody having the light and heavy chains of antibody M0038-F01, also referred to herein as DX-2400. In a preferred embodiment, the protein is a human antibody having its heavy chain picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having its light chain picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having one or more heavy chain CDRs picked from the corresponding CDRs of the list of heavy chains comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having one or more light chain CDRs picked from the corresponding CDRs of the list of heavy chains comprising M0031-C02, M0031-F01, M0033-H07, M0037-C09, M0037-D01, M0038-E06, M0038-F01, M0038-F08, M0039-H08, M0040-A06, M0040-A11, and M0043-G02.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab. In other implementations, the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the MMP-14 binding protein is a human or humanized antibody or is non-immunogenic in a human. For example, the protein includes one or more human antibody framework regions, e.g., all human framework regions. In one embodiment, the protein includes a human Fc domain, or an Fc domain that is at least 95, 96, 97, 98, or 99% identical to a human Fc domain.

In one embodiment, the MMP-14 binding protein is a primate or primatized antibody or is non-immunogenic in a human. For example, the protein includes one or more primate antibody framework regions, e.g., all primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In some embodiments, the affinity of the primate antibody for MMP-14 is characterized by a $K_D$ of less than 1.2 nM.

In certain embodiments, the protein includes no sequences from mice or rabbits (e.g., is not a murine or rabbit antibody).

In one embodiment, the protein is capable of binding to tumor cells expressing MMP-14, e.g., to HT-1080 (a human fibrosarcoma cell line), LNCaP (human prostate carcinoma), PAM527 (human pancreatic cancer), Panc-1 (human pancreatic cancer), MDA-MB-231 (human, Caucasian, breast, adenocarcinoma), A375 (human melanoma), SK-MEL-5 (human melanoma), or PC3 (Human prostatic cancer cells) cells.

In some embodiments, a subject to be treated, e.g., with a combination therapy described herein, is first tested for MMP-14 expression prior to initiation of treatment. In some embodiments, MMP-14 is tested in a sample by e.g., contacting the sample with an MMP-14 binding protein; and detecting an interaction between the protein and the MMP-14, if present. In some embodiments, the MMP-14 binding protein includes a detectable label. In some embodiments, the MMP-14 binding protein can be used to detect MMP-14 in situ in a subject. For example, a subject is administered an MMP-14 binding protein, and the protein is detected in the subject; that is the detecting comprises imaging the subject.

In another aspect, the disclosure features a combination therapy including an MMP-14 binding protein that modulates MMP-14 activity, e.g., an MMP-14 binding protein described herein, e.g., DX-2400, and one or more additional agents for the treatment of the disease or disorder, e.g., melanoma, pancreatic cancer. In one embodiment, the combination therapy includes an MMP-14 binding protein, e.g., an MMP-14 binding protein described herein, e.g., DX-2400, and an anti-metabolite, e.g., an antifolate (e.g., pemetrexed, floxuridine, raltitrexed) or pyrimidine analog (e.g., capecitabine, cytrarabine, gemcitabine, 5-fluorouracil)

for the treatment of cancer, e.g., pancreatic cancer (e.g., advanced or metastatic pancreatic cancer). In one embodiment, the combination therapy includes an MMP-14 binding protein, e.g., an MMP-14 binding protein described herein, e.g., DX-2400, and an alkylating agent (e.g., cyclophosphamide, dacarbazine, melphalan, ifosfamide, temozolomide) for the treatment of cancer, e.g., melanoma (e.g., advanced or metastatic melanoma). In one embodiment, the combination therapy includes an MMP-14 binding protein, e.g., an MMP-14 binding protein described herein, e.g., DX-2400, and a taxane (e.g., docetaxel, paclitaxel, larotaxel, cabazitaxel) for the treatment of cancer, e.g., melanoma (e.g., advanced or metastatic melanoma).

In another aspect, the disclosure features a method of treating cancer (e.g., metastatic cancer). The method includes: administering, to a subject, an MMP-14 binding protein in combination with one or more additional agents (e.g., anti-cancer agents) in an amount sufficient to treat a cancer in the subject. For example, the cancer is metastatic cancer, e.g., metastatic melanoma or pancreatic cancer.

MMP-14 binding proteins are useful to modulate metastatic activity in a subject. The protein can be administered, to the subject, an MMP-14 binding protein in an amount effective to modulate metastatic activity. For example, the protein inhibits one or more of: tumor growth, tumor embolism, tumor mobility, tumor invasiveness, and cancer cell proliferation.

The methods disclosed herein relate to the treatment cancer (e.g., treating cancer and/or modulation of metastatic activity) with a combination of an MMP-14 binding protein and one or more additional agents (e.g., 1, 2, 3, 4, 5, or 6 additional agents). In some embodiments, the one or more additional therapies include an anti-cancer therapy, e.g., administration of a chemotherapeutic, e.g., an alkylating agent (e.g., cyclophosphamide, dacarbazine, melphalan, ifosfamide, temozolomide), a taxane (e.g., docetaxel, paclitaxel, larotaxel, cabazitaxel), an anti-metabolite, e.g., an antifolate (e.g., pemetrexed, floxuridine, raltitrexed) or pyrimidine analog (e.g., capecitabine, cytrarabine, gemcitabine, 5-fluorouracil), a platinum-based agent (e.g., cisplatin, carboplatin, oxaliplatin), an EGF receptor inhibitor (e.g., cetuximab, erlotinib, gefitinib). Essentially any anti-cancer therapy known to those of skill in the art can be combined with an MMP-14 inhibitor for the treatment of cancer. In some embodiments, the cancer is pancreatic cancer and the one or more additional therapies include gemcitabine, 5-FU, leucovorin, an EGF receptor inhibitor (e.g., erlotinib), and/or a platinum based agent (e.g., cisplatin or oxaliplatin). In some embodiments, the cancer is melanoma and the one or more additional therapies include dacarbazine, temozolomide, a platinum based agent (e.g., cisplatin or carboplatin), paclitaxel and/or an interleukin (e.g., interleukin-2).

MMP-14 binding proteins are useful for targeted delivery of an agent to a subject (e.g., a subject who has or is suspected of having a tumor), e.g., to direct the agent to a tumor in the subject. For example, an MMP-14 binding protein that is coupled to an anti-tumor agent (such as a chemotherapeutic, toxin, drug, or a radionuclide (e.g., $^{131}$I, $^{90}$Y, $^{177}$Lu)) can be administered to a subject who has or is suspected of having a tumor.

In another aspect, the subject is first identified as a candidate for MMP-14 therapy, e.g., MMP-14 combination therapy, by e.g., imaging a subject. For example, an MMP-14 antibody having a detectable label can be administered to a subject to determine the level and/or location of MMP-14 expression. In some embodiments, the protein is one that does not substantially inhibit MMP-14 catalytic activity. The MMP-14 binding protein may include a detectable label (e.g., a radionuclide or an MRI-detectable label). In one embodiment, the subject has or is suspected of having a tumor. The method is useful for cancer diagnosis, intraoperative tumor detection, post-operative tumor detection, or monitoring tumor invasive activity.

In one aspect, the disclosure features the use of an MMP-14 binding protein described herein for the manufacture of a medicament for the treatment of a disorder described herein, e.g., a cancer (e.g., metastatic cancer, e.g., metastatic melanoma or pancreatic cancer), or inappropriate angiogenesis. The MMP-14 binding proteins and, optionally the combination therapies, described herein can be used.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
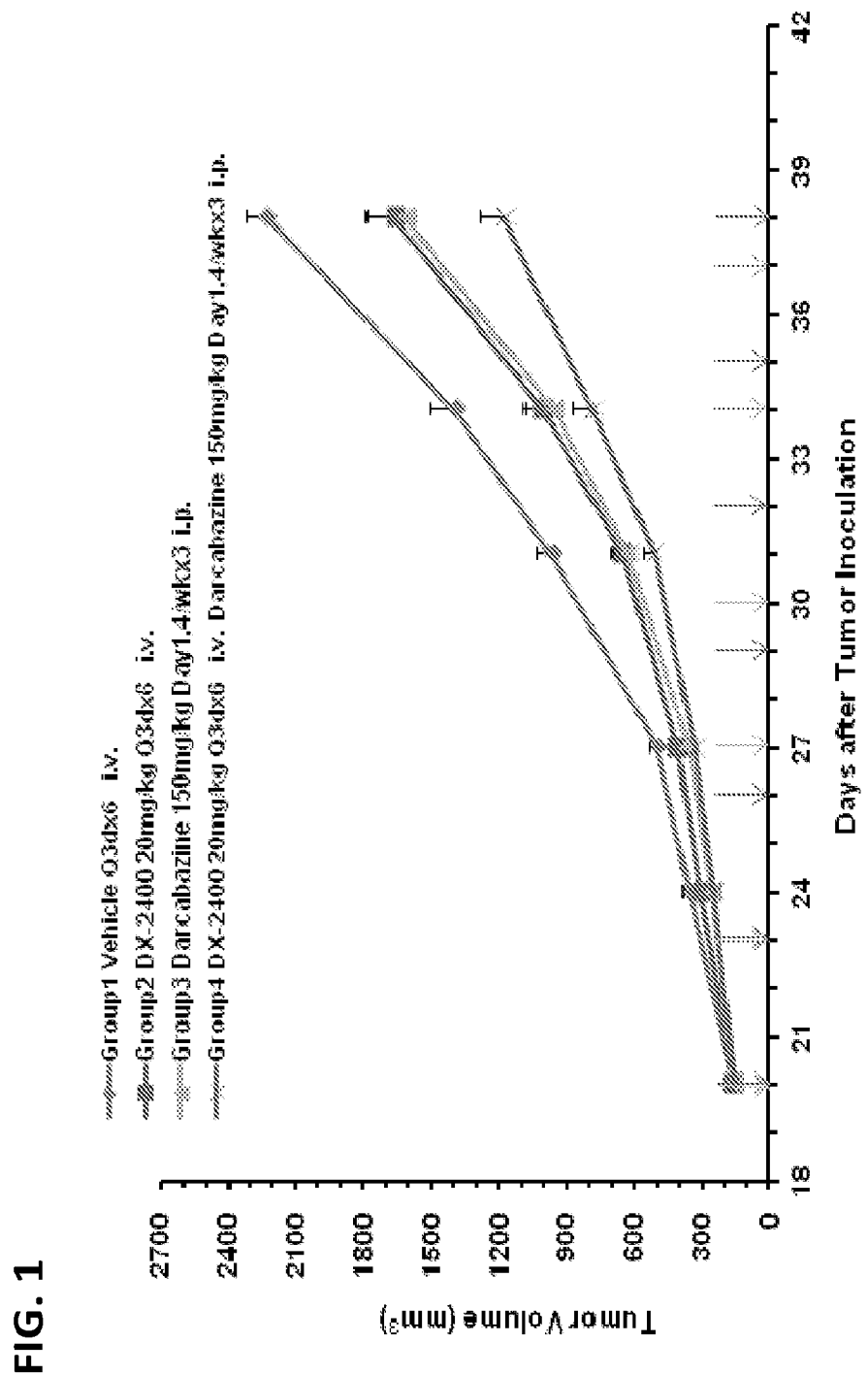
FIG. 1 is a graph showing the effect of anti-cancer treatment on tumor volume in a xenograft mouse model of human melanoma (A375 cells). Animals were treated with DX-2400 alone, darcabazine alone, and a combination of darcabazine and DX-2400.

The methods and compositions relating to combination therapy with an MMP-14 inhibitor and one or more additional agents were discovered, in part, by the observation that such combination therapies reduced tumor volume and tumor growth to a greater degree in a mouse xenograft model of human metastatic melanoma and human pancreatic cancer than either agent alone. Thus, provided herein are methods and compositions for treating cancer, e.g., melanoma or pancreatic cancer, comprising an MMP-14 inhibitor, optionally, in combination with one or more additional agents e.g., anti-cancer agents.

Matrix Metalloproteinase-14

MMP-14 is encoded by a gene designated as MMP14, matrix metalloproteinase-14 precursor. Synonyms for MMP-14 include matrix metalloproteinase 14 (membrane-inserted), membrane-type-1 matrix metalloproteinase, membrane-type matrix metalloproteinase 1, MMP-14, MMP-X1, MT1MMP, MT1-MMP, MTMMP1, MT-MMP 1.

MT-MMPs have similar structures, including a signal peptide, a prodomain, a catalytic domain, a hinge region, and a hemopexin domain (Wang, et al., 2004, *J Biol Chem*, 279:51148-55). According to SwissProt entry P50281, the signal sequence of MMP-14 precursor includes amino acid residues 1-20. The pro-peptide includes residues 21-111. Cys93 is annotated as a possible cysteine switch. Residues 112 through 582 make up the mature, active protein. The catalytic domain includes residues 112-317. The hemopexin domain includes residues 318-523. The transmembrane segment comprises residues 542 through 562.

MMP-14 can be shed from cells or found on the surface of cells, tethered by a single transmembrane amino-acid sequence. See, e.g., Osnkowski et al. (2004, *J Cell Physiol*, 200:2-10).

An exemplary amino acid sequence of human MMP14 is shown in Table 1:

TABLE 1

Amino-acid sequence of human MMP14

(SEQ ID NO: 2; Genbank Accession No. CAA88372.1)
MSPAPRPPRCLLLPLLTLGTALASLGSAQSSSFSPEAWLQQYGYLPP

GDLRTHTQRSPQSLSAAIAAMQKFYGLQVTGKADADTMKAMRRPRCG

VPDKFGAEIKANVRRKRYAIQGLKWQHNEITFCIQNYTPKVGEYATY

EAIRKAFRVWESATPLRFREVPYAYIREGHEKQADIMIFFAEGFHGD

STPFDGEGGFLAHAYFPGPNIGGDTHFDSAEPWTVRNEDLNGNDIFL

VAVHELGHALGLEHSSDPSAIMAPFYQWMDTENFVLPDDDRRGIQQL

YGGESGFPTKMPPQPRTTSRPSVPDKPKNPTYGPNICDGNFDTVAML

RGEMFVFKERWFWRVRNNQVMDGYPMPIGQFWRGLPASINTAYERKD

GKFVFFKGDKHWVFDEASLEPGYPKHIKELGRGLPTDKIDAALFWMP

NGKTYFFRGNKYYRFNEELRAVDSEYPKNIKVWEGIPESPRGSFMGS

DEVFTYFYKGNKYWKFNNQKLKVEPGYPKSALRDWMGCPSGGRPDEG

TEEETEVIIIEVDEEGGGAVSAAAVVLPVLLLLLVLAVGLAVFFFRR

HGTPRRLLYCQRSLLDKV.

An exemplary amino acid sequence of mouse MMP14 is shown in Table 2.

TABLE 2

Amino-acid sequence of mouse MMP14

SEQ ID NO: 4; GenBank Accession No. NP_032634.2
MSPAPRPSRSLLLPLLTLGTALASLGWAQGSNFSPEAWLQQYGYLPPG

DLRTHTQRSPQSLSAAIAAMQKFYGLQVTGKADLATMMAMRRPRCGVP

DKFGTEIKANVRRKRYAIQGLKWQHNEITFCIQNYTPKVGEYATFEAI

RKAFRVWESATPLRFREVPYAYIREGHEKQADIMILFAEGFHGDSTPF

DGEGGFLAHAYFPGPNIGGDTHFDSAEPWTVQNEDLNGNDIFLVAVHE

LGHALGLEHSNDPSAIMSPFYQWMDTENFVLPDDDRRGIQQLYGSKSG

SPTKMPPQPRTTSRPSVPDKPKNPAYGPNICDGNFDTVAMLRGEMFVF

KERWFWRVRNNQVMDGYPMPIGQFWRGLPASINTAYERKDGKFVFFKG

DKHWVFDEASLEPGYPKHIKELGRGLPTDKIDAALFWMPNGKTYFFRG

NKYYRFNEEFRAVDSEYPKNIKVWEGIPESPRGSFMGSDEVFTYFYKG

NKYWKFNNQKLKVEPGYPKSALRDWMGCPSGRRPDEGTEEETEVIIIE

TABLE 2-continued

Amino-acid sequence of mouse MMP14

VDEEGSGAVSAAAVVLPVLLLLLVLAVGLAVFFFRRHGTPKRLLYCQR

SLLDKV.

An exemplary MMP-14 protein can include the human or mouse MMP-14 amino acid sequence, a sequence that is 80%, 85%, 90%, 95%, 96%, 97%, 98%, or 99% identical to one of these sequences, or a fragment thereof, e.g., a fragment without the signal sequence or prodomain.

Human MMP-14 and murine MMP-14 sequences are identical at 558 of 580 positions, comprising about 96.2% identity. Despite a relatively high degree of similarity, their activity toward different substrates, including proMMP-2 and type I collagen, varies (Wang, et al., 2004, *J Biol Chem*, 279:51148-55).

MMP-14 in Cancer:

MMP-14-deficient mice were generated by gene targeting (Holmbeck, et al., 1999, *Cell*, 99:81-92). The expression of MMP-14 and its role in tumors is reviewed in Sato et al. (Sato, et al., 2005, *Cancer Sci*, 96:212-7), Zucker et al. (Zucker and Vacirca, 2004, *Cancer Metastasis Rev*, 23:101-17), and Bauvois (Bauvois, 2004, *Oncogene*, 23:317-29). Increased expression of MT-MMPs has previously been reported to correlate with increasing grade of malignancy in gliomas, a relationship shared with alterations in epidermal growth factor receptor (EGFR) signaling. One mechanism of EGFR-mediated invasiveness in gliomas may involve the induction of MT1-MMP (Van metter et al., 2004, *Neuro-oncol.*, 6(3):188-99).

MMP-14 is regulated by chemokines monocyte-chemoattractant protein-1/cc12 and interleukin-8/CXCL8 in endothelial cells during angiogenesis (Galvez et al, 2005, J Biol Chem, 280(2):1292-8). MMP-14 activity is also regulated by ERK 1/2- and p38 MAPK-modulated TIMP-2 expression which controls TGF-beta1-induced pericellular collagenolysis (Munshi et al., 2004, *J Biol Chem*, 279(37): 39042-50). Blockade of the ERK pathway suppresses the expression of MMP-3, -9, and -14, and CD44 and markedly inhibits the invasiveness of tumor cells (Tanimura et al., 2003, *Biochem Biophys Res Commun*, 304(4):801-6).

During angiogenesis, MMP-14 contributes to the specific up-regulation of VEGF-A through activation of Src tyrosine kinase pathways perhaps involving the cleavage of CD44 (Sounni et al., 2004, *J Biol Chem*, 279(14):13564-74).

MMP-14 has a number of endogenous inhibitors. TIMP-2 binds MMP-14 and anchors MMP-14 to cell surface and acts as a "receptor" for proMMP-2 (progelatinase A), such that the latter can be activated efficiently in a localized fashion (Murphy, et al., 2003, *Biochem Soc Symp*, 65-80). TIMP-2, TIMP-3, and TIMP-4 inhibit MMP-14, but TIMP-1 does not (Lee, et al., 2003, *J Biol Chem*, 278:40224-30). TIMPs typically are slow, tight binding inhibitors.

MMP-14 activates pro-MMP-2 causing a cascade of proteolysis that facilitates the mobility and invasiveness of tumor cells (Berno, et al., 2005, *Endocr Relat Cancer*, 12:393-406; Anilkumar, et al., 2005, Faseb J, 19:1326-8; Itoh and Seiki, 2005, J Cell Physiol; Lopez de Cicco, et al., 2005, *Cancer Res*, 65:4162-71; El Bedoui, et al., 2005, *Cardiovasc Res*, 67:317-25; Cao, et al., 2005, *Thromb Haemost*, 93:770-8; Sato, et al., 2005, *Cancer Sci*, 96:212-7; Dong, et al., 2005, *Am J Pathol*, 166:1173-86; Philip, et al., 2004, *Glycoconj J*, 21:429-41; Guo, et al., 2005, *Am J Pathol*, 166:877-90; Grossman, 2005, *Urol Oncol*, 23:222;

Gilles, et al., 2001, *J Cell Sci*, 114:2967-76). Studies propose that this activation process requires both active MT1-MMP and the TIMP-2-bound MT1-MMP (Strongin et al., 1995, *J Biol Chem*, 270, 5331-5338; Butler et al., 1998, *J Biol Chem*, 273: 871-80; Kinoshita et al., 1998, *J Biol Chem*, 273, 16098-103). The TIMP-2 in the latter complex binds, through its C-terminal domain, to the hemopexin domain of pro-MMP-2, which may localize the zymogen close to the active MT1-MMP (Butler et al., 1998, *J Biol Chem*, 273: 871-80; Kinoshita et al., 1998, *J Biol Chem.* 273(26):16098-103.).

In addition to proMMP-2, MMP-14 cleaves other substrates, such as collagen triple-helical structure (Minond, et al., 2004, *Biochemistry*, 43:11474-81), fibrin (Kluft, 2003, *Pathophysiol Haemost Thromb*, 33:425-9), Matrigel (Cao, et al., 2005, *Thromb Haemost*, 93:770-8), other extracellular matrix components (Sato, et al., 2005, *Cancer Sci*, 96:212-7), CD44 (Suenaga, et al., 2005, *Oncogene*, 24:859-68), and various other proteins (Hwang, et al., 2004, *Biochim Biophys Acta*, 1702:79-87). MMP-14 can promote the activation of pro-collagenase 2 and -3, a potent collagenolytic protease (Knauper et al., 1996, *J Biol Chem*, 271:17124-31; Woessner et Nagase, 2000).

MMP-14 has been implicated in many disease states, including, e.g., tumor growth (Trisciuoglio, et al., 2005, *J Cell Physiol*), tumor embolism (Cao, et al., 1996, *J Biol Chem*, 271:30174-80), angiogenesis (Haas, 2005, *Can J Physiol Pharmacol*, 83:1-7; (Handsley and Edwards, 2005, *Int J Cancer*, 115:849-60; (Roebuck, et al., 2005, *Am J Clin Pathol*, 123:405-14; (Pilorget, et al., 2005, *J Cereb Blood Flow Metab*, 25(9):1171-82), and cell proliferation (Aoki, et al., 2005, *J Biochem (Tokyo)*, 137:95-9). Accordingly, proteins that bind and/or inhibit MMP-14 can be used to treat and/or diagnose these conditions.

The role of MMPs in development, normal processes, and cancer is reviewed in Folgueras et al., *Int. J. Dev. Biol.* 48:411-424 (2004). Accordingly, therapies comprising proteins that bind and/or inhibit MMP-14 are useful to treat these conditions.

MMP-14 Binding Proteins

Definitions

The term "binding protein" refers to a protein that can interact with a target molecule. This term is used interchangeably with "ligand." An "MMP-14 binding protein" refers to a protein that can interact with MMP-14, and includes, in particular, proteins that preferentially interact with and/or inhibit MMP-14. For example, the MMP-14 binding protein is an antibody.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., *Eur J Immunol.* 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with an MMP-14 protein, e.g., the MMP-14 catalytic domain.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and U.S. Pat. No. 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ M$^{-1}$ for a particular target molecule, e.g., MMP-14. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM CaCl$_2$ at pH 7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N\cdot[Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An MMP-14 binding protein may have mutations (e.g., at least one, two, or four, and/or less than 15, 10, 5, or 3) relative to a binding protein described herein (e.g., a conservative or non-essential amino acid substitutions), which do not have a substantial effect on protein function. Whether or not a particular substitution will be tolerated, i.e., will not adversely affect biological properties, such as binding activity can be predicted, e.g., by evaluating whether the mutation is conservative or by the method of Bowie, et al. (1990) *Science* 247:1306-1310.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Motif sequences for biopolymers can include positions which can be varied amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

The term "cognate ligand" refers to a naturally occurring ligand of an MMP-14, including naturally occurring variants thereof (e.g., splice variants, naturally occurring mutants, and isoforms).

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

Exemplary MMP-14 Binding Proteins:

The disclosure provides exemplary proteins that bind to MMP-14 (e.g., human MMP-14) and include at least one immunoglobin variable region. Additional examples of MMP-14 binding proteins can be found in e.g., U.S. Pat. No. 7,745,587, which is herein incorporated by reference in its entirety.

In some embodiments, MMP-14 binding proteins may be antibodies. MMP-14 binding antibodies may have their HC and LC variable domain sequences included in a single polypeptide (e.g., scFv), or on different polypeptides (e.g., IgG or Fab). The MMP-14 binding protein may be an isolated protein (e.g., at least 70, 80, 90, 95, or 99% free of other proteins).

The MMP-14 binding protein may additionally inhibit MMP-14, e.g., human MMP-14. In one embodiment, the protein binds the catalytic domain of human MMP-14, e.g., the protein contacts residues in or near the active site of MMP-14.

Exemplary MMP-14 binding proteins for use in combination therapy for treating, e.g., cancer are known in the art, e.g., U.S. Pat. No. 7,745,587, and/or are described herein. Sequences the variable light chain (LV) and variable heavy chain (HV) for exemplary MMP-14 binding proteins M0031-C02, M0031-F01, M0033-H07, M0037-C09, M0037-D01, M0038-E06, M0038-F01, M0038-F08, M0039-H08, M0040-A06, M0040-A11, and M0043-G02 are provided herein.

```
> M0031-C02 LV
                                           (SEQ ID NO: 1)
CAA GAC ATC CAG ATG ACC CAG TCT CCA CTC TCC CTG

CCC GTC ACC CCT GGA GAG CCG GCC TCC ATC TCC TGC

AGG TCT AGT CAG AGC CTC CTG CAT AGT AAT GGA TAC

TAC TAT TTG GAT TGG TAC CTG CAG AAG CCA GGG CAG

TCT CCA CAA CTC CTG ATC TAT TTG GGT TCT TAT CGG

GCC TCC GGG GTC CCT GAC AGG TTC AGT GGC AGT GGA

TCA GGC ACA GAT TTT ACA CTG AAA ATC AGC AGT GTG

GAG GCT GAA GAT GTT GGG GTT TAT TAC TGC ATG CAA

GCT CTA CAA ACT CCT CTC ACT TTC GGC GGA GGG ACC

AGG GTG GAC ATC AAA

> M0031-C02 HV
                                           (SEQ ID NO: 3)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CCT TAC CCT ATG GGT TGG

GTT CGC CAA GCT CCT GGT AAA GGT TTG GAG TGG GTT

TCT TCT ATC GTT TCT TCT GGT GGC CTT ACT CTT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACT GCC GTG TAT TAC TGT

GCG AGA GGG GGA CGG CTT TAC GAT ATT TTG ACT GGT

CAA GGG GCC CCG TTT GAC TAC TGG GGC CAG GGA ACC

CTG GTC ACC GTC TCA AGC

> M0031-F01 LV
                                           (SEQ ID NO: 5)
CAG AGC GAA TTG ACT CAG CCA CCC TCA GTG TCT GGG

ACC CCC GGG CAG AGG GTC ACC ATC TCT TGT TCT GGA

ACC AGC GCC AAC ATC GGA CGT AAT GCT GTA CAC TGG

TAC CAG CAG CTC CCA GGA ACG GCC CCC AAA CTC CTC

ATT CAT AGT AAT AAC CGG CGG CCC TCA GGG GTC CCT

GAC CGA TTC TCT GGC TCC AAG TCT GGC ACC TCA GCC

TCC CTG GCC ATC AGT GGG CTC CAG TCT GAG GAT GAG

GCT GAT TAT TAC TGT GCA GCA TGG GAG AAC AGC CTG

AAT GCC TTT TAT GTC TTC GGA ACT GGG ACC AAG GTC

ACC GTC CTA

> M0031-F01 HV
                                           (SEQ ID NO: 6)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT ACT TAC GAG ATG CAT TGG

GTT CGC CAA GCT CCT GGT AAA GGT TTG GAG TGG GTT

TCT TCT ATC TAT TCT TCT GGT GGC TGG ACT GGT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCG AGA TCT CAA CAG TAT TAC GAT TTT TCC TCT CGC

TAC TAC GGC ATG GAC GTC TGG GGC CAA GGG ACC ACG

GTC ACC GTC TCA AGC

> M0033-H07 LV
                                           (SEQ ID NO: 7)
CAA GAC ATC CAG ATG ACC CAG TCT CCA TCC TCC CTG

TCT GCA TCT GTA GGA GAC AGA GTC ACC ATC ACT TGC

CGG GCG AGT CAG GGC ATT AGG AAT TTT TTA GCC TGG

TAT CAG CAG AAA CCA GGG AAA GTT CCT AAG CTC CTG

GTC TTT GGT GCA TCC GCT TTG CAA TCG GGG GTC CCA

TCT CGG TTC AGT GGC AGT GGA TCT GGG ACA GAT TTC

ACT CTC ACC ATC AGC GGC CTG CAG CCT GAG GAT GTT

GCA ACT TAT TAC TGT CAA AAG TAT AAC GGT GTC CCG

CTC ACT TTC GGC GGA GGG ACC AAG GTG GAG ATC AAA

> M0033-H07 HV
                                           (SEQ ID NO: 8)
GAA GTT CAA TTG TTA GAG TCT GGT GGC GGT CTT GTT

CAG CCT GGT GGT TCT TTA CGT CTT TCT TGC GCT GCT
```

-continued

TCC GGA TTC ACT TTC TCT GTT TAC GGT ATG GTT TGG

GTT CGC CAA GCT CCT GGT AAA GGT TTG GAG TGG GTT

TCT GTT ATC TCT TCT TCT GGT GGC TCT ACT TGG TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACC GCC TTG TAT TAC TGT

GCG AGA CCG TTC AGT AGA AGA TAC GGC GTC TTT GAC

TAC TGG GGC CAG GGC ACC CTG GTC ACC GTC TCA AGC

> M0037-C09 LV
(SEQ ID NO: 9)

CAA GAC ATC CAG ATG ACC CAG TCT CCA CTC TCC CTG

CCC GTC ACC CTT GGA GAG TCG GCC TCC GTC TCC TGC

AGG TCT AGT CAG AGC CTC CTT CAT GAA AAT GGA CAC

AAC TAT TTG GAT TGG TAC CTG CAG AAG CCA GGG CAG

TCT CCA CAG CTC CTG ATC TAT TTG GGT TCT AAT CGG

GCC TCC GGG GTC CCT GAC AGG TTC AGT GGC AGT GGA

TCA GGC ACA GAT TTT ACA CTG AAA ATC AGC AGA GTG

GAG GCT GAG GAT GTT GGG GTT TAT TAC TGC ATG CAA

TCT CTA AAG ACT CCT CCG ACG TTC GGC CCA GGG ACC

AAG GTG GAA ATC AAA

> M0037-C09 HV
(SEQ ID NO: 10)

GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CAT TAC GAG ATG TTT TGG

GTT CGC CAA GCT CCT GGT AAA GGT TTG GAG TGG GTT

TCT TCT ATC TCT CCT TCT GGT GGC CAG ACT CAT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACT GCC GTG TAT TAC TGT

GCC ACA GAT CGG ACG TAT TAC GAT TTT TGG AGT GGT

TAT GGG CCC CTG TGG TAC TGG GGC CAG GGA ACC CTG

GTC ACC GTC TCA AGC

> M0037-D01 LV
(SEQ ID NO: 11)

CAA GAC ATC CAG ATG ACC CAG TCT CCA TCC TCC CTG

TCT GCA TCT GTC GGA GAC AGA GTC ACC ATC ACT TGC

CGG GCA AGT CAG GGC ATT AGA AAT GAT TTA GGC TGG

TAT CAG CAG AAA CCA GGG AAA GCC CCT AAG CGC CTG

ATC TAT GTT GCA TCC AGT TTG CAA AGT GGG GTC CCA

TCA AGG TTC AGC GGC AGT GGA TCT GGG ACA GAA TTC

ACT CTC ACA ATC AGC AGC CTG CAG CCT GAA GAT TTT

GCA ACT TAT TAC TGT CTA CAG CAT AAT AGT TAC CCG

TGG ACG TTC GGC CAA GGG ACC AAG GTG GAA ATC AAA

> M0037-D01 HV
(SEQ ID NO: 12)

GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT ATG TAC ATG ATG ATT TGG

GTT CGC CAA GCT CCT GGT AAA GGT TTG GAG TGG GTT

TCT TCT ATC TAT CCT TCT GGT GGC AAT ACT ATG TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCC ACA GGT GTA TTA CGA TAT TTT GAC TGG GAT GCT

GGG AGC GGT ATG GAC GTC TGG GGC CAA GGG ACC ACG

GTC ACC GTC TCA AGC

> M0038-E06 LV
(SEQ ID NO: 13)

CAA GAC ATC CAG ATG ACC CAG TCT CCA GGC ACC CTG

TCC TTG TCT CCA GGG GAC AGA GCC ACC CTC TCC TGC

GGG GCC AGC CAG CTT GTT GTC AGC AAC TAC ATA GCC

TGG TAC CAG CAA AAA CCT GGC CAG GCT CCC AGA CTC

CTC ATG TAT GCT GGA TCC ATC AGG GCC ACT GGC ATC

CCA GAC AGG TTC AGT GGC AGT GGG TCT GGG ACA GAC

TTC ACT CTC ACC ATC AGC AGA CTA GAA CCT GAA GAT

TTT GCA ATA TAT TAC TGT CAG CAG CGT AGC AAC TGG

CCT TGG ACG TTC GGC CAA GGG ACC AAG GTG GAA ATC

AAA

> M0038-E06 HV
(SEQ ID NO: 14)

GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CCT TAC GTT ATG CAT TGG

GTT CGC CAA GCT CCT GGT AAA GGT TTG GAG TGG GTT

TCT TCT ATC TCT CCT TCT GGT GGC TGG ACT TAT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ATG GCT GTG TAT TAC TGT

GCG AGA GGG ACT GGA GCC TAC GGT ATG GAC GTC TGG

GGC CAA GGG ACC ACG GTC ACC GTC TCA AGC

> M0038-F01 LV
(SEQ ID NO: 15)

CAA GAC ATC CAG ATG ACC CAG TCT CCA TCC TCC CTG

TCT GCA TTT GTA GGA GAC AAA GTC ACC ATC ACT TGC

CGG GCA AGT CAG AGT GTT GGC ACC TAT TTA AAT TGG

-continued

TAT CAG CAG AAA GCA GGG AAA GCC CCT GAG CTC CTG

ATC TAT GCT ACA TCC AAT TTG CGA AGT GGG GTC CCA

TCA AGG TTC AGT GGC AGT GGA TCT GGG ACA GAT TTC

ACT CTC ACC ATC AAC ACT CTG CAA CCT GAA GAT TTT

GCA ACT TAC TAC TGT CAA CAG AGT TAC AGT ATC CCT

CGG TTT ACT TTC GGC CCT GGG ACC AAA GTG GAT ATC

AAA

> M0038-F01 HV
(SEQ ID NO: 16)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CTT TAC TCT ATG AAT TGG

GTT CGC CAA GCT CCT GGT AAA GGT TTG GAG TGG GTT

TCT TCT ATC TAT TCT TCT GGT GGC TCT ACT CTT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCG AGA GGT CGG GCT TTT GAT ATC TGG GGC CAA GGG

ACA ATG GTC ACC GTC TCA AGC

> M0038-F08 LV
(SEQ ID NO: 17)
CAA GAC ATC CAG ATG ACC CAG TCT CCA GGC ACC CTG

TCT TTG TCT CCA GGG GAA AGA GCC ACC CTC TCC TGC

AGG GCC AGT CAG AGT GTT AGC AGC AGC TAC TTA GCC

TGG TAC CAG CAG AAA CCT GGC CAG GCT CCC AGG CTC

CTC ATC TAT GGT GCA TCC AGC AGG GCC ACT GGC ATC

CCA GAC AGG TTC AGT GGC AGT GGG TCT GGG ACA GAC

TTC ACT CTC ACC ATC AGC AGA CTG GAG CCT GAA GAT

TTT GCA GTG TAT TAC TGT CAG CAC TAT GGT GGC TCA

CAG GCT TTC GGC GGA GGG ACC AAG GTG GAG ATC AAA

> M0038-F08 HV
(SEQ ID NO: 18)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CGT TAC AAG ATG TGG TGG

GTT CGC CAA GCT CCT GGT AAA GGT TTG GAG TGG GTT

TCT GGT ATC CGT CCT TCT GGT GGC TTA CTC GTT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCG AGA CGC GGT GAC TAC GTC GGG GGG TTT GAC TAC

TGG GGC CAG GGA ACC CTG GTC ACC GTC TCA AGC

> M0039-H08 LV
(SEQ ID NO: 19)
CAA GAC ATC CAG ATG ACC CAG TCT CCA GCC ACC CTG

TCT GTG TCT CCA GGG GAA AGA GCC ACC CTC TCC TGC

AGG GCC AGT GAG AGT GTT AAA AAC AAC TTA GCC TGG

TAT CAG CAG AAA CCT GGC CAG GCT CCC AGG CTC CTC

ATC TAT GGT GTT TCC ACC AGG GCC CCT GGT ATC CCA

GCC AGG TTC AGT GGC AGT GGG TCT GGG ACA GAC TTC

ACT CTC ACC ATC AGC AGC CTA GAG CCT GAA GAT TTT

GCA GTT TAT TAC TGT CAG CAG CGT AGC AAC TGG CCT

CCG GTC ACC TTC GGC CAA GGG ACA CGA CTG GAG ATT

AAA

> M0039-H08 HV
(SEQ ID NO: 20)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT GCT TAC AAT ATG GGT TGG

GTT CGC CAA GCT CCT GGT AAA GGT TTG GAG TGG GTT

TCT TCT ATC TCT TCT TCT GGT GGC TAT ACT GGT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCG AGA GAT CTT TAC AGG GGC TTT GAC TAC TGG GGC

CAG GGA ACC CTG GTC ACC GTC TCA AGC

> M0040-A06 LV
(SEQ ID NO: 21)
CAG GAC ATC GTC ATG ACT CAA ACC CCT CCT AGT TTA

CCG GTT AAC CCG GGT GAA CCT GCC TCC ATC TCC TGC

AGG TCT AGT CAG AGC CTC CTG CAT AGA AAT GGA TAC

AAC TAT TTG GAT TGG TAC CTG CAG AAG CCA GGG CAG

TCT CCA CAG CTC CTG ATC CAT TTG GGT TCT TAT CGG

GCC TCC GGG GTC CCT GAC AGG TTC AGT GGC AGT GGA

TCA GGC ACA GAT TTT ACA CTG AAA ATC AGC AGA GTG

GAG GCT GAG GAT GTT GGG GTT TAT TAC TGC ATG CAA

CCT CTA CAA ACT CCA TTC ACT TTC GGC CCT GGG ACC

AAA GTG GAT ATC AAA

> M0040-A06 HV
(SEQ ID NO: 22)
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT TAT TAC GGT ATG TAT TGG

GTT CGC CAA GCT CCT GGT AAA GGT TTG GAG TGG GTT

TCT TCT ATC TCT TCT TCT GGT GGC TAT ACT GAT TAT

GCT GAC TCC GTT AAA GGT CGC TTC ACT ATC TCT AGA

-continued

```
GAC AAC TCT AAG AAT ACT CTC TAC TTG CAG ATG AAC

AGC TTA AGG GCT GAG GAC ACG GCC GTG TAT TAC TGT

GCA AGG AGG ATT AAG TAT TAC GAT ATT GAA GGG GAA

GGT GCT TTT GAT ATC TGG GGC CAA GGG ACA ATG GTC

ACC GTC TCA AGC
```

> M0040-A11 LV (SEQ ID NO: 22)
```
CAG AGC GCT TTG ACT CAG CCT CCC TCC GCG TCC GGG

TCT CCT GGA CAG TCA GTC ACC ATC TCC TGC ACT GGA

ACC AGC AGT GAC GTT GGT GCT TAT AAC TAT GTC TCC

TGG TAC CAA CAG CAC CCA GAC AAA GCC CCC AAA CTC

ATT ATT TAT AAT GTC AAT GAG CGG CCC TCA GGG GTC

CCT GAT CGC TTC TCT GGC TCC AAG TCT GGC AAC ACG

GCC TCC CTG ACC GTC TCT GGG CTC CAG GCT GAG GAT

GAG GCT GAT TAT TAC TGT ACC TCA TAT GCA GGC AGC

AAC AAA ATC GGG GTC TCC GGA ACT GGG ACC AAG GTC

ACC GTC CTA
```

> M0040-A11 HV (SEQ ID NO: 24)
```
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT CAT TAC GTT ATG TTT TGG

GTT CGC CAA GCT CCT GGT AAA GGT TTG GAG TGG GTT

TCT CGT ATC GTT CCT TCT GGT GGC GCT ACT ATG TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCG AGA GAT CGA CCG CTC TAT GAT AGT AGT GGT TAC

GTT GAC TAC TGG GGC CAG GGA ACC CTG GTC ACC GTC

TCA AGC
```

> M0043-G02 LV (SEQ ID NO: 25)
```
CAA GAC ATC CAG ATG ACC CAG TCT CCA GGC ACC CTG

TCT TTG TCT CCA GGG GAA AGA GCC ACC CTC TCC TGC

AGG GCC AGT CAG AGT GTT AGC AGC AGC TAC TTA GCC

TGG TAC CAG CAG AAA CCT GGC CAG GCT CCC AGG CTC

CTC ATC TAT GGT GCA TCC AGC AGG GCC ACT GGC ATC

CCA GAC AGG TTC AGT GGC AGT GGG TCT GGG ACA GAC

TTC ACT CTC ACC ATC AGC AGA CTG GAG CCT GAA GAT

TTT GCA GTG TAT TAC TGT CAG TCG GGG GTC ACT TTC

GGC GGA GGG ACC AAG GTG GAG ATC AAA
```

> M0043-G02 HV (SEQ ID NO: 26)
```
GAA GTT CAA TTG TTA GAG TCT GGT GGC GGT CTT GTT

CAG CCT GGT GGT TCT TTA CGT CTT TCT TGC GCT GCT

TCC GGA TTC ACT TTC TCT TGG TAC CCT ATG TTT TGG

GTT CGC CAA GCT CCT GGT AAA GGT TTG GAG TGG GTT

TCT GGT ATC TAT TCT TCT GGT GGC CCT ACT GAT TAT

GCT GAC TCC GTT AAA GGT CGC TTC ACT ATC TCT AGA

GAC AAC TCT AAG AAT ACT CTC TAC TTG CAG ATG AAC

AGC TTA AGG GCT GAG GAC ACG GCC GTG TAT TAC TGT

GCA AAA GAT ACC CTA GGG AGG TAT TAC GAT TTT GG

AGT GGT TAT TCC TAC GGT ATG GAC GTC TGG GGC CAA

GGG ACC ACG GTC ACC GTC TCA AGC
```

The amino acid sequences of exemplary Fab heavy chain (HC) and light chain (LC) variable regions that bind to and inhibit human MMP-14 are shown herein in Table 3. In Table 3, the standard numbering of the HC V domain is shown. The length of HC CDR3 varies considerably. By convention, the second cysteine is numbered 92 and the W of the conserved WG motif of FR4 is number 103. If there are more than 9 residues between C92 and W103, then residues after 102 are numbered 102a, 102b, etc.

TABLE 3

Amino-acid sequences of Fabs that bind and inhibit human MMP-14

1 M0031-C02 SC = SC-001 Round = SC-001-SR-003
HC (SEQ ID NO: 27)
```
              1         5         0         5         0         5         0         5         0
    1         EVQLLESGGG LVQPGGSLRL SCAASGFTFS PYPMGWVRQA
                        5         0
              PGKGLEWVSS 5         5         6         6         7         7         8  8       8  8
              1         a         5         0         5         0         5  0       2abc3 5
    51        IVSSGGLTLY ADSVKGRFTI SRDNSKNTLY LQMNSLRAED 8  8      9    9
              7  9      2    5
              TAVYYCARGG 1              1  1          1
              9          0              0  0          1
              7         2abcd         efghi3 5        0
    101       RLYDILTGQG APFDYWGQGT LVTVSS
```
LC
(SEQ ID NO: 28)
```
    1         QDIQMTQSPL SLPVTPGEPA SISCRSSQSL LHSNGYYYLD
              WYLQKPGQSP

51        QLLIYLGSYR ASGVPDRFSG SGSGTDFTLK ISSVEAEDVG
              VYYCMQALQT

101       PLTFGGGTRV DIK
```

2 M0031-F01 SC = SC-001 Round = SC-001-SR-003
HC
(SEQ ID NO: 29)
```
    1         EVQLLESGGG LVQPGGSLRL SCAASGFTFS TYEMHWVRQA
              PGKGLEWVSS

51        IYSSGGWTGY ADSVKGRFTI SRDNSKNTLY LQMNSLRAED
              TAVYYCARSQ

101       QYYDFSSRYY GMDVWGQGTT VTVSS
```

TABLE 3-continued

Amino-acid sequences of Fabs that bind and inhibit human MMP-14

LC
(SEQ ID NO: 30)
1   QSELTQPPSV SGTPGQRVTI SCSGTSANIG RNAVHWYQQL
    PGTAPKLLIH

51  SNNRRPSGVP DRFSGSKSGT SASLAISGLQ SEDEADYYCA
    AWENSLNAFY

101 VFGTGTKVTV L

3 M0033-H07 SC = SC-001 Round = SC-001-SR-003
HC
(SEQ ID NO: 31)
1   EVQLLESGGG LVQPGGSLRL SCAASGFTFS VYGMVWVRQA
    PGKGLEWVSV

51  ISSSGGSTWY ADSVKGRFTI SRDNSKNTLY LQMNSLRAED
    TALYYCARPF

101 SRRYGVFDYW GQGTLVTVSS

LC
(SEQ ID NO: 32)
1   QDIQMTQSPS SLSASVGDRV TITCRASQGI RNFLAWYQQK
    PGKVPKLLVF

51  GASALQSGVP SRFSGSGSGT DFTLTISGLQ PEDVATYYCQ
    KYNGVPLTFG

101 GGTKVEIK

4 M0037-009 SC = SC-001 Round = SC-001-SR-003
HC
(SEQ ID NO: 33)
1   EVQLLESGGG LVQPGGSLRL SCAASGFTFS HYEMFWVRQA
    PGKGLEWVSS

51  ISPSGGQTHY ADSVKGRFTI SRDNSKNTLY LQMNSLRAED
    TAVYYCATDR

101 TYYDFWSGYG PLWYWGQGTL VTVSS

LC
(SEQ ID NO: 34)
1   QDIQMTQSPL SLPVTLGESA SVSCRSSQSL LHENGHNYLD
    WYLQKPGQSP

51  QLLIYLGSNR ASGVPDRFSG SGSGTDFTLK ISRVEAEDVG
    VYYCMQSLKT

101 PPTFGPGTKV EIK

5 M0037-D01 SC = SC-001 Round = SC-001-SR-003
HC
(SEQ ID NO: 35)
1   EVQLLESGGG LVQPGGSLRL SCAASGFTFS MYMMIWVRQA
    PGKGLEWVSS

51  IYPSGGNTMY ADSVKGRFTI SRDNSKNTLY LQMNSLRAED
    TAVYYCATGV

101 LRYFDWDAGS GMDVWGQGTT VTVSS

LC
(SEQ ID NO: 36)
1   QDIQMTQSPS SLSASVGDRV TITCRASQGI RNDLGWYQQK
    PGKAPKRLIY

51  VASSLQSGVP SRFSGSGSGT EFTLTISSLQ PEDFATYYCL
    QHNSYPWTFG

101 QGTKVEIK

6 M0038-E06 SC = SC-001 Round = SC-001-SR-003
HC
(SEQ ID NO: 37)
1   EVQLLESGGG LVQPGGSLRL SCAASGFTFS PYVMHWVRQA
    PGKGLEWVSS

51  ISPSGGWTYY ADSVKGRFTI SRDNSKNTLY LQMNSLRAED
    MAVYYCARGT

101 GAYGMDVWGQ GTTVTVSS

LC
(SEQ ID NO: 38)
1   QDIQMTQSPG TLSLSPGDRA TLSCGASQLV VSNYIAWYQQ
    KPGQAPRLLM

51  YAGSIRATGI PDRFSGSGSG TDFTLTISRL EPEDFAIYYC
    QQRSNWPWTF

101 GQGTKVEIK

7 M0038-F01 SC = SC-001 Round = SC-001-SR-003
HC
(SEQ ID NO: 39)
1   EVQLLESGGG LVQPGGSLRL SCAASGFTFS LYSMNWVRQA
    PGKGLEWVSS

51  IYSSGGSTLY ADSVKGRFTI SRDNSKNTLY LQMNSLRAED
    TAVYYCARGR

101 AFDIWGQGTM VTVSS

LC
(SEQ ID NO: 40)
1   QDIQMTQSPS SLSAFVGDKV TITCRASQSV GTYLNWYQQK
    AGKAPELLIY

51  ATSNLRSGVP SRFSGSGSGT DFTLTINTLQ PEDFATYYCQ
    QSYSIPRFTF

101 GPGTKVDIK

8 M0038-F08 SC = SC-001 Round = SC-001-SR-003
HC
(SEQ ID NO: 41)
1   EVQLLESGGG LVQPGGSLRL SCAASGFTFS RYKMWWVRQA
    PGKGLEWVSG

51  IRPSGGLTRY ADSVKGRFTI SRDNSKNTLY LQMNSLRAED
    TAVYYCARRG

101 DYVGGFDYWG QGTLVTVSS

LC
(SEQ ID NO: 42)
1   QDIQMTQSPG TLSLSPGERA TLSCRASQSV SSSYLAWYQQ
    KPGQAPRLLI

51  YGASSRATGI PDRFSGSGSG TDFTLTISRL EPEDFAVYYC
    QHYGGSQAFG

101 GGTKVEIK

9 M0039-H08 SC = SC-001 Round = SC-001-SR-003
HC
(SEQ ID NO: 43)
1   EVQLLESGGG LVQPGGSLRL SCAASGFTFS AYNMGWVRQA
    PGKGLEWVSS

51  ISSSGGYTGY ADSVKGRFTI SRDNSKNTLY LQMNSLRAED
    TAVYYCARDL

101 YRGFDYWGQG TLVTVSS

TABLE 3-continued

Amino-acid sequences of Fabs that bind and inhibit human MMP-14

LC
(SEQ ID NO: 44)
1   QDIQMTQSPA TLSVSPGERA TLSCRASESV KNNLAWYQQK
    PGQAPRLLIY
51  GVSTRAPGIP ARFSGSGSGT DFTLTISSLE PEDFAVYYCQ
    QRSNWPPVTF
101 GQGTRLEIK

10 M0040-A06 SC = SC-001 Round = SC-001-SR-003
HC
(SEQ ID NO: 45)
1   EVQLLESGGG LVQPGGSLRL SCAASGFTFS YYGMYWVRQA
    PGKGLEWVSS
51  ISSSGGYTDY ADSVKGRFTI SRDNSKNTLY LQMNSLRAED
    TAVYYCARRI
101 KYYDIEGEGA FDIWGQGTMV TVSS LC
(SEQ ID NO: 46)
1   QDIVMTQTPP SLPVNPGEPA SISCRSSQSL LHRNGYNYLD
    WYLQKPGQSP
51  QLLIHLGSYR ASGVPDRFSG SGSGTDFTLK ISRVEAEDVG
    VYYCMQPLQT
101 PFTFGPGTKV DIK 11 M0040-A11 SC = SC-001 Round = SC-001-SR-003
HC
(SEQ ID NO: 47)
1   EVQLLESGGG LVQPGGSLRL SCAASGFTFS HYVMFWVRQA
    PGKGLEWVSR
51  IVPSGGATMY ADSVKGRFTI SRDNSKNTLY LQMNSLRAED
    TAVYYCARDR
101 PLYDSSGYVD YWGQGTLVTV SS LC
(SEQ ID NO: 48)
1   QSALTQPPSA SGSPGQSVTI SCTGTSSDVG AYNYVSWYQQ
    HPDKAPKLII
51  YNVNERPSGV PDRFSGSKSG NTASLTVSGL QAEDEADYYC
    TSYAGSNKIG
101 VSGTGTKVTV L 12 M0043-G02 SC = SC-001 Round = SC-001-SR-003
HC
(SEQ ID NO: 49)
1   EVQLLESGGG LVQPGGSLRL SCAASGFTFS WYPMFWVRQA
    PGKGLEWVSG
51  IYSSGGPTDY ADSVKGRFTI SRDNSKNTLY LQMNSLRAED
    TAVYYCAKDT
101 LGRYYDFWSG YSYGMDVWGQ GTTVTVSS LC
(SEQ ID NO: 50)
1   QDIQMTQSPG TLSLSPGERA TLSCRASQSV SSSYLAWYQQ
    KPGQAPRLLI
51  YGASSRATGI PDRFSGSGSG TDFTLTISRL EPEDFAVYYC
    QSGVTFGGGT
101 KVEIK In one embodiment, an MMP-14 antibody for use with the combination therapies as described herein is DX-2400. The variable domain sequences for DX-2400 are:

VH:
(SEQ ID NO: 51)
FR1------------------------ CDR1-
DX-2400   EVQLLESGGGLVQPGGSLRLSCAASGFTFS LYSMN

FR2---------- CDR2-------
WVRQAPGKGLEWVS SIYSSGGSTLY

CDR2-- FR3-----------------------------
DX-2400   ADSVKG RFTISRDNSKNTLYLQMNSLRAEDTAVYYCAR

CDR3-- FR4---------
GRAFDI WGQGTMVTVSS

CDR regions are in bold.

VL:
(SEQ ID NO: 52)
FR1------------------- CDR1-------
DX-2400   DIQMTQSPSSLSASVGDRVTITC RASQSVGTYLN

FR2------------ CDR2---
WYQQKPGKAPKLLIY ATSNLRS GVPS

FR3------------------------
RFSGSGSGTDFTLTISSLQPEDFATYYC

DX-2400   CDR3------ FR4-------
QQSYSIPRFT FGPGTKVDIK

CDR regions are in bold.

MMP-14 Binding Proteins for Use in Therapy, e.g., a Combination Therapy:

Proteins that bind to MMP-14 as described herein or in e.g., U.S. Pat. No. 7,745,587 have therapeutic and prophylactic utilities, particularly in human subjects. These binding proteins are administered to a subject alone or in combination with one or more additional therapies to treat and/or prevent a variety of disorders. Such therapies comprising MMP-14 binding proteins can be administered to a subject, or even to cells in culture, e.g. in vitro or ex vivo. Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

As used herein, an amount of an MMP-14 binding agent effective to prevent a disorder, or a prophylactically effective amount of the binding agent refers to an amount of e.g., an MMP-14 binding protein, e.g., an anti-MMP-14 antibody described herein, which is effective, upon single- or multiple-dose administration to the subject, for preventing or delaying the occurrence of the onset or recurrence of a disorder, e.g., a disorder described herein. In some embodiments, the dose required to achieve a therapeutically or prophylactically effective amount of an MMP-14 binding agent is decreased when used in combination with one or more additional agents, compared to the dose required when an MMP-14 binding protein is administered alone. In some embodiments, the dose required to achieve a therapeutically or prophylactically effective amount of a chemotherapeutic agent, e.g., an alklyating agent, a taxane or an antimetabolite, e.g., an alkylating agent, a taxane or an antimetabolite described herein, is decreased when used in combination with an MMP-14 binding protein, compared to the dose required when the alklyating agent, taxane or antimetabolite is administered alone. For example, the dose required to achieve a therapeutically or prophylactically effective amount of an alkylating agent such as darcabazine can be decreased when used in combination with an MMP-14 binding protein, as compared to the dose required when the alkylating agent, e.g., darcabazine, is administered alone. The decreased dose can be, e.g., a decrease dose of the alkylating agent, e.g., darcabazine, compared to an approved dose to treat a disorder such as melanoma when the agent is administered alone. As another example, the dose required to achieve a therapeutically or prophylactically effective amount of a taxane such as paclitaxel when used in combination with an MMP-14 binding protein can be decreased as compared to the dose administered with the taxane alone to treat a disorder such as melanoma. Again, the dose of the taxane, e.g., paclitaxel, can be decreased, e.g., as compared to an approved dose of the taxane to treat the disorder, e.g., melanoma. As a further example, the dose required to achieve a therapeutically or prophylactically effective amount of an antimetabolite such as gemcitabine when used in combination with an MMP-14 binding protein can be decreased as compared to the dose administered with the antimetabolite alone to treat a disorder such as pancreatic cancer. The dose of the antimetabolite, e.g., gemcitabine, can be decreased as compared to an approved dose of the antimetabolite to treat the disorder, e.g., pancreatic cancer.

The MMP-14 binding proteins can be used as competitive agents to inhibit, reduce an undesirable interaction, e.g., between a natural or pathological agent and the MMP-14. The dose of the MMP-14 binding protein can be the amount sufficient to block 90%, 95%, 99%, or 99.9% of the activity of MMP-14 in the patient, especially at the site of disease. Depending on the disease, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

The MMP-14 binding proteins can be used directly in vivo to eliminate antigen-expressing cells via natural complement-dependent cytotoxicity (CDC) or antibody dependent cellular cytotoxicity (ADCC). The binding proteins described herein can include complement binding effector domain, such as the Fc portions from IgG1, -2, or -3 or corresponding portions of IgM which bind complement. In one embodiment, a population of target cells is ex vivo treated with a binding agent described herein and appropriate effector cells. The treatment can be supplemented by the addition of complement or serum containing complement. Further, phagocytosis of target cells coated with a binding protein described herein can be improved by binding of complement proteins. In another embodiment target, cells coated with the binding protein which includes a complement binding effector domain are lysed by complement.

Therapeutic Agents

Essentially any agent known or expected to have efficacy in the treatment of cancer or a related disorder, can be administered as a combination therapy with an MMP-14 binding protein. For example, such therapeutic agents can be anti-cancer agents such as e.g., a cytotoxic or a cytostatic agent. Exemplary cytotoxic agents include antimicrotubule agents such as taxanes, topoisomerase inhibitors, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Non-limiting examples of anti-cancer agents include, e.g., anti-microtubule agents such as taxanes, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, docetaxel, larotaxel, cabazitaxel; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5 FU), methotrexate, 6-mercaptopurine, 6-thioguanine, fludarabine phosphate, cytarabine/Ara C, trimetrexate, gemcitabine, acivicin, alanosine, pyrazofurin, N-Phosphoracetyl-L-Asparate=PALA, pentostatin, 5-azacitidine, 5-Aza-2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4 ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl) propionanilide.

In one embodiment, an MMP-14 binding protein, e.g., DX-2400, is administered in combination with an agent selected from the group consisting of: gemcitabine, paclitaxel, or darcabazine.

In one embodiment, an MMP-14 binding protein, e.g., DX-2400, is administered in combination with darcabazine to treat melanoma (e.g., malignant melanoma). In some embodiments, the darcabazine is administered at a dose of 2 to 4.5 mg/kg/day, e.g., for 7, 8, 9, 10, 11, or 12 days. In another embodiment, the darcabazine is administered at a dose of 2 mg/kg/day or less (e.g., 1.5 mg/kg/day to 0.5 mg/kg/day, e.g., 1 mg/kg/day), e.g., for 7, 8, 9, 10, 11 or 12 days. The treatment with darcabazine can be repeated, e.g., every two to three weeks.

In one embodiment, an MMP-14 binding protein, e.g., DX-2400, is administered in combination with paclitaxel to treat melanoma (e.g., advanced or malignant melanoma). In some embodiments, the paclitaxel is administered at a dose of 135 to 175 mg/m$^2$, e.g., every three weeks. In another embodiment, the paclitaxel is administered at a dose less than 135 mg/m$^2$ (e.g., between 130 mg/m$^2$ to 100 mg/m$^2$), e.g., every three weeks.

In one embodiment, an MMP-14 binding protein, e.g., DX-2400, is administered in combination with gemcitabine to treat pancreatic cancer (e.g., locally advanced (nonresectable Stage II or Stage III) or metastatic pancreatic cancer). In some embodiments, gemcitabine is administered at a dose of 1000 mg/m$^2$, e.g., once a week. In another embodiment, gemcitabine is administered at a dose less than 1000 mg/m$^2$ (e.g., 950 to 700 mg/m$^2$, e.g., 900 to 800 mg/m$^2$), e.g., once a week.

Anti-cancer agents, e.g., kinase inhibitors, used in the therapeutic methods of the invention can also be evaluated and/or identified using screening assays. In one embodiment, the anti-cancer agents are evaluated in a cell-free system, e.g., a cell lysate or in a reconstituted system. In other embodiments, the anti-cancer agents are evaluated in a cell in culture, e.g., a cell model of human metastatic melanoma or human pancreatic cancer.

MMP-14 Binding Protein Conjugates:

MMP-14 binding proteins may be used to aid delivery of at least one additional agent (e.g., any of a variety of cytotoxic and therapeutic drugs) to cells and tissues where MMP-14 is present. In some embodiments, the MMP-14 binding protein and the one or more additional agents are conjugated together to take advantage of the MMP-14 binding activity and enhance delivery e.g., to a tumor or cancer expressing MMP-14.

Exemplary agents that can be conjugated to an MMP-14 binding protein include a compound emitting radiation, molecules of plants, fungal, or bacterial origin, biological proteins, and mixtures thereof. The cytotoxic drugs can be intracellularly acting cytotoxic drugs, such as toxins short range radiation emitters, e.g., short range, high energy α-emitters.

The MMP-14 binding moiety of a conjugate permits the agent to be targeted to MMP-14-expressing cells by e.g., binding to cells that are associated with (e.g., in proximity of or intermingled with) cancer cells, e.g., cancerous skin, pancreatic, lung, liver, colon, breast, ovarian, epidermal, laryngeal, and cartilage cells, and particularly metastatic cells thereof. In a preferred embodiment, the MMP-14 binding moiety can be used to inhibit (e.g., inhibit at least one activity, reduce growth and proliferation, or kill) any such cells and inhibit carcinogenesis. Reducing MMP-14 activity near a cancer can indirectly inhibit (e.g., inhibit at least one activity, reduce growth and proliferation, or kill) the cancer cells which may be dependent on the MMP-14 activity for metastasis, activation of growth factors, and so forth.

Alternatively, the binding proteins bind to cells in the vicinity of the cancerous cells, but are sufficiently close to the cancerous cells to directly or indirectly inhibit (e.g., inhibit at least one activity, reduce growth and proliferation, or kill) the cancers cells. Thus, the MMP-14 binding moiety of the conjugate can be used to selectively inhibit cells in cancerous tissue (including the cancerous cells themselves and cells associated with or invading the cancer).

To target MMP-14 expressing cells, particularly cancerous cells, a prodrug system can also be used. For example, a first MMP-14 binding protein is conjugated with a prodrug which is activated only when in close proximity with a prodrug activator. The prodrug activator is conjugated with a second MMP-14 binding protein, preferably one which binds to a non-competing site on the target molecule. Whether two binding proteins bind to competing or non competing binding sites can be determined by conventional competitive binding assays. Exemplary drug prodrug pairs are described in Blakely et al., (1996) Cancer Research, 56:3287 3292.

The MMP-14 binding protein can be used to deliver at least one additional agent such as macro and micromolecules, e.g., a gene into the cell for gene therapy purposes into the endothelium or epithelium and target only those tissues expressing the MMP-14. The binding proteins may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy α emitters, as described herein.

In the case of polypeptide toxins, recombinant nucleic acid techniques can be used to construct a nucleic acid that encodes the binding protein (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Alternatively, the MMP-14 binding protein can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{213}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Exemplary Diseases and Conditions

The combination therapies described herein are useful to treat diseases or conditions in which MMP-14 is implicated, e.g., a disease or condition described herein, or to treat one or more symptoms associated therewith. Examples of such diseases and conditions include a cancer (e.g., pancreatic cancer, or melanoma) or inappropriate angiogenesis.

A therapeutically effective amount of a therapy comprising an MMP-14 binding protein is administered to a subject having or suspected of having cancer or a related disorder in which MMP-14 is implicated, thereby treating (e.g., ameliorating or improving a symptom or feature of a disorder, slowing, stabilizing or halting disease progression) the disorder.

Cancer

Matrix metalloprotease-14 (MMP-14) is believed to contribute to cancer by cleaving components of the ECM and basement membranes, thereby allowing cancer cells to penetrate and infiltrate the subjacent stromal matrix. Additionally, a number of growth-factor receptors, cell adhesion molecules, chemokines, cytokines, apoptotic ligands, and angiogenic factors are substrates of MMPs. Hence, MMP activity may cause activation of growth factors, suppression of tumor cell apoptosis, destruction of chemokine gradients developed by host immune response, or release of angiogenic factors. MMPs may facilitate tumor growth by promoting the release of cell proliferation factors such as insulin-like growth factors which are bound to specific binding proteins (IGFBPs) (Manes et al., 1997 *J. Biol. Chem.* 272: 25706-25712).

Collagenases, including MMP-2, have been found at elevated levels in melanoma and in cancers of the colon, breast, lung, prostate, and bladder. Usually, these elevated levels correlate with higher tumor grade and invasiveness. MMP-2 levels are significantly elevated in the serum of patients with metastatic lung cancer, and in those patients with high levels, response to chemotherapy is diminished.

Likewise, MMP-14, which cleaves proMMP-2 to release active MMP-2, is elevated in numerous cancers and can contribute to the growth of tumors, tumor embolism, and the mobility, invasiveness and metastasis of cancer (e.g., CNS tumors (e.g., gliomas), head and neck cancer, oral cavity cancer, laryngeal cancer, chondrosarcoma, breast cancer).

Accordingly, the disclosure provides methods of treating (e.g., slowing, eliminating, or reversing tumor growth, preventing or reducing, either in number or size, metastases, reducing or eliminating tumor cell invasiveness, providing an increased interval to tumor progression, or increasing disease-free survival time) cancer (e.g., metastatic melanoma, pancreatic cancer, breast cancer, head and neck cancer, oral cavity cancer, laryngeal cancer, chondrosarcoma, ovarian cancer, testicular carcinoma, brain tumors (e.g., astrocytomas, glioblastomas, gliomas)) by administering an effective amount of an MMP-14 binding protein, optionally, in combination with at least one additional therapeutic agent. In some embodiments, the MMP-14 binding protein inhibits MMP-14 activity.

Also provided are methods of preventing or reducing risk of developing cancer, by administering an effective amount as described herein to a subject at risk of developing cancer, thereby reducing the subject's risk of developing a cancer.

The disclosure further provides methods of modulating (e.g. reducing or preventing) angiogenesis at a tumor site by administering an effective amount of an MMP-14 binding protein or a combination therapy as described herein, thereby reducing or preventing angiogenesis at the tumor site. The MMP-14 binding protein may be administered in combination with 1, 2, 3, 4, 5, or more additional agents.

Also provided are methods for reducing extracellular matrix (ECM) degradation by a tumor, comprising administering an effective amount of an MMP-14 binding protein in combination with at least one additional agent to a subject, thereby reducing ECM degradation by a tumor in the subject.

The disclosed methods are useful in the prevention and treatment of solid tumors, soft tissue tumors, and metastases thereof. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Metastases of the aforementioned cancers can also be treated or prevented in accordance with the methods described herein.

In one embodiment, the cancer to be treated is melanoma (e.g., metastatic melanoma). In another embodiment, the cancer to be treated is pancreatic cancer.

Guidance for determination of a therapeutically effective amount of the combination therapy for treatment of cancer may be obtained by reference to in vivo models of the cancer to be treated. For example, the amount of the combination therapy that is a therapeutically effective amount in a rodent or Libechov minipig model of cancer may be used to guide the selection of a dose that is a therapeutically effective amount. A number of rodent models of human cancers are available, including nude mouse/tumor xenograft systems (e.g., melanoma xenografts; see, e.g., Trikha et al. *Cancer Research* 62:2824-2833 (2002)) and murine models of breast cancer or glioma (e.g., Kuperwasser et al., *Cancer Research* 65, 6130-6138, (2005); Bradford et al., *Br J Neurosurg.* 3(2):197-210 (1989)). A melanoblastoma-bearing Libechov minipig (MeLiM) is available as an animal model of melanoma (e.g., Boisgard et al., *Eur J Nucl Med Mol Imaging* 30(6):826-34 (2003)).

Metastatic Melanoma

Metastatic melanoma is a type of skin cancer that has spread from its original lesion site (i.e., melanocytes) to deeper parts of the skin, and eventually to other parts of the body distant to the primary lesion site.

Symptoms of metastatic melanoma include, e.g., changes to the shape (e.g., asymmetry, irregular boarders, diameter, elevated above the skin surface), hardness, or color (e.g., variegated color) of existing moles or the appearance of a new lump anywhere on the skin, nonspecific paraneoplastic symptoms (e.g., loss of appetite, nausea, vomiting, fatigue). Brain, lymph nodes, lung, or liver metastases are common in patients with metastatic melanoma.

Treatment of metastatic melanoma includes, e.g., surgery, adjuvant treatment, chemotherapy (e.g., dacarbazine (DTIC-DOME®), gemcitabine (GEMZAR®), paclitaxel (TAXOL®)), immunotherapy (e.g., interleukin-2, interferon), Mohs surgery, radiation therapy, imiquimod (ALDARA®) topical cream, targeted therapy (e.g., ipilimumab (YERVOY™), BRAF inhibitors, adoptive cell therapy, gene therapy), or a combination thereof.

The disclosure provides methods of treating (e.g., ameliorating, stabilizing, or eliminating one or more symptoms or ameliorating or stabilizing the subject's score on a melanoma scale) metastatic melanoma by administering a therapeutically effective amount of a MMP-14 binding protein to a subject having or suspected of having metastatic melanoma. Additionally provides are methods of treating metastatic melanoma by administering a therapeutically effective amount of a MMP-14 binding protein and at least one of the therapeutic agents described herein, e.g., a chemotherapeutic agent (e.g., an alkylating agent, e.g., dacarbazine, and/or a taxane, e.g., paclitaxel).

Further provided are methods of treating (e.g., ameliorating, stabilizing, or eliminating one or more symptoms) metastases arising from melanoma (e.g., metastases into lymph nodes, lung, liver, or brain) by administering a therapeutically effective amount of an MMP-14 binding protein.

Scales useful for assessing metastatic melanoma and symptoms of metastatic melanoma include the American Joint Committee on Cancer Staging System for Cutaneous Melanoma (Balch et al., (2001) *J. Clin. Oncol.* 19(16): 3635-48), Clark level and Breslow's depth (Weedon (2002) *Skin Pathology.* 2nd Edition. Sydney: Churchill-Livingstone).

Guidance for the determination of the dosage that delivers a therapeutically effective amount of a MMP-14 binding protein may be obtained from animal models of metastatic melanoma, such as mouse models for melanomas (e.g., transplantation models, syngeneic transplantation models, and genetically modified animals as described in Becker et al., (2010) *Exp. Dermatol.* 19(2):157-64); and rodent models of brain metastasis in melanoma (Cranmer et al., (2005) *Melanoma Res.* 15(5):325-56).

Pancreatic Cancer

Pancreatic cancer is a malignant neoplasm of the pancreas. The more common type of pancreatic cancer, accounting for about 95% of these tumors is adenocarcinoma, which arises within the exocrine component of the pancreas. A less common type arises from the islet cells and is classified as a neuroendocrine tumor.

Symptoms of pancreatic cancer include, e.g., pain in the upper abdomen that typically radiates to the back, loss of appetite, nausea, vomiting, significant weight loss, painless jaundice (e.g., yellow tint to whites of eyes, yellowish skin, darkened urine), pale-colored stool, steatorrhea, skin irritation, Trousseau sign, diabetes mellitus, and clinical depression. Pancreatic cancer can metastasize to e.g., regional lymph nodes, liver, lungs, bone, or brain.

Treatment of pancreatic cancer includes, e.g., surgery, chemotherapy (e.g., dacarbazine (DTIC-DOME®), gemcitabine (GEMZAR®), paclitaxel (TAXOL®), oxaliplatin (ELOXATIN®)), hormone therapy, radiation therapy, radiolabeled hormone, radiofrequency ablatioradiation therapy, targeted therapy (e.g., erlotinib (TARCEVA®)), or a combination thereof.

The disclosure provides methods of treating (e.g., ameliorating, stabilizing, or eliminating one or more symptoms or ameliorating or stabilizing the subject's score on a pancreatic cancer scale) pancreatic cancer by administering a therapeutically effective amount of a MMP-14 binding protein to a subject having or suspected of having pancreatic cancer. Additionally provided are methods of treating pancreatic cancer by administering a therapeutically effective amount of a MMP-14 binding protein and at least one of the therapeutic agents described herein, e.g., a chemotherapeutic agent (e.g., an antimetabolite, e.g., gemcitabine).

Further provided are methods of treating (e.g., ameliorating, stabilizing, or eliminating one or more symptoms) metastases arising from pancreatic cancer (e.g., metastases into lymph nodes, lungs, liver, bone, or brain) or a disorder associated with pancreatic cancer by administering a therapeutically effective amount of an MMP-14 binding protein.

Scales useful for assessing pancreatic cancer and symptoms of pancreatic cancer include the American Joint Committee on Cancer (AJCC) TNM staging system (Edge et al., (2010) *AJCC Cancer Staging Manual*, Springer).

Guidance for the determination of the dosage that delivers a therapeutically effective amount of a MMP-14 binding protein may be obtained from animal models of pancreatic cancer, such as mouse models for pancreatic cancer as described in Leach, (2004) *Cancer Cell,* 5(1):7-11; and rat model of pancreatic ductal adenocarcinoma (Rivera et al., (1997) *Surgery,* 122(1):82-90).

Angiogenesis and Capillary Tube Formation

The role of MMPs in angiogenesis is dual and complex. The relevance of these enzymes as positive regulators of tumor angiogenesis has been largely demonstrated. However MMPs have also been reported to act as inhibitors of angiogenesis, by recent descriptions of mechanisms by which these enzymes negatively regulate angiogenesis have contributed to increase the functional complexity of this proteolytic system in cancer. A number of MMPs are able to cleave the precursors of angiostatin and endostatin, and generate the active forms of these endogenous inhibitors of angiogenesis (Cornelius et al., 1998 *J Immunol.,* 161(12): 6845-52; Ferreras et al., 2000 *FEBS Lett.* 486(3):247-51). Human endothelial cell (EC) tube formation induced by the chemokines CCL2 and CXCL8 is highly dependent on MMP-14 activity.

The disclosure provides methods of modulating (e.g., inhibiting) inappropriate angiogenesis or capillary tube formation by administering a therapeutically effective amount of a MMP-14 binding protein (e.g., an anti-MMP-14 IgG or Fab that inhibits MMP-14) in combination with at least one additional agent (e.g., an anti-cancer agent) to a subject in need of modulation of inappropriate angiogenesis or capillary tube formation. Also provided are methods in which inappropriate angiogenesis or capillary tube formation is modulated by administering a MMP-14 binding protein and an additional angiogenesis or capillary tube formation modulating agent, such as a VEGF or Tie1 inhibitor.

Guidance regarding the efficacy and dosage of a combination therapy comprising an MMP-14 binding protein and at least one additional agent, which will deliver a therapeutically effective amount of the protein can be obtained from a model of angiogenesis, e.g., a Matrigel-based angiogenesis assay in nude rats, or in a model of capillary tube formation, e.g., endothelial MC-based sprouting assay (Trikha et al. *Cancer Research* 62:2824-2833 (2002)) or a capillary tube formation assay or an angiogenesis assay as described in U.S. Ser. No. 11/199,739 and PCT/US2005/0284, both filed Aug. 9, 2005.

Combination Therapies for Specific Cancers

The MMP-14 binding proteins described herein can be administered in combination with one or more of the other therapies for treating cancers, including, but not limited to: surgery; radiation therapy, and chemotherapy. For example, MMP-14 binding proteins that inhibit MMP-14 or that inhibit a downstream event of MMP-14 activity (e.g., cleavage of pro-MMP-2 to MMP-2) can also be used in combination with other anti-cancer therapies, such as radiation therapy, chemotherapy, surgery etc.

Melanoma and Metastatic Melanoma:

Treatment of melanoma or metastatic melanoma can be achieved by administering a combination therapy comprising an MMP-14 binding protein and at least one additional anti-cancer agent to a subject in need thereof.

Anti-cancer agents that can be administered in combination with an MMP-14 binding protein for the treatment of melanoma include, but are not limited to, interferon, dacarbazine, interleukin-2, or radiation (e.g., radioimmunotherapy). In one embodiment, a combination of an MMP-14 binding protein and dacarbazine is administered to a subject for the treatment of melanoma. In another embodiment, a combination of DX-2400 and dacarbazine is administered to the subject for the treatment of melanoma.

Pancreatic Cancer:

Treatment of pancreatic cancer can be achieved by administering to a subject having, or suspected of having, pancreatic cancer a combination therapy comprising an MMP-14 binding protein and at least one additional anti-cancer agent.

Some non-limiting examples of anti-cancer agents for use with the methods described herein include, gemcitabine, oxaliplatin, erlotinib (TARCEVA™), among others. In one embodiment, a combination therapy comprising an MMP-14 binding protein and gemcitabine is used for the treatment of pancreatic cancer. In another embodiment, an MMP-14 binding therapy is administered in combination with gemcitabine/oxaliplatin, or gemcitabine/erlotinib. In one embodiment, the combination therapy comprises DX-2400 and gemcitabine. Alternatively, the combination therapy comprises DX-2400 and gemcitabine/oxaliplatin, or DX-2400 and gemcitabine/erlotinib.

Reduce Side Effects of a Chemotherapeutic:

A combination therapy can include administering an MMP-14 binding agent and an additional therapeutic agent such that the side effects of one, or both, of the therapies are reduced. As but one example, an MMP-14 binding protein (e.g., DX-2400) can be administered in combination with a chemotherapeutic (e.g., gemcitabine, paclitaxel or darcabazine) to reduce the side effects (e.g., weight loss, inability to thrive) of the chemotherapeutic. Conversely, administration of a combination of an MMP-14 binding protein and an additional therapy can be used to reduce the side effects of an MMP-14 binding protein. Such reductions in side effects can be mediated, in part, by a lowering of the dose necessary to achieve a therapeutic effect of one or both of the agents in the combination.

Methods of administering MMP-14 binding proteins in combination with other agents are also described herein in sections titled "Pharmaceutical Compositions," and "Combination Therapy."

Pharmaceutical Compositions

In another aspect, the disclosure provides compositions comprising an MMP-14 binding protein, e.g., pharmaceutically acceptable compositions or pharmaceutical compositions, which include an MMP-14-binding protein. The MMP-14 binding protein can be formulated with a pharmaceutically acceptable carrier. Pharmaceutical compositions include therapeutic compositions and diagnostic compositions, e.g., compositions that include labeled MMP-14 binding proteins for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated. Depending on the route of administration, the MMP-14 binding protein described herein, may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the MMP-14 binding protein is administered by intravenous infusion or injection. In another preferred embodiment, the MMP-14 binding protein is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An MMP-14 binding protein can be administered by a variety of methods, although for many applications, the preferred route/mode of administration is intravenous injection or infusion. For example, for therapeutic applications, the MMP-14 binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an MMP-14 binding protein as described herein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, more preferably 1-10 mg/kg. An anti-MMP-14 antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. For binding proteins smaller in molecular weight than an antibody, appropriate amounts can be proportionally less. Dosage values may vary with the type and severity of the condition to be alleviated, and will also depend on the second therapeutic agent used in combination with the MMP-14 binding protein. For a particular subject, specific dosage regimens can be adjusted over time according to the individual need and the professional judgment of the person administering or supervising the administration of the compositions.

The pharmaceutical compositions disclosed herein may include a "therapeutically effective amount" or a "prophylactically effective amount" of an MMP-14 binding protein and, optionally, at least one additional agent disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition are outweighed by the therapeutically beneficial effects.

A "therapeutically effective dosage" preferably modulates a measurable parameter, e.g., levels of circulating IgG antibodies by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., a cancer (e.g., metastatic cancer, e.g., metastatic melanoma or pancreatic cancer), fibrin-invasive activity, angiogenesis, or capillary tube formation. Alternatively, this property of a composition can be evaluated by examining the ability of the compound to modulate a parameter in vitro.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Stabilization and Retention:

In one embodiment, an MMP-14 binding protein or second therapeutic agent is physically associated with a moiety that improves its stabilization and/or retention in circulation, e.g., in blood, serum, lymph, or other tissues, e.g., by at least 1.5, 2, 5, 10, or 50 fold. For example, one or more components of a combination therapy, e.g., a combination therapy described herein, can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an MMP-14 binding protein and/or an additional therapeutic agent can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

An MMP-14 binding protein and/or the additional therapeutic agent can also be associated with a carrier protein, e.g., a serum albumin, such as a human serum albumin. For example, a translational fusion can be used to associate the carrier protein with the MMP-14 binding protein.

Dosage and Administration

Provided herein are methods for treating cancer, or a related disorder, comprising administering an MMP-14 binding protein alone or in combination with one or more additional therapeutic agents. In one embodiment, the subject can be a mammal. In another embodiment, the mammal can be a human, although the approach is effective with respect to all mammals. The method comprises administering to the subject an effective amount of a pharmaceutical composition comprising an MMP-14 binding protein and, optionally, at least one additional agent (e.g., anti-cancer agent). Typically, one or both components of the combination therapy are provided in a pharmaceutically acceptable carrier, e.g., each component is individually provided in a pharmaceutically acceptable carrier.

The dosage range for an MMP-14 binding protein administered alone or the dosage range for each of the agents in a combination therapy depends upon the potency, and includes amounts large enough to produce the desired effect, e.g., a reduction in tumor growth rate or tumor volume. The dosage should not be so large as to cause unacceptable adverse side effects. Generally, the dosage will vary with the type of MMP-14 binding protein and/or the particular agent used, as well as with the age, condition, and sex of the patient. The dosage can be determined by one of skill in the art and can also be adjusted by the individual physician in the event of any complication. Typically, the dosage range for the MMP-14 binding protein is from 0.001 mg/kg body weight to 5 g/kg body weight. In some embodiments, the dosage range for the MMP-14 binding protein is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range for the MMP-14 binding protein is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range of the MMP-14 binding protein will be titrated to maintain serum levels between 5 µg/mL and 30 µg/mL.

In some embodiments, the MMP-14 binding protein is DX-2400 and is used in a dose range between 1 mg/kg and 100 mg/kg, preferably within the dose range of 10 mg/kg-50 mg/kg; 15 mg/kg-30 mg/kg, or 15 mg/kg-25 mg/kg. In one embodiment, the dosage of DX-2400 used in the methods described herein is about 20 mg/kg. In one embodiment, the additional therapeutic agent is darcabizine and is used in a dose range between about 1 mg/kg and 300 mg/kg; preferably in a range of 2 mg/kg-200 mg/kg, 3 mg/kg-100 mg/kg; 5 mg/kg-50 mg/kg, or 10 mg/kg-25 mg/kg. In one embodiment the dosage of darcabizine used to treat a subject having melanoma is about 1-5 mg/kg/day. In one embodiment, an MMP-14 binding protein, e.g., DX-2400, is administered in combination with darcabazine to treat melanoma (e.g., malignant melanoma). In some embodiments, the darcabazine is administered at a dose of 2 to 4.5 mg/kg/day, e.g., for 7, 8, 9, 10, 11, or 12 days. In another embodiment, the darcabazine is administered at a dose of 2 mg/kg/day or less (e.g., 1.5 mg/kg/day to 0.5 mg/kg/day, e.g., 1 mg/kg/day), e.g., for 7, 8, 9, 10, 11 or 12 days. The treatment with darcabizine can be repeated, e.g., every two to three weeks.

In one embodiment, the additional therapeutic agent is paclitaxel and is used in a dose range between about 0.1 mg/kg and 30 mg/kg; preferably in a range of 1.0 mg/kg-20 mg/kg, 2.5 mg/kg-15 mg/kg; 5.0 mg/kg-12.0 mg/kg, or 6 mg/kg-9 mg/kg. In one embodiment the dosage of paclitaxel used to treat a subject having melanoma is about 8 mg/kg. In one embodiment, an MMP-14 binding protein, e.g., DX-2400, is administered in combination with paclitaxel to treat melanoma (e.g., advanced or malignant melanoma). In some embodiments, the paclitaxel is administered at a dose of 135 to 175 mg/m$^2$, e.g., every three weeks. In another embodiment, the paclitaxel is administered at a dose less than 135 mg/m$^2$ (e.g., between 130 mg/m$^2$ to 100 mg/m$^2$), e.g., every three weeks.

In one embodiment, the additional therapeutic agent is gemcitabine and is used in a dose range between about 1 mg/kg and 300 mg/kg; preferably in a range of 10 mg/kg-200 mg/kg, 25 mg/kg-175 mg/kg; 25 mg/kg-100 mg/kg, or 30 mg/kg-60 mg/kg. In one embodiment the dosage of gemcitabine used to treat a subject having pancreatic cancer is about 50 mg/kg. In one embodiment, an MMP-14 binding protein, e.g., DX-2400, is administered in combination with gemcitabine to treat pancreatic cancer (e.g., locally advanced (nonresectable Stage II or Stage III) or metastatic pancreatic cancer). In some embodiments, gemcitabine is administered at a dose of 1000 mg/m$^2$, e.g., once a week. In another embodiment, gemcitabine is administered at a dose less than 1000 mg/m$^2$ (e.g., 950 to 700 mg/m$^2$, e.g., 900 to 800 mg/m$^2$), e.g., once a week.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Agents useful in the methods and compositions described herein can be administered intravenously (by bolus or continuous infusion), topically, orally, by inhalation, intraperitoneally, intramuscularly, subcutaneously, intracavity, and can be delivered by peristaltic means, if desired, or by other means known by those skilled in the art. It is preferred that the agents for the methods described herein are administered by infusion or injection. For the treatment of tumors, the agent can be administered systemically, or alternatively, can be administered directly to the tumor e.g., by intratumor injection or by injection into the tumor's primary blood supply.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The MMP-14 binding protein and/or the additional therapeutic agent is administered in a therapeutically effective amount. A therapeutically effective amount of an MMP-14 binding protein and/or the additional therapeutic agent is the amount which is effective, upon a single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition are outweighed by the therapeutically beneficial effects. A therapeutically effective dosage preferably modulates a measurable parameter, favorably, relative to untreated subjects. The ability of a compound to inhibit a measurable parameter can be evaluated in an animal model system predictive of efficacy in a human disorder.

In some embodiments, methods for treating cancer or a related disorder are provided herein, comprising administering an MMP-14 binding protein in combination with one or more additional therapeutic agents. By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. It will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

Similarly, the term "combination" refers to the use of the two or more agents or therapies to treat the same patient, wherein the use, or action, of the agents or therapies overlap in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of an MMP-14 binding protein described herein can also be used to reduce the dosage of another therapy, e.g., to reduce the side-effects associated with another agent that is being administered, e.g., to reduce the side-effects of gemcitabine. Accordingly, a combination can include administering a second agent at a dosage at least 10, 20, 30, or 50% lower than would be used in the absence of the MMP-14 binding protein.

Combination therapies comprising an MMP-14 binding agent and at least one additional agent as described herein can be used to reduce angiogenesis in a subject, e.g., to treat a cancer (e.g., a solid tumor) or an angiogenesis-associated disorder. The method includes administering the therapy to the subject, e.g., in an amount effective to modulate angiogenesis, a symptom of the disorder, or progression of the disorder. The combination therapy may be administered as a single bolus dose, as an infusion, or can be administered multiple times (e.g., at least two, three, five, or ten times) before a therapeutically effective amount is attained.

In one embodiment, the combination therapies described herein are used to inhibit an activity (e.g., inhibit at least one activity of, reduce proliferation, migration, growth or viability) of a cell, e.g., a cancer cell in vivo. The MMP-14 binding proteins can be conjugated to an agent, e.g., a cytotoxic drug, cytotoxin enzyme, or radioisotope. MMP-14 binding agents can be used to enhance delivery of the agent to MMP-14 associated cells or tissues by attaching an agent to the MMP-14 binding protein (e.g., a cytotoxic drug), prior to administering the combination therapy to a subject requiring such treatment.

The MMP-14 binding proteins described herein, e.g., anti-MMP-14 Fabs or IgGs, are administered in combination with one or more of the other therapies for treating a disease or condition associated with MMP-14 activity, e.g., a disease or condition described herein. For example, an MMP-14 binding protein can be used therapeutically or prophylactically with surgery, another MMP-14 inhibitor, e.g., a small molecule inhibitor, another anti-MMP-14 Fab or IgG (e.g., another Fab or IgG described herein), peptide inhibitor, chemotherapeutic agent, or small molecule inhibitor. Examples of MMP-14 inhibitors that can be used in combination therapy with an MMP-14 binding protein described herein include neovastat, marimastat, BAY 12-9566 and prinomastat.

One or more small-molecule MMP inhibitors can be used in combination with one or more MMP-14 binding proteins described herein. For example, the combination can result in a lower dose of the small-molecule inhibitor being needed, such that side effects are reduced.

The efficacy of a given treatment for an angiogenesis-associated disease can be determined by the skilled clinician. However, a treatment is considered "effective treatment," as the term is used herein, if any one or all of the signs or symptoms of, as but one example, of a cancer (e.g., tumor volume, tumor growth rate, metastasis) are altered in a beneficial manner, other clinically accepted symptoms or markers of disease are improved, or even ameliorated, e.g., by at least 10% following treatment with the MMP-14 binding protein alone, or as part of a combination therapy. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the pathogenic growth of a tumor; or (2) relieving the disease, e.g., causing regression of symptoms, reducing the tumor volume, tumor size or growth rate; and (3) preventing or reducing the likelihood of the development of a cancer, e.g., a metastatic cancer.

Selecting a Subject for Treatment with an MMP-14 Binding Protein or Combination Therapy In some embodiments, a subject is selected for treatment with an MMP-14 binding protein alone, or with a combination therapy comprising an MMP-14 binding protein and at least one additional therapeutic. For example, a subject having high MMP-14 expression and/or high MMP-2 activity can be selected for treatment with an MMP-14 binding protein or a combination therapy described herein. In one embodiment, the subject is identified or selected as likely or unlikely to respond to a treatment, e.g., an MMP-14 binding protein treatment as described herein. In some embodiments, the subject is refractory to treatment with one or more anti-cancer agents. In another embodiment, the subject is suffering from a relapse of a cancer e.g., pancreatic cancer or metastatic melanoma. In some embodiments, the subject has not received an anti-cancer treatment.

Identification or selection of a subject as likely or unlikely to respond to a treatment comprising an MMP-14 binding protein can be achieved using e.g., the MMP-14 binding proteins described herein, e.g., for in vivo imaging, e.g., prior to treatment, during a course of treatment for a disease or condition in which MMP-14 is active, e.g., a disease or condition described herein, or in diagnosing a disease or condition described herein. A subject can also be identified and/or selected for treatment with an MMP-14 binding protein or a combination therapy, by quantifying the expression or activity of MMP-14, MMP-9, TIMP-1, and/or MMP-2, as well as other biomarkers of cancer (e.g., CDKN2A). In some embodiments, an expressional ratio of MMP-14, MMP-9, TIMP-1, and/or MMP-2 can be used to determine the likelihood that a subject will respond to MMP-14 binding protein therapy. For example, expressional ratios of MMP-14/MMP-9, MMP-9/TIMP1, MMP-2/MMP-9, MMP-2/TIMP, or MMP-2/MMP-14 can be used to aid in selecting a patient for treatment with a therapy as described herein. Such methods are described in e.g., U.S. Application No. 2009/0203060 and in International Application No. WO 2009/079581, both of which are incorporated herein by reference in their entirety.

In one aspect, a subject is selected by using a method for detecting the presence of an MMP-14, in vitro or in vivo (e.g., in vivo imaging in a subject). The method can include localizing MMP-14 within a subject or within a sample from a subject. With respect to sample evaluation, the method can include, for example: (i) contacting a sample with MMP-14 binding protein; and (ii) detecting location of the MMP-14 binding protein in the sample.

An MMP-14 binding protein can also be used to determine the qualitative or quantitative level of expression of MMP-14 in a sample. The method can also include contacting a reference sample (e.g., a control sample) with the binding protein, and determining a corresponding assessment of the reference sample. A change, e.g., a statistically significant change, in the formation of the complex in the sample or subject relative to the control sample or subject can be indicative of the presence of MMP-14 in the sample. In one embodiment, the MMP-14 binding protein does not cross react with another metalloproteinase.

The MMP-14 binding proteins are also useful for in vivo tumor imaging. Imaging of tumors in vivo by using labeled MMP-14 binding proteins can help to target the delivery of the binding protein to tumors for cancer diagnosis, intraoperative tumor detection, and for investigations of drug delivery and tumor physiology. MMP-14 binding proteins can be used to monitor native enzymatic activity in vivo at invasive sites. Another exemplary method includes: (i) administering the MMP-14 binding protein to a subject; and (iii) detecting location of the MMP-14 binding protein in the subject. The detecting can include determining location or time of formation of the complex.

The MMP-14 binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the MMP-14 binding protein and MMP-14 can be detected by evaluating the binding protein bound to the MMP-14 or unbound binding protein. Conventional detection assays can be used, e.g., an enzyme-linked immunosorbent assays (ELISA), a radioimmunoassay (RIA) or tissue immunohistochemistry. Further to labeling the MMP-14 binding protein, the presence of MMP-14 can be assayed in a sample by a competition immunoassay utilizing standards labeled with a detectable substance and an unlabeled MMP-14 binding protein. In one example of this assay, the biological sample, the labeled standards, and the MMP-14 binding protein are combined and the amount of labeled standard bound to the unlabeled binding protein is determined. The amount of MMP-14 in the sample is inversely proportional to the amount of labeled standard bound to the MMP-14 binding protein.

Fluorophore and chromophore labeled proteins can be prepared. Because antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, 1968, Science 162:526 and Brand, L. et al., 1972, Annu. Rev. Biochem. 41:843-868. The proteins can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein can be used to detect the presence or localization of the MMP-14 in a sample, e.g., using fluorescent microscopy (such as confocal or deconvolution microscopy).

Histological Analysis.

Immunohistochemistry can be performed on e.g., a sample obtained from the subject (e.g., a tissue sample, a biopsy sample etc) using the proteins described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays.

The MMP-14 binding protein can also be immobilized on a protein array. The protein array can be used as a diagnostic tool, e.g., to screen medical samples (such as isolated cells, blood, sera, biopsies, and the like). Of course, the protein array can also include other binding proteins, e.g., that bind to MMP-14 or to other target molecules.

Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, I-VII; MacBeath and Schreiber, 2000, Science 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the proteins can be grown on a filter in an arrayed format. Polypeptide production is induced, and the expressed polypeptides are immobilized to the filter at the location of the cell. A protein array can be contacted with a labeled target to determine the extent of binding of the target to each immobilized polypeptide. Information about the extent of binding at each address of the array can be stored as a profile, e.g., in a computer database. The protein array can be produced in replicates and used to compare binding profiles, e.g., of a target and a non-target.

FACS (Fluorescence Activated Cell Sorting).

The MMP-14 binding protein can be used to label cells, e.g., cells in a sample (e.g., a patient sample). The binding protein is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the binding protein from those cells not bound by the binding protein. The separated cells can be cultured and/or characterized.

In Vivo Imaging.

Also featured is a method for detecting the presence of an MMP-14 protein or MMP-2 protein expression or activity in a tissue in vivo. For example, the method includes (i) administering to a subject (e.g., a patient having, e.g., a cancer (e.g., metastatic cancer, e.g., metastatic melanoma) an anti-MMP-14 antibody, conjugated to a detectable marker; (ii) exposing the subject to a means for detecting said detectable marker to the MMP-14 expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The protein can be labeled with such reagents; for example, see Wensel and Meares, 1983, *Radioimmunoimaging and Radioimmunotherapy*, Elsevier, New York for techniques relating to the radiolabeling of antibodies and D. Colcher et al., 1986, *Meth. Enzymol.* 121: 802-816.

The binding protein can be labeled with a radioactive isotope (such as $^{14}$C, $^{3}$H, $^{32}$S, $^{131}$I, $^{32}$P, $^{131}$I). A radiolabeled binding protein can be used for diagnostic tests, e.g., an in vitro assay. The specific activity of an isotopically-labeled binding protein depends upon the half life, the isotopic purity of the radioactive label, and how the label is incorporated into the antibody.

In the case of a radiolabeled binding protein, the binding protein is administered to the patient, is localized to cells bearing the antigen with which the binding protein reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents.

Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The MMP-14 binding protein can also be labeled with an indicating group containing of the NMR active $^{19}$F atom, or a plurality of such atoms inasmuch as (i) substantially all of naturally abundant fluorine atoms are the $^{19}$F isotope and, thus, substantially all fluorine containing compounds are NMR active; (ii) many chemically active polyfluorinated compounds such as trifluoracetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing MMP-14.

Design and Selection of MMP-14 Binding Proteins

MMP-14 antibodies can be designed and/or identified using methods known to those of skill in the art, including, e.g., the use of display libraries e.g., a phage display library. Such methods are well known to those of skill in the art (see e.g., U.S. Pat. No. 7,745,587 or US2010/0266490, both of which are incorporated by reference in their entirety) and/or described briefly herein. In some embodiments, an MMP-14 binding protein is selected from a display library, for example, the polypeptide component of each member of the library is probed with MMP-14 (e.g., the catalytic domain of MMP-14 or other fragment) and if the polypeptide component binds to the MMP-14, the display library member is identified, typically by retention on a support. Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

Library Formats:

A variety of formats can be used for display libraries and are known to those of skill in the art. For example, a phage display library can be used to display binding proteins. Phage display is described, for example, in US2010/0266490, U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3):344-8. Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958). Other types of collections of proteins (e.g., expression libraries) can be used to identify proteins with a particular property (e.g., ability to bind MMP-14 and/or ability to modulate MMP-14), including, e.g., protein arrays of antibodies (see, e.g., De Wildt et al. (2000) *Nat. Biotechnol.* 18:989-994), lambda gt11 libraries, two-hybrid libraries and so forth.

Scaffolds:

Scaffolds useful for display include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., US 2004-0005709.

Iterative Selection.

In one preferred embodiment, display library technology is used in an iterative mode. A first display library is used to identify one or more binding proteins for a target. These identified binding proteins are then varied using a mutagenesis method to form a second display library. Higher affinity binding proteins are then selected from the second library, e.g., by using higher stringency or more competitive binding and washing conditions. Iterative selection is described in detail in e.g., U.S. Pat. No. 7,745,587.

Identifying High Affinity MMP-14 Binding Proteins.

Antibodies having a slow dissociation rate (e.g., predictive of high affinity) can be identified using methods that isolate binding proteins with a desired (e.g., reduced) kinetic dissociation rate for a binding interaction to a target. Briefly, antibodies are first contacted with an immobilized target, and followed with a wash solution to remove non-specifically or weakly bound binding proteins. The bound binding proteins are eluted with a solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The elution solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity.

Binding proteins that interact with non-target molecules such as streptavidin on magnetic beads, blocking agents such as bovine serum albumin, non-fat bovine milk, any capturing or target immobilizing monoclonal antibody, or non-transfected cells which do not express the human MMP-14 target, can be removed using e.g., a negative selection step. Typically, the display library or a pool thereof is contacted with a non-target molecule. Binding proteins that do not bind the non-target are collected and used in subsequent selections for binding to the target molecule or even for subsequent negative selections. The negative selection step can be prior to or after selecting library members that bind to the target molecule.

Alternatively, a screening step can be used to remove binding proteins that interact with non-target molecules. After display library members are isolated for binding to the target molecule, each isolated library member is tested for its ability to bind to a non-target molecule using e.g., a high-throughput ELISA screen. The ELISA screen can also be used to obtain quantitative data for binding of each library member to the target as well as for cross species reactivity to related targets or subunits of the target (e.g., mouse MMP-14) and also under different conditions such as varying pH (e.g., pH 6 or pH 7.5). The non-target and target binding data are compared (e.g., using a computer and software) to identify library members that specifically bind to the target.

Primate Antibodies:

In some embodiments, a primate MMP-14 binding protein is preferred. Non-human primate libraries can be used in combination with phage display to select MMP-14 antibodies that can be used in immunization of a chimpanzee or macaque to prepare a primatized antibody. See, for example, Vaccine. (2003) 22(2):257-67 or Immunogenetics. (2005) 57(10):730-8. One can also make chimeras of primatized Fabs with human constant regions, see Curr Opin Mol Ther. (2004) 6(6):675-83. "PRIMATIZED" antibodies, genetically engineered from cynomolgus macaque monkey and human components, are structurally indistinguishable from human antibodies. They may, therefore, be less likely to cause adverse reactions in humans, making them potentially suited for long-term, chronic treatment see e.g., Curr Opin Investig Drugs. (2001) 2(5):635-8.

Human or Humanized Antibodies:

In addition, human or humanized immunoglobin domain libraries may be used to identify human or "humanized" antibodies that, for example, recognize human antigens. Because the constant and framework regions of the antibody are human, these antibodies may avoid themselves being recognized and targeted as antigens when administered to humans. The constant regions may also be optimized to recruit effector functions of the human immune system. The in vitro display selection process surmounts the inability of a normal human immune system to generate antibodies against self-antigens.

In addition to the use of display libraries, other methods can be used to obtain an MMP-14 binding antibody. For example, an MMP-14 protein or a region thereof can be used as an antigen in a non-human animal, e.g., a rodent, wherein the non-human animal includes at least a part of a human immunoglobulin gene. For example, mouse strains deficient in mouse antibody production can be engineered with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Antibody Library Construction:

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay, 1988, *Ann. Rev. Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, *J. Biol. Chem.* 274:18218-30; Hoogenboom et al., 1998, *Immunotechnology* 4:1-20; Hoogenboom et al., 2000, *Immunol. Today* 21:371-378, and Hoet et al. (2005) *Nat Biotechnol.* 23(3): 344-8. The use of antibody libraries for the design and identification of MMP-14 binding proteins is described in detail in e.g., U.S. Pat. No. 7,745,587.

In some embodiments, nucleic acids encoding immunoglobulin domains can be obtained from human immune cells, e.g., B cells. Such immune cells can be isolated from a subject that has a disease or condition described herein, e.g., a cancer (e.g., pancreatic cancer or a metastatic cancer, e.g., metastatic melanoma), and inappropriate angiogenesis. In one embodiment, the cells are isolated from a subject having metastatic melanoma, or pancreatic cancer. These methods are described in detail in e.g., U.S. Pat. No. 7,745,587 or US 2010/0266490.

Secondary Screening Methods of MMP-14 Binding Proteins

After selecting candidate library members that bind to a target, each candidate library member can be further analyzed, e.g., to further characterize its binding properties for the target, e.g., MMP-14, or for binding to other protein, e.g., another metalloproteinase. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties include the following. Exemplary assays for selecting a library member having a desired property include e.g., ELISA, a homogeneous binding assay (e.g., fluorophore resonance energy transfer (FRET), ALPHASCREEN™ (Packard Bioscience, Meriden Conn.)), Surface Plasmon Resonance (SPR), or cellular assays. Such methods are known to those of skill in art and/or are described in e.g., US 2010/0266490, Lakowicz et al., U.S. Pat. No. 5,631,169; Stavrianopoulos, et al., U.S. Pat. Nos. 4,868,103, 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Reducing Immunogenicity of MMP-14 Binding Proteins

Immunoglobin MMP-14 binding proteins (e.g., IgG or Fab MMP-14 binding proteins) described herein may be modified to reduce immunogenicity. Reduced immunogenicity is desirable in MMP-14 binding proteins intended for use as therapeutics, as it reduces the chance that the subject will develop an immune response against the therapeutic molecule. Techniques useful for reducing immunogenicity of MMP-14 binding proteins include deletion/modification of potential human T cell epitopes and 'germlining' of sequences outside of the CDRs (e.g., framework and Fc). Such methods are known in the art and are described in e.g., U.S. Pat. No. 7,745,587.

Deletion of T-Cell Epitopes:

An MMP-14-binding antibody may be modified by specific deletion of human T cell epitopes or "deimmunization" by the methods disclosed in e.g., WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Wherever possible, potential T cell epitopes that overlap the CDRs should be eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Germlining MMP-14 Antibodies:

MMP-14 binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to MMP-14, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. Exemplary germlining methods are described in e.g., U.S. Pat. No. 7,745, 587. In one embodiment, as many germline residues are introduced into an isolated antibody as possible.

An antibody which has similar activity to a given antibody of interest can be selected based on it similarity to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the international ImMunoGeneTics information System® (IMGT), available via the world wide web at imgt.cines.fr, and the V BASE directory (compiled by Tomlinson, I. A. et al. MRC Centre for Protein Engineering, Cambridge, UK, available via the world wide web at vbase.mrc-cpe.cam.ac.uk).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

MMP-14 Binding Proteins: Protein Production

Standard recombinant nucleic acid methods can be used to express a protein that binds to MMP-14. Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Antibody Production.

Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), *Hanseula*, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, HEK293T cells (*J. Immunol. Methods* (2004) 289(1-2):65-80.), and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Characterization of MMP-14 Binding Proteins

Binding of MMP-14 binding proteins to cells expressing MMP-14 and/or MMP-2 can be characterized in a number assays known in the art, including FACS (Fluorescence Activated Cell Sorting), immunofluorescence, and immunocytochemistry. MMP-14 binding protein is contacted with cells and/or tissues which express or contain MMP-14, and binding is detected in accordance with the method being used.

In one embodiment, MMP-14 binding proteins are characterized as to cellular binding by FACS (Fluorescence Activated Cell Sorting) using cells expressing MMP-14. MMP-14 binding proteins can also be characterized in cultured cells expressing the MMP-14 antigen using immunocytochemistry. Methods for FACS sorting of labeled cells or immunocytochemistry are well known to those of skill in the art and/or are described in e.g., U.S. Pat. No. 7,745,587.

MMP-14 binding proteins can be characterized in assays that measure their modulatory activity toward MMP-14 or fragments thereof in vitro or in vivo. For example, MMP-14 can be combined with a substrate such as Mca-Pro-Leu-Ala-Cys(Mob)-Trp-Ala-Arg-Dap(Dnp)-NH$_2$ (SEQ ID NO: 53) under assay conditions permitting cleavage by MMP-14. The assay is performed in the absence of the MMP-14 binding protein, and in the presence of increasing concentrations of the MMP-14 binding protein. The concentration of binding protein at which 50% of the MMP-14 activity (e.g., binding to the substrate) is inhibited is the IC$_{50}$ value (Inhibitory Concentration 50%) or EC$_{50}$ (Effective Concentration 50%) value for that binding protein. Within a series or group of binding proteins, those having lower IC$_{50}$ or EC$_{50}$ values are considered more potent inhibitors of MMP-14 than those binding proteins having higher IC$_{50}$ or EC$_{50}$ values. Exemplary binding proteins have an IC$_{50}$ value of less than 800 nM, 400 nM, 100 nM, 25 nM, 5 nM, or 1 nM, e.g., as measured in an in vitro assay for inhibition of MMP-14 activity when the MMP-14 is at 2 pM.

MMP-14 binding proteins may also be characterized with reference to the activity of MMP-14 on its substrates (e.g., activation of cell surface pro-MMP-2). Cleavage of cell surface pro-MMP-2 by MMP-14 releases active MMP-2, which can be detected by zymography. The method is based on a SDS gel impregnated with a protein substrate, which is degraded by the proteases resolved during the incubation period. Coomassie blue staining of the gels reveals proteolytic fragments as white bands on a dark blue background. Within a certain range, the band intensity can be related linearly to the amount of the protease loaded. Cells expressing both MMP-14 and MMP-2 are used in this assay. The assay is performed in the absence of the MMP-14 binding protein, and in the presence of increasing concentrations of the MMP-14 binding protein. The concentration of binding protein at which 50% of the MMP-2 activity (e.g., binding to the substrate) is inhibited is the IC$_{50}$ value (Inhibitory Concentration 50%) or EC$_{50}$ (Effective Concentration 50%) value for that binding protein. Within a series or group of binding proteins, those having lower IC$_{50}$ or EC$_{50}$ values are considered more potent inhibitors of MMP-14 than those binding proteins having higher IC$_{50}$ or EC$_{50}$ values. Exemplary binding proteins have an IC$_{50}$ value of less than 800 nM, 400 nM, 100 nM, 25 nM, 5 nM, or 1 nM, e.g., as measured in an in vitro assay for inhibition of MMP-14 activity.

The binding proteins can also be evaluated for selectivity toward MMP-14. For example, a MMP-14 binding protein can be assayed for its potency toward MMP-14 and a panel of MMPs and other enzymes, e.g., MMP-1, -2, -3, -7, -8, -9, -12, -13, -16, -17, -24, and TACE, and an $IC_{50}$ value or $EC_{50}$ value can be determined for each MMP. In one embodiment, a compound that demonstrates a low $IC_{50}$ value or $EC_{50}$ value for the MMP-14, and a higher $IC_{50}$ value or $EC_{50}$ value, e.g., at least 2-, 5-, or 10-fold higher, for another MMP within the test panel (e.g., MMP-1, -10) is considered to be selective toward MMP-14.

MMP-14 binding proteins can be evaluated for their ability to inhibit MMP-14 in a cell based assay. The expansion of tumor cells inside a three-dimensional collagen-matrix can be significantly enhanced in response to MMP-14 overexpression (Hotary et al., 2003 Cell 114:33-45). Addition of an MMP-14 binding protein to this assay can be used to determine the inhibitory properties and other characteristics of the protein.

A pharmacokinetics study in rat, mice, or monkey can be performed with MMP-14 binding proteins for determining MMP-14 half-life in the serum. Likewise, the effect of the binding protein can be assessed in vivo, e.g., in an animal model for a disease, for use as a therapeutic, for example, to treat a disease or condition described herein, e.g., a cancer (e.g., metastatic cancer, e.g., metastatic melanoma or pancreatic cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation.

Kits

Ann MMP-14 binding protein described herein can be provided in a kit, e.g., as a component of a kit. In some embodiments, the kit can further comprise at least one additional therapeutic agent, e.g., a combination therapy described herein. For example, the kit includes (a) an MMP-14 binding protein, e.g., a composition that includes an MMP-14 binding protein, optionally, (b) at least one additional agent (e.g., an anti-cancer agent) and, optionally (c) informational material. The informational material can be descriptive, instructional, marketing or other material that relates to the methods described herein, e.g., for treatment of melanoma or pancreatic cancer, and/or the use of an MMP-14 binding protein in combination with at least one additional agent as described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the binding protein to treat, prevent, or diagnosis of disorders and conditions, e.g., a cancer, e.g., melanoma or pancreatic cancer (e.g., metastatic cancer, e.g., metastatic melanoma or pancreatic cancer), inappropriate angiogenesis, or capillary tube formation.

In one embodiment, the informational material can include instructions to administer an MMP-14 binding protein combination therapy in a suitable manner to perform the methods described herein, e.g., in a suitable dose, dosage form, or mode of administration (e.g., a dose, dosage form, or mode of administration described herein). In another embodiment, the informational material can include instructions to administer an MMP-14 binding protein to a suitable subject, e.g., a human, e.g., a human having, or at risk for, a disorder or condition described herein, e.g., a cancer, e.g., melanoma or pancreatic cancer (e.g., metastatic cancer, e.g., metastatic melanoma or pancreatic cancer), inappropriate angiogenesis, or capillary tube formation. For example, the material can include instructions to administer a combination therapy comprising an MMP-14 binding protein to a patient with a disorder or condition described herein, e.g., a cancer (e.g., metastatic cancer, e.g., metastatic melanoma or pancreatic cancer), inappropriate angiogenesis, or capillary tube formation. The informational material of the kits is not limited in its form. In many cases, the informational material, e.g., instructions, is provided in print but may also be in other formats, such as computer readable material.

An MMP-14 binding protein and/or an additional agent can be provided in any form, e.g., liquid, dried or lyophilized form. It is preferred that each component of the combination therapy be substantially pure and/or sterile. When an MMP-14 binding protein or additional agent is provided in a liquid solution, the liquid solution preferably is an aqueous solution, with a sterile aqueous solution being preferred. When an MMP-14 binding protein and/or additional agent is provided as a dried form, reconstitution generally is by the addition of a suitable solvent. The solvent, e.g., sterile water or buffer, can optionally be provided in the kit.

The kit can include one or more containers for the composition containing an MMP-14 binding protein and/or at least one additional therapeutic agent. In some embodiments, the kit contains separate containers, dividers or compartments for the composition and informational material. For example, the composition can be contained in a bottle, vial, or syringe, and the informational material can be contained association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an MMP-14 binding protein and/or a second therapeutic agent. For example, the kit includes a plurality of syringes, ampules, foil packets, or blister packs, each containing a single unit dose of an MMP-14 binding protein and/or the second therapeutic agent. The containers of the kits can be air tight, waterproof (e.g., impermeable to changes in moisture or evaporation), and/or light-tight.

The kit optionally includes a device suitable for administration of the composition, e.g., a syringe, inhalant, dropper (e.g., eye dropper), swab (e.g., a cotton swab or wooden swab), or any such delivery device. In one embodiment, the device is an implantable device that dispenses metered doses of the binding protein. The disclosure also features a method of providing a kit, e.g., by combining components described herein.

The contents of all references, pending patent applications and published patents, cited throughout this application are hereby expressly incorporated by reference. The following examples provide further illustrate and are not limiting.

EXAMPLES

Example 1: Combination Treatment of Human Melanoma Using DX-2400 and Darcabazine The in vivo therapeutic efficacy of DX-2400 as a single agent or in combination with darcabazine was determined using a subcutaneous A375 human melanoma xenograft model.

A375 tumor cells were maintained in vitro as a monolayer culture in DMEM medium, supplemented with 10% heat inactivated fetal bovine serum, 100 U/ml penicillin and 100 µg/ml streptomycin, and L-glutamine (2 mM) at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

55 BALB/c nude, female, 6-8 weeks, weighing approximately 18-22 were purchased from Shanghai Laboratory Animal Center SLAC (Shanghai, China) for use in the study (40 mice+~40% spare). Each mouse was inoculated subcutaneously at the right flank with A375 tumor cells ($5 \times 10^6$) in 0.1 ml of PBS for tumor development. The treatments were started when the mean tumor size reached approximately 150~200 mm³. Each group consisted of 10 mice. Tumor-bearing were divided into four treatment groups as shown in Table 4.

TABLE 4

Treatment groups for testing a combination therapy comprising DX-2400 and darcabazine for the treatment of human melanoma.

| Group | n | Treatment | Dose (mg/kg) | Dosing Route | Schedule |
|---|---|---|---|---|---|
| 1 | 10 | Vehicle | — | i.v. | Q3D X6 |
| 2 | 10 | DX-2400 | 20 | i.v. | Q3D X6 |
| 3 | 10 | Darcabazine | 150 | i.p. | Day 1, 4/wk x 3 |
| 4 | 10 | DX-2400 | 20 | i.v. | Q3D X6 |
|   |   | Darcabazine | 150 | i.p. | Day 1, 4/wk x 3 | n: animal number;
Dosing volume: adjust dosing volume based on body weight (10 µl/g).

FIG. 1A shows tumor size over time for each of Groups 1-4 in a mouse xenograft model of human metastatic myeloma. Treatment with DX-2400 alone or treatment with darcabazine alone reduced tumor volume compared to the volume of tumors in untreated mice. In addition, the combination treatment of DX-2400 with darcabazine was more effective at reducing tumor volume than either agent alone.

In addition, administration of DX-2400 alone caused a reduction in the tumor growth rate compared to untreated mice. Similarly, administration of darcabazine alone also caused a reduction in tumor growth rate as compared to tumor growth rates in untreated mice. Combination treatment of mice with both DX-2400 and darcabazine reduced tumor growth rates to a greater degree than either agent alone.

Example 2: Combination Therapy of Human Melanoma with DX-2400 and Paclitaxel

The in vivo therapeutic efficacy of DX-2400 as a single agent or in combination with Paclitaxel in the treatment of human melanoma was evaluated using a subcutaneous SK-MEL-5 human melanoma xenograft model.

SK-MEL-5 human melanoma cells were grown in EMEM medium, supplemented with 10% heat inactivated fetal bovine serum, 100 U/ml penicillin and 100 µg/ml streptomycin at 37° C. in an atmosphere of 5% $CO_2$ in air. The tumor cells were routinely subcultured twice weekly. Cells were harvested during the logarithmic growth period and resuspended in physical PBS with proper cell concentration and kept on ice for tumor induction.

55 BALB/c nude, female, 6-8 weeks, weighing approximately 18-22 g (40 mice+~40% spare) were used for the study. Animals were purchased from Shanghai Laboratory Animal Center SLAC (Shanghai, China, Shanghai). Each mouse was inoculated subcutaneously at the right flank with SK-MEL-5 tumor cells ($5 \times 10^6$) in 0.1 ml of PBS for tumor development. The treatments were started when the mean tumor size reached approximately 150~200 mm³. Each group consisted of 10 mice. Tumor-bearing mice were assigned to four different treatment groups as shown in the following table.

TABLE 5

Treatment groups for testing a efficacy of an MMP-14 binding protein alone or as part of a combination therapy comprising DX-2400 and paclitaxel for the treatment of human melanoma.

| Group | n | Treatment | Dose (mg/kg) | Dosing Route | Schedule |
|---|---|---|---|---|---|
| 1 | 10 | Vehicle | — | i.v. | Q3D X6 |
| 2 | 10 | DX-2400 | 20 | i.v. | Q3D X6 |
| 3 | 10 | Paclitaxel | 8 | i.p. | Q4D X6 |
| 4 | 10 | DX-2400 | 20 | i.v. | Q3D X6 |
|   |   | Paclitaxel | 8 | i.p. | Q4D X6 | n: animal number;
Dosing volume: adjust dosing volume based on body weight (10 µl/g).

Figure 2:
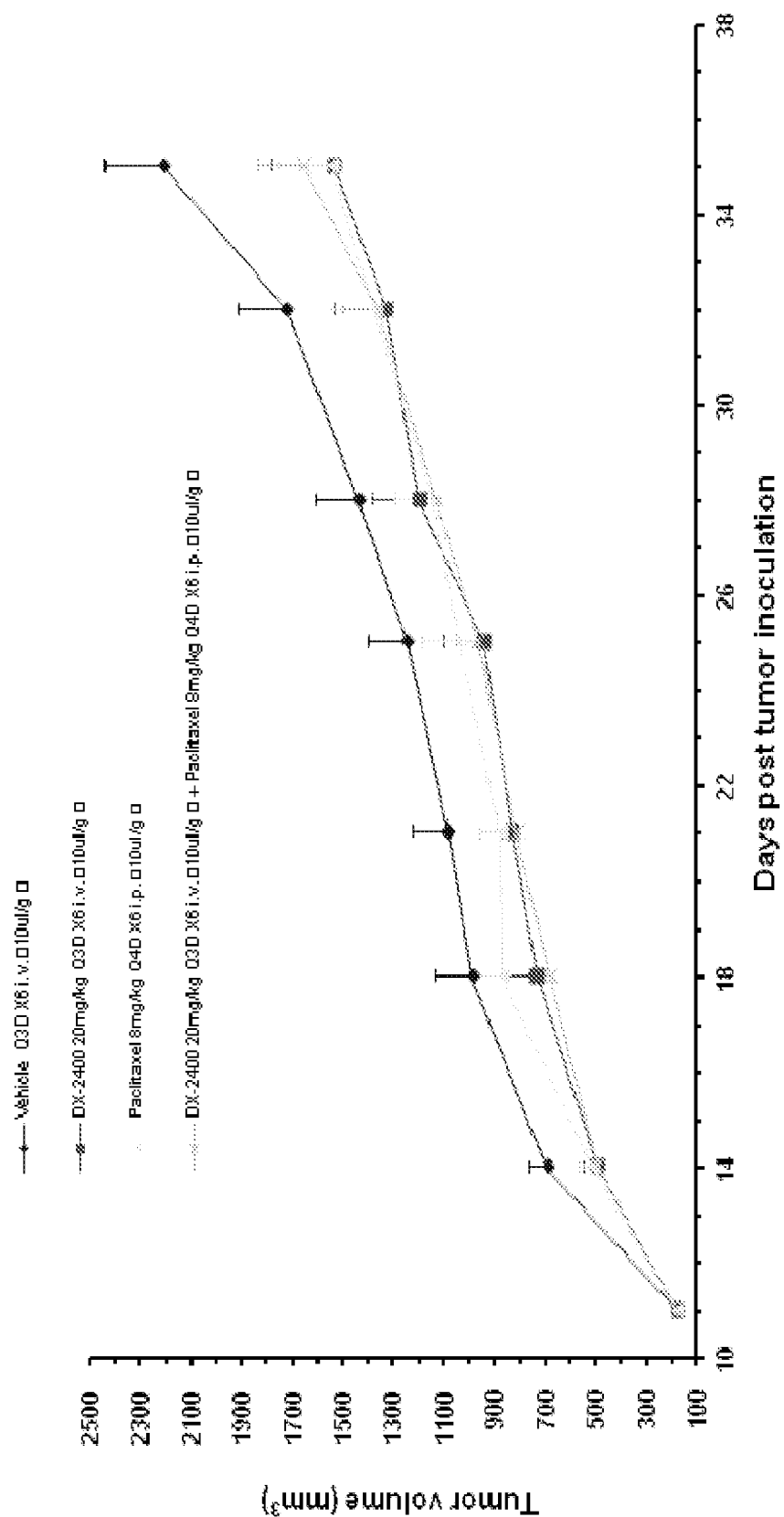
FIG. 2 is a graph showing the effect of anti-cancer treatment on tumor volume in a xenograft mouse model of human melanoma (SK-MEL-5 cells). Animals were treated with DX-2400 alone, paclitaxel alone, and a combination of paclitaxel and DX-2400.

FIG. 2A shows tumor size over time for each of Groups 1-4 in a mouse xenograft model of human metastatic myeloma (SK-MEL-5 cells). Treatment with DX-2400 alone or treatment with paclitaxel alone reduced tumor volume compared to the volume of tumors in untreated mice. In addition, the combination treatment of DX-2400 with darcabazine also reduced tumor volume compared to that of untreated mice.

In addition, administration of DX-2400 alone caused a reduction in the tumor growth rate as compared to tumor growth rate in untreated mice. Similarly, administration of paclitaxel alone also caused a reduction in tumor growth rate as compared to tumor growth rates in untreated mice. Combination treatment of mice with both DX-2400 and darcabazine reduced tumor growth rates compared to untreated mice.

Example 3: MMP-14 Binding Protein Single Agent Treatment or Combination Treatment of Human Pancreatic Cancer (PAM527 Tumor Fragment) Using DX-2400 and/or Gemcitabine The in vivo anti-tumor activity of DX-2400 as a single agent or in combination with gemcitabine was evaluated in the treatment of subcutaneous primary human pancreatic cancer using a PAM527 xenograft model in nude mice.

75 BALB/c nude mice, female, 6-8 weeks, weighing approximately 18-24 g were purchased from SLAC, Shanghai, P. R. China (40 mice+~90% spare). Tumor fragments from seed mice inoculated with selected primary human pancreatic cancer tissues (PAM527) were harvested and used for inoculation into BALB/c nude mice. Each mouse was inoculated subcutaneously at the right flank with one tumor fragment (2-3 mm in diameter) for tumor development. The treatments were started when the mean tumor size reached approximately 150 mm³. Each group consisted of 10 mice. The tumor-bearing mice were divided into four treatment groups, as shown in Table 6.

TABLE 6

Treatment groups for testing an MMP-14 binding protein alone, or as part of a combination therapy for the treatment of human pancreatic cancer.

| Group | n | Treatment | Dose (mg/kg) | Dosing Route | Dosing volume | Schedule |
|---|---|---|---|---|---|---|
| 1 | 10 | Vehicle | — | i.v. | 10 µL/g | Q3d × 6 |
| 2 | 10 | DX-2400 | 20 | i.v. | 10 µL/g | Q3d × 6 |
| 3 | 10 | Gemcitabine | 60 | i.p. | 10 µL/g | Q4d × 4 |
| 4[a] | 10 | DX-2400 (Dosing first) | 20 | i.v. | 10 µL/g | Q3d × 6 |
|   |   | Gemcitabine | 0 | i.p. | 10 µL/g | Q4d × 4 | n: animal number
Dosing volume: adjust dosing volume based on body weight (10 µl/g).
[a]The combination dosing: dosing the DX-2400 first prior to the Gemcitabine and a few minutes in between was sufficient.

Tumors were harvested at study endpoint. Tumor tissues were cut in half with ½ being frozen in liquid nitrogen and the other half being placed in 10% neutral buffered formalin for 16-24 hours and then transferred to 70% ethanol.

Figure 3A:
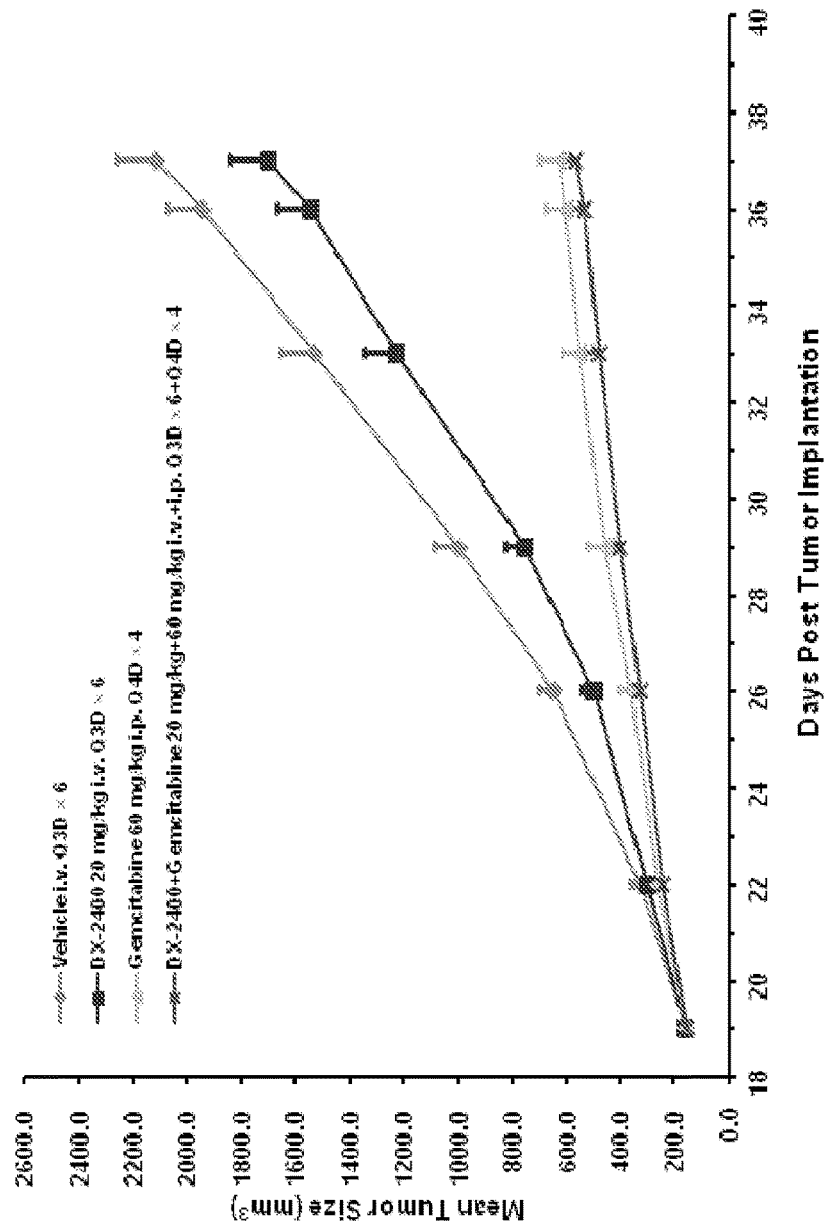
FIGS. 3A and 3B are graphs showing the effect of anti-cancer treatment on mean tumor volume (FIG. 3A) and mean body weight (FIG. 3B) in a xenograft mouse model of pancreatic cancer (PAM27 cells). Animals were treated with DX-2400 alone, gemcitabine alone, and a combination of gemcitabine and DX-2400.

FIG. 3A shows the mean tumor size over time for each of Groups 1-4 in a mouse xenograft model of human pancreatic cancer (PAM27 cells). Treatment with DX-2400 alone reduced the mean tumor size as compared to the tumor size observed in untreated mice. Similarly, gemcitabine solo administration also reduced the tumor size as compared to tumor size in untreated mice. In addition, the combination treatment of DX-2400 with gemcitabine also reduced tumor volume compared to that of untreated mice.

Figure 3B:
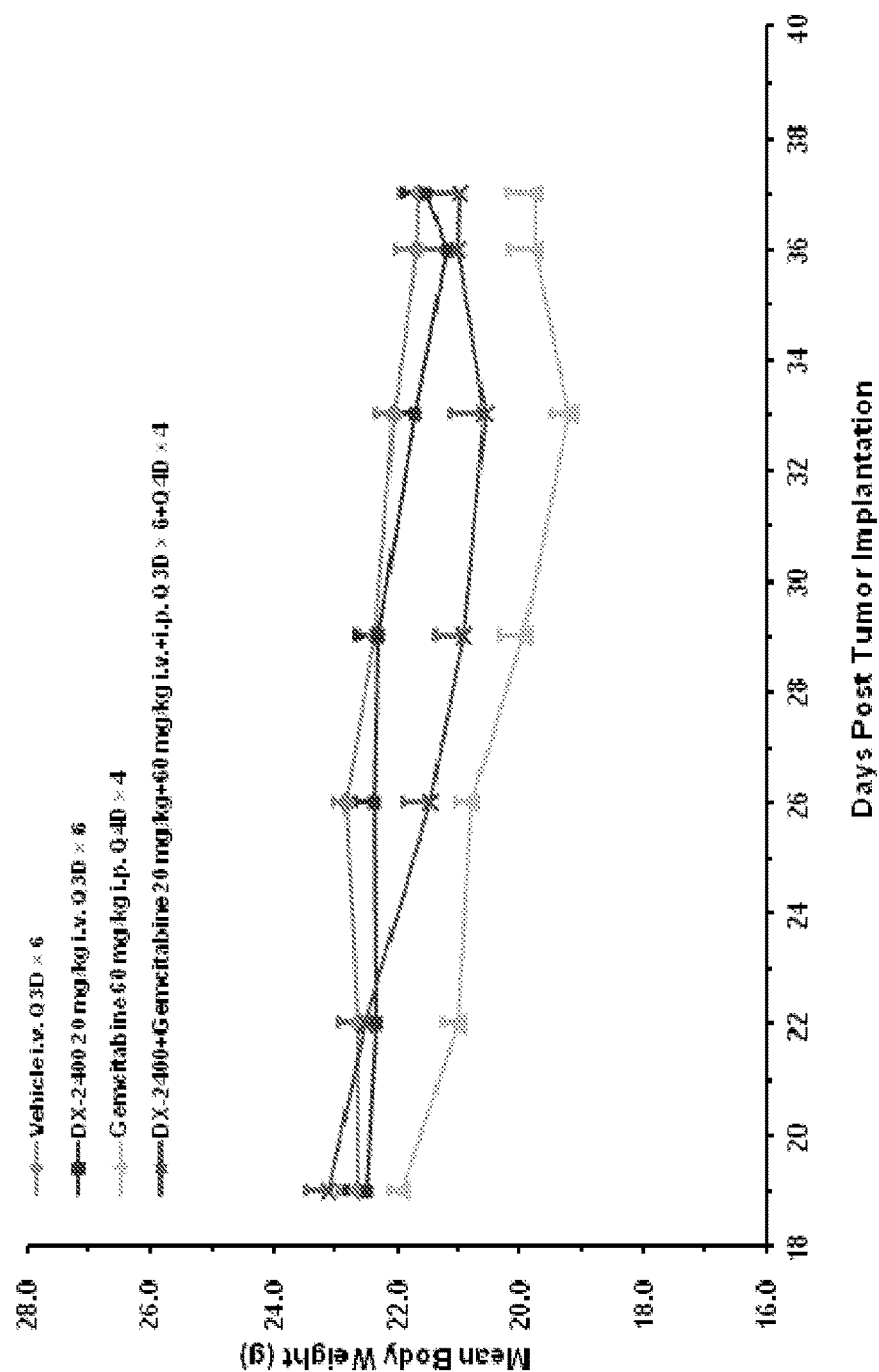

FIG. 3B shows the effect of the different treatments on mean body weight over time. Administration of DX-2400 alone had little effect on the mean body weight as compared to untreated mice. However, administration of gemcitabine alone caused a reduction body weight as compared to body weights of untreated mice. Combination treatment of mice with both DX-2400 and gemcitabine attenuated the drop in body weight associated with gemcitabine solo treatment.

Example 4: MMP-14 Binding Protein Single Agent Treatment or Combination Treatment of Human Pancreatic Cancer (Panc-1 Cells) Using DX-2400 and/or Gemcitabine The in vivo therapeutic efficacy of DX-2400 as a single agent or in combination with gemcitabine was evaluated in the treatment of a subcutaneous Panc-1 human pancreas cancer xenograft model.

Panc-1 tumor cells were maintained in vitro as a monolayer culture in DMEM medium, supplemented with 10% heat inactivated fetal bovine serum, 100 U/ml penicillin and 100 µg/ml streptomycin, and L-glutamine (2 mM) at 37° C. in an atmosphere of 5% $CO_2$ in air. The tumor cells will be routinely subcultured twice weekly by trypsin-EDTA treatment. The cells growing in an exponential growth phase will be harvested and counted for tumor inoculation.

A total of 56 (40 plus 40% spare) BALB/c nude, female, 6-8 weeks, weighing approximately 18-22 g were purchased from Shanghai Laboratory Animal Center SLAC (Shanghai, China) for use in the study. Each mouse was inoculated subcutaneously at the right flank with Panc-1 tumor cells ($5×10^6$) in 0.1 ml of PBS for tumor development. The treatments were started when the mean tumor size reached approximately 150~200 mm$^3$. Each group consisted of 10 mice. The tumor-bearing mice were divided into four treatment groups, as shown in Table 7.

TABLE 7

Treatment groups for testing an MMP-14 binding protein alone, or as part of a combination therapy for the treatment of human pancreatic cancer.

| Group | n | Treatment | Dose (mg/kg) | Dosing Route | Schedule |
|---|---|---|---|---|---|
| 1 | 10 | Vehicle | — | i.v. | Q3D X6 |
| 2 | 10 | DX-2400 | 20 | i.v. | Q3D X6 |
| 3 | 10 | Gemcitabine | 50 | i.p. | Q3D X4 |
| 4 | 10 | DX-2400 | 20 | i.v. | Q3D X6 |
|   |   | Gemcitabine | 50 | i.p. | Q3D X4 | n: animal number
Dosing volume: adjust dosing volume based on body weight (10 µl/g).

Figure 4A:
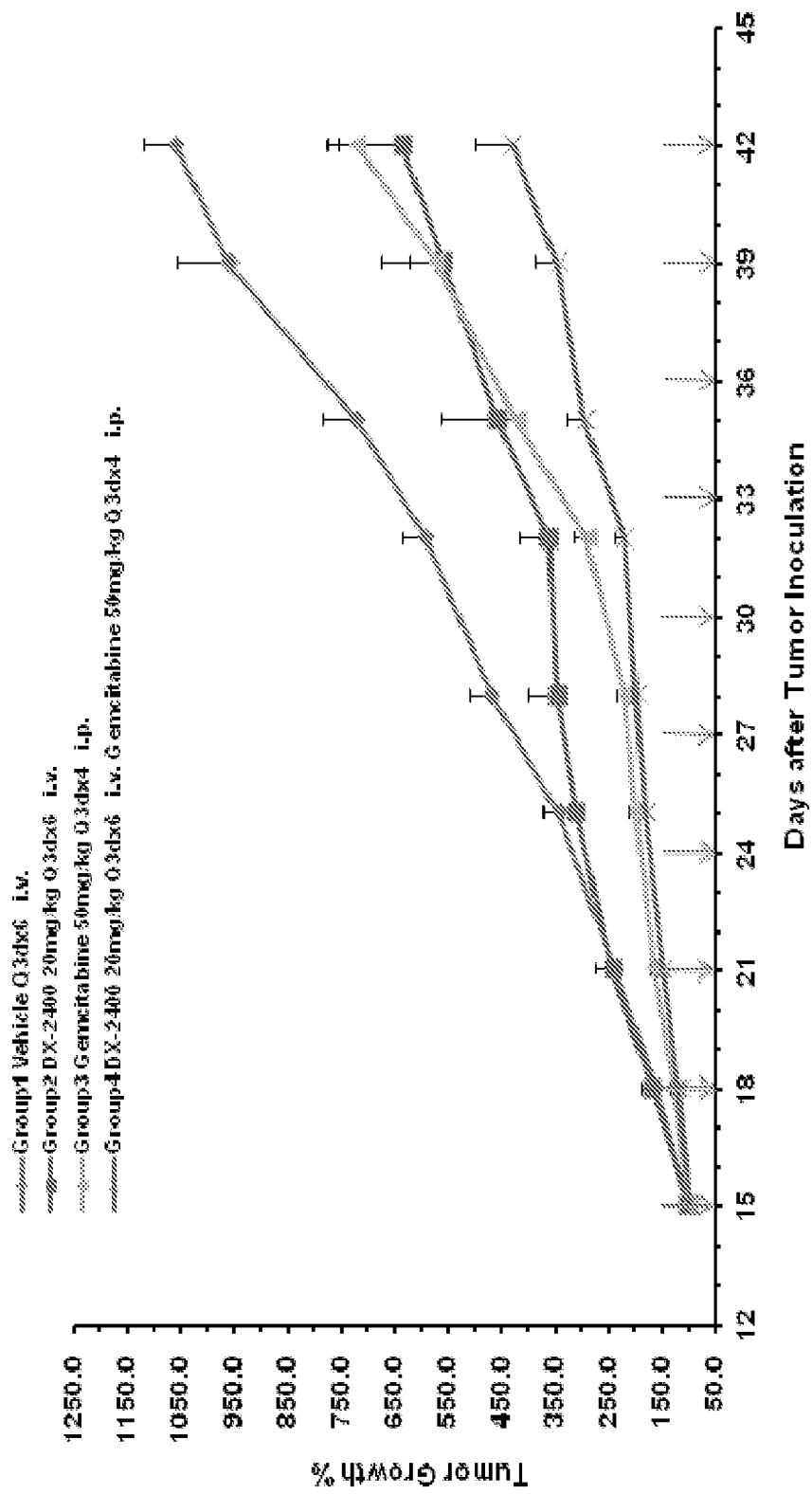
FIGS. 4A and 4B are graphs showing the effect of anti-cancer treatment on mean tumor volume (FIG. 4A) and mean body weight (FIG. 4B) in a xenograft mouse model of pancreatic cancer (Panc-1 cells). Animals were treated with DX-2400 alone, gemcitabine alone, and a combination of gemcitabine and DX-2400.

FIG. 4A shows the mean tumor size over time for each of Groups 1-4 in a mouse xenograft model of human pancreatic cancer (Panc-1 cells). Treatment with DX-2400 alone reduced the mean tumor size as compared to the tumor size observed in untreated mice. Similarly, gemcitabine solo administration also reduced the tumor size as compared to tumor size in untreated mice. In addition, the combination treatment of DX-2400 with gemcitabine reduced tumor volume to a greater degree than the effect of either agent alone.

Figure 4B:
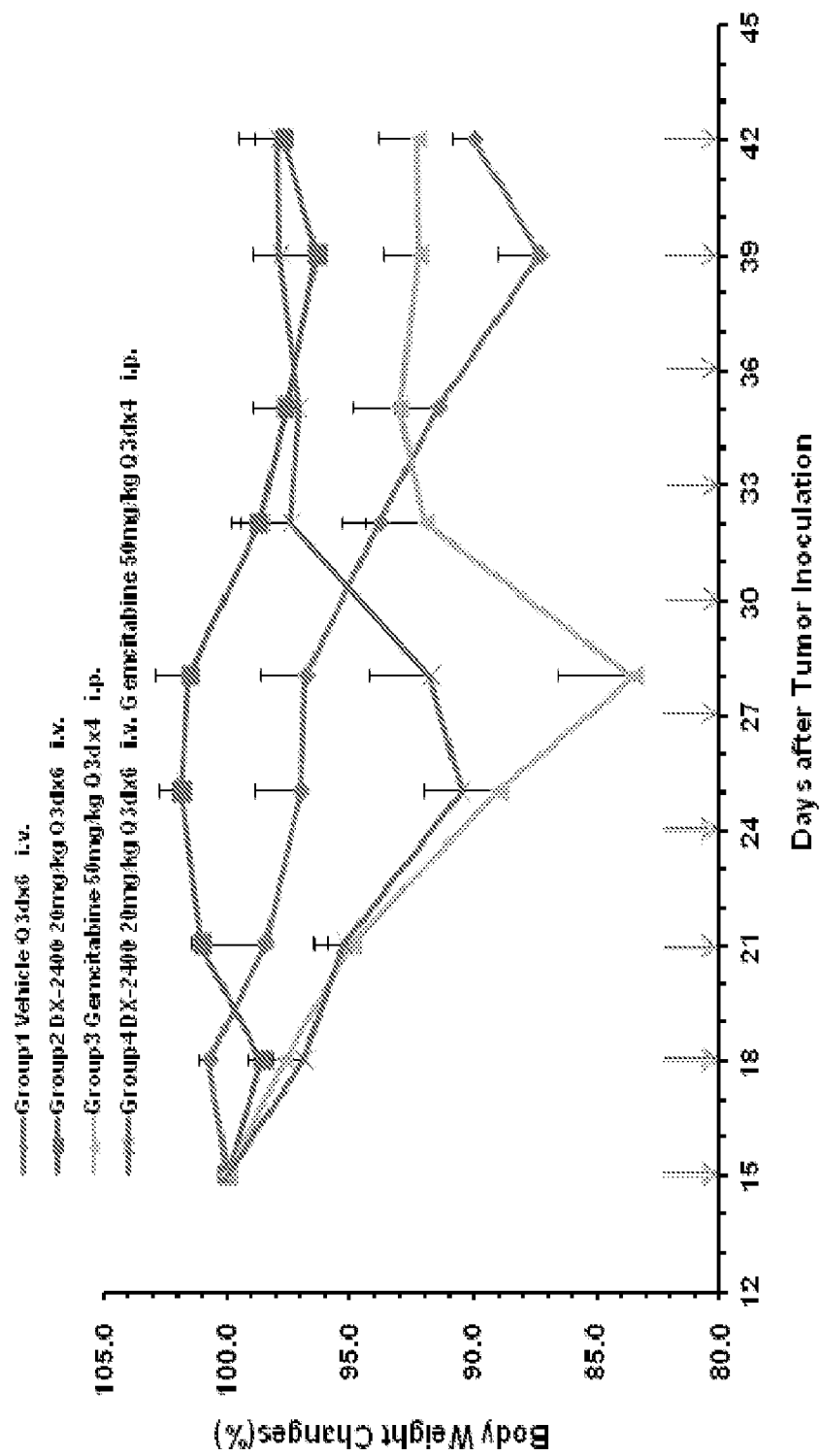

FIG. 4B shows the effect of the different treatments on mean body weight over time. Administration of DX-2400 alone had little effect on the mean body weight as compared to untreated mice. However, administration of gemcitabine alone caused a reduction in body weight as compared to body weights of untreated mice. Combination treatment of mice with both DX-2400 and gemcitabine attenuated the drop in body weight associated with gemcitabine solo treatment.

Example 5: General Methods Relating to Mouse Xenograft Tumor Models

Animal Housing:

An acclimation period of approximately one week between animal receipt and tumor inoculation was observed in order to acclimatize the animals to the laboratory environment. The mice were maintained in a special pathogen-free environment and in polycarbonate cages (~5 mice per cage). All cages, bedding, and water were sterilized before use. When working in the mouse room, the investigators will wear lab coat and latex or vinyl gloves. Each cage will be clearly labeled with a cage card indicating number of animals, sex, strain, receiving date, treatment, study number, group number, and the starting date of the treatment. The cages with food and water will be changed twice a week. The targeted conditions for animal room environment and photoperiod will be as follows:

| | |
|---|---|
| Temperature | 20~26° C. |
| Humidity | 40~70% |
| Light cycle | 12 hours light and 12 hours dark |

Dietary Materials:

All animals have free access to a standard certified commercial laboratory diet. Maximum allowable concentrations of contaminants in the diet are controlled and routinely analyzed by the manufacturers. Autoclaved municipal tap water, suitable for human consumption will be available to the animals ad libitum. It is considered that there are no known contaminants in the dietary materials that could influence the tumor growth.

Aseptic Operation:

The dosing solutions were prepared in a sterile biosafe cabinet and the whole procedures of animal dosing, tumor and body weight measurement were conducted in a sterile hood.

Assignment to Groups:

Before commencement of treatment, all animals are weighed and the tumor volumes are measured. Since the tumor volume can affect the effectiveness of any given treatment, mice were assigned into groups using randomized block design based upon their tumor volumes. This ensures that all the groups were comparable at the baseline.

The randomized block design was used to assign experimental animals to groups. First, the experimental animals were divided into homogeneous blocks according to their initial tumor volume. Secondly, within each block, randomization of experimental animals to treatments was conducted. By using randomized block design to assign experimental animals, it is ensured that each animal has the same probability of being assigned to a given treatment and therefore systematic error will be reduced.

Observations:

The protocol and any amendment(s) or procedures involving the care and use of animals in this study will be reviewed and approved by the Institutional Animal Care and Use Committee (IACUC) of Crownbio prior to conduct. During the study, the care and use of animals will be conducted in accordance with the regulations of the Association for Assessment and Accreditation of Laboratory Animal Care (AAALAC). After inoculation, the animals will be checked daily for morbidity and mortality. At the time of routine monitoring, the animals will be checked for any effects of tumor growth and treatments on normal behavior such as mobility, visual estimation of food and water consumption, body weight gain/loss (body weights will be measured twice weekly), eye/hair matting and any other abnormal effect. Death and observed clinical signs will be recorded on the basis of the numbers of animals within each subset.

Endpoints:

The major endpoint is to see if the tumor growth can be delayed or tumor bearing mice can be cured. Tumor sizes were measured twice weekly in two dimensions using a caliper, and the volume was expressed in $mm^3$ using the formula: $V=0.5 \, a \times b^2$ where a and b are the long and short diameters of the tumor, respectively. The tumor sizes were then used for the calculations of both T-C and T/C values. T-C is calculated with T as the time (in days) required for the mean tumor size of the treatment group to reach a predetermined size (e.g., 1000 $mm^3$), and C is the time (in days) for the mean tumor size of the control group to reach the same size. The T/C value (in percent) is an indication of antitumor effectiveness, T and C are the mean volume of the treated and control groups, respectively, on a given day.

Termination:

Animals that were observed to be in a continuing deteriorating condition or for which the tumor size exceeds 3000 $mm^3$ (or for which the mean tumor size of the group exceeds 2000 $mm^3$) will be euthanized prior to death, or before reaching a comatose state.

During the Study:

Animals exhibiting a first measurement of body weight loss of 20% were given a dose holiday to permit the animal to recover. All other mice in the group were given an identical dose holiday. Animals exhibiting a second measurement of body weight loss of 20% were removed from the study.

The study was ended when the mean tumor burden in the vehicle treated control group reaches a value of 2000 $mm^3$.

Statistical Analysis:

For comparison among groups, a one-way ANOVA was performed followed by multiple comparison procedures. All data will be analyzed using SPSS 16.0. $p<0.05$ is considered to be statistically significant.

What is claimed is:

1. A method for treating a cancer, the method comprising: 1) identifying a subject as being in need of reducing a side effect of a chemotherapeutic agent, wherein the side effect comprises weight loss; and 2) administering to the subject identified in step 1) an MMP-14 binding protein in combination with at least one additional chemotherapeutic agent, wherein the MMP-14 binding protein is an antibody comprising a heavy chain variable domain of SEQ ID NO: 51 and a light chain variable domain of SEQ ID NO: 52; and wherein the cancer is a melanoma, a pancreatic cancer, or a cancer associated with inappropriate angiogenesis.

2. The method of claim 1, wherein the MMP-14 binding protein is administered prior to, during, or following administration of the at least one additional chemotherapeutic agent.

3. The method of claim 1, wherein the cancer is a melanoma.

4. The method of claim 1, wherein the cancer is a metastatic cancer.

5. The method of claim 1, wherein the MMP-14 binding protein is capable of binding to tumor cells or tumor tissues expressing MMP-14.

6. The method of claim 1, wherein the MMP-14 binding protein inhibits MMP-14 activity.

7. The method of claim 1, wherein the subject comprises tumor cells expressing MMP-14.

8. The method of claim 7, further comprising measuring the level of MMP-14 in a biopsy sample obtained from the subject.

9. The method of claim 1, wherein the chemotherapeutic agent is dacarbazine, paclitaxel, or gemcitabine.

10. The method of claim 1, wherein the cancer is a pancreatic cancer.

11. The method of claim 1, wherein the cancer is associated with inappropriate angiogenesis.

12. The method of claim 1, wherein the chemotherapeutic agent is gemcitabine, and wherein the cancer is associated with inappropriate angiogenesis.

13. The method of claim 1, wherein the MMP-14 binding protein is administered at a dose between 5 mg/kg and 50 mg/kg.

14. The method of claim 1, wherein the MMP-14 binding protein is administered at a dose between 10 mg/kg and 25 mg/kg.

15. The method of claim 1, wherein the MMP-14 binding protein is administered in combination with dacarbazine to treat a melanoma.

16. The method of claim 15, wherein the dacarbazine is administered at a dose of 4.5 mg/kg/day or less.

17. The method of claim 1, wherein the MMP-14 binding protein is administered in combination with paclitaxel to treat a melanoma.

18. The method of claim 17, wherein the paclitaxel is administered at a dose of 175 mg/m$^2$ or less.

19. The method of claim 1, wherein the MMP-14 binding protein is administered in combination with gemcitabine to treat a pancreatic cancer.

20. The method of claim 19, wherein the gemcitabine is administered at a dose of 1000 mg/m$^2$ or less.

21. The method of claim 1, wherein the MMP-14 binding protein is an IgG.

22. The method of claim 1, wherein the MMP-14 binding protein is an IgG1.

23. The method of claim 1, wherein the side effect further comprises inability to thrive.

24. The method of claim 1, wherein the cancer is a chemotherapeutic sensitive, chemotherapeutic refractory, chemotherapeutic resistant, or relapsed cancer.

25. The method of claim 1, wherein the cancer is a melanoma and is sensitive, refractory, or resistant to an alkylating agent, a taxane, or an interleukin.

26. The method of claim 25, wherein the alkylating agent is cyclophosphamide, dacarbazine, melphalan, ifosfamide, or temozolomide.

27. The method of claim 25, wherein the taxane is docetaxel, paclitaxel, larotaxel, or cabazitaxel.

28. The method of claim 25, wherein the interleukin is interleukin-2.

29. The method of claim 1, wherein the cancer is a pancreatic cancer and is sensitive, refractory, or resistant to an anti-metabolite.

30. The method of claim 29, wherein the anti-metabolite is an antifolate or a pyrimidine analog.

31. The method of claim 30, wherein the antifolate is pemetrexed, floxuridine, or raltitrexed.

32. The method of claim 30, wherein the pyrimidine analog is capecitabine, cytarabine, gemcitabine, or 5-fluorouracil.

33. The method of claim 1, wherein the chemotherapeutic agent is an anti-metabolite.

34. The method of claim 33, wherein the anti-metabolite is a pyrimidine analog.

35. The method of claim 34, wherein the pyrimidine analog is gemcitabine.

* * * * *